US010235756B2

(12) United States Patent
Brauner et al.

(10) Patent No.: US 10,235,756 B2
(45) Date of Patent: Mar. 19, 2019

(54) VASCULAR ANALYSIS METHODS AND APPARATUS

(71) Applicant: Bio-Tree Systems, Inc., Framingham, MA (US)

(72) Inventors: Raul A. Brauner, Framingham, MA (US); Kongbin Kang, Providence, RI (US); Yanchun Wu, Sharon, MA (US); Joao Cruz, Rumford, RI (US)

(73) Assignee: Bio-Tree Systems, Inc., Framingham, MA (US)

( * ) Notice: Subject to any disclaimer, the term of this patent is extended or adjusted under 35 U.S.C. 154(b) by 170 days.

(21) Appl. No.: 14/692,342

(22) Filed: Apr. 21, 2015

(65) Prior Publication Data

US 2015/0302584 A1 Oct. 22, 2015

Related U.S. Application Data

(63) Continuation of application No. 13/254,913, filed as application No. PCT/US2010/000696 on Mar. 6, 2010.
(Continued)

(51) Int. Cl.
*A61B 6/00* (2006.01)
*G06T 7/00* (2017.01)
(Continued)

(52) U.S. Cl.
CPC ............ *G06T 7/0016* (2013.01); *A61B 6/508* (2013.01); *G06T 7/11* (2017.01); *G06T 7/13* (2017.01);
(Continued)

(58) Field of Classification Search
USPC ........................................................ 600/481
See application file for complete search history.

(56) References Cited

U.S. PATENT DOCUMENTS 6,535,623 B1  3/2003  Tannenbaum et al.
8,687,862 B2  4/2014  Hsu et al.
(Continued)

FOREIGN PATENT DOCUMENTS

JP  10-243924 A     9/1998
WO  2006/085254 A1  8/2006
WO  2008/002648 A2  1/2008

OTHER PUBLICATIONS

Office action dated Oct. 22, 2014 in related U.S. Appl. No. 13/254,913.
(Continued)

*Primary Examiner* — Christian Jang
*Assistant Examiner* — Mitchell E Alter
(74) *Attorney, Agent, or Firm* — Nields, Lemack & Frame, LLC

(57) ABSTRACT

According to some aspects, a method of identifying a boundary of a portion of a vasculature is provided, the vasculature comprising a geometric representation of a plurality of vessels. The method comprises logically dividing the geometric representation into a plurality of regions, determining at least one feature within each of the plurality of regions, and defining the boundary of the portion of the vasculature based, at least in part, on the at least one feature determined within each of the plurality of regions, wherein the boundary forms a volume defining a separation between inside and outside of the portion of the vasculature. According to some aspects, a method of performing vascular analysis using a geometric representation of a plurality of vessels of the vasculature is provided. The method comprises computing a boundary of a portion of the vasculature based on the geometric representation, logically dividing the geometric representation within the boundary into a plurality of regions, and analyzing at least one feature for each of the plurality of regions within the boundary.

20 Claims, 57 Drawing Sheets

Related U.S. Application Data

(60) Provisional application No. 61/209,386, filed on Mar. 6, 2009.

(51) Int. Cl.
*G06T 7/11* (2017.01)
*G06T 7/13* (2017.01)
*G06T 7/149* (2017.01)
*G06T 7/155* (2017.01)

(52) U.S. Cl.
CPC ............. *G06T 7/149* (2017.01); *G06T 7/155* (2017.01); *G06T 2207/10072* (2013.01); *G06T 2207/20021* (2013.01); *G06T 2207/20036* (2013.01); *G06T 2207/20112* (2013.01); *G06T 2207/30101* (2013.01); *G06T 2207/30172* (2013.01)

(56) References Cited

U.S. PATENT DOCUMENTS

| | | | |
|---|---|---|---|
| 8,879,813 B1 | 11/2014 | Solanki et al. | |
| 9,721,341 B2 | 8/2017 | Kang et al. | |
| 9,898,659 B2 | 2/2018 | Kanagasingam et al. | |
| 2003/0176780 A1* | 9/2003 | Arnold | G06T 7/0012 600/407 |
| 2006/0029927 A1* | 2/2006 | Johnson | A61B 5/02007 435/4 |
| 2008/0260229 A1* | 10/2008 | Mashiach | A61B 6/504 382/131 |
| 2011/0080558 A1 | 4/2011 | Marshall et al. | |
| 2012/0027275 A1 | 2/2012 | Fleming | |
| 2012/0150048 A1 | 6/2012 | Kang et al. | |
| 2016/0174830 A1 | 6/2016 | Rubin et al. | |
| 2017/0156582 A1 | 6/2017 | Ehlers et al. | |
| 2017/0278243 A1 | 9/2017 | Kang et al. | |
| 2017/0287131 A1 | 10/2017 | Kang et al. | |
| 2017/0316165 A1 | 11/2017 | Brauner et al. | |

OTHER PUBLICATIONS

International Search Report and Written Opinion dated Nov. 22, 2010 in corresponding PCT application No. PCT/US2010/000696.
International Preliminary Report on Patentability dated Sep. 15, 2011 in corresponding PCT application No. PCT/US2010/000696.
European communication dated Apr. 26, 2018 in corresponding European patent application No. 10749066.6.
Office action dated Feb. 28, 2018 in co-pending U.S. Appl. No. 15/581,315.
Canadian communication dated Jan. 22, 2018 in corresponding Canadian patent application No. 2,792,354.
Office action dated Jun. 26, 2018 in co-pending U.S. Appl. No. 15/581,315.

\* cited by examiner

BT38 - Photo Image
Sub-Q Xenograft
Gioblastoma U87 Tumor Model
Avastin Treated

BT38 - X-Ray Raw View Image
Sub-Q Xenograft
Gioblastoma U87 Tumor Model
Avastin Treated BT38 - 3D Reconstructed
Tumor Vasculature
Sub-Q Xenograft
Glioblastoma U87 Tumor Model Avastin Treated

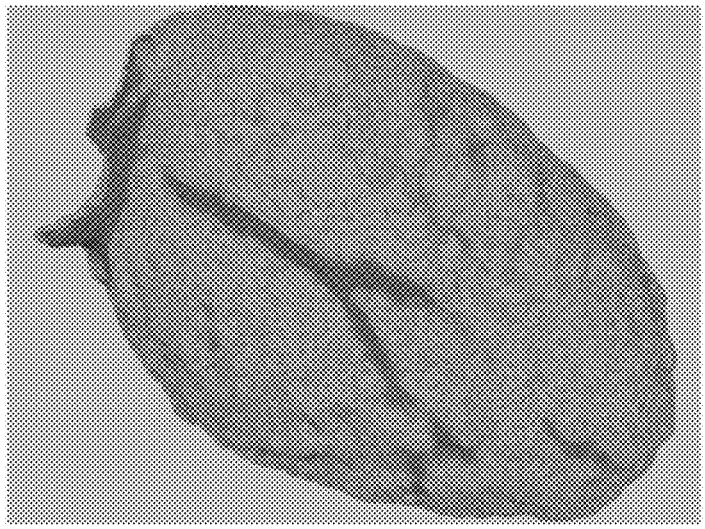
Fig. 68
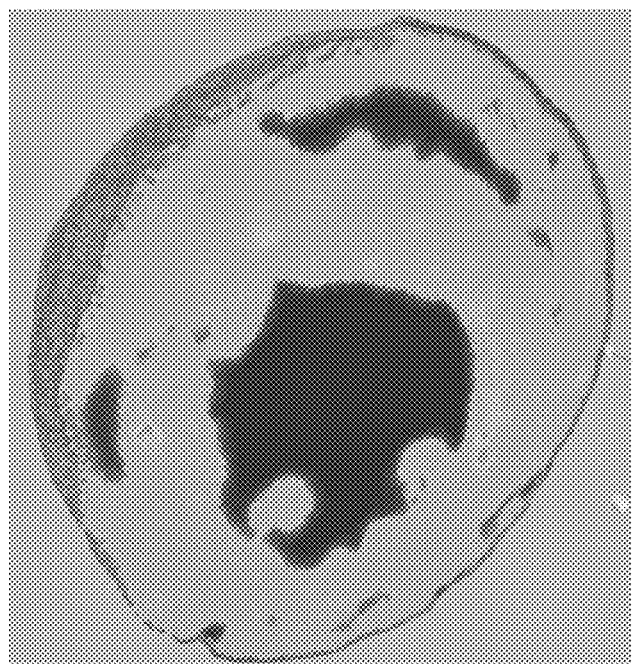 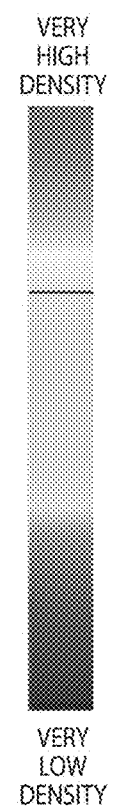
Fig. 69

(i)           (ii)

VASCULAR ANALYSIS METHODS AND APPARATUS

RELATED APPLICATIONS

This Application is a continuation, and claims the benefit under 35 U.S.C. § 120, of U.S. application Ser. No. 13/254,913, entitled "VASCULAR ANALYSIS METHODS AND APPARATUS" filed on Feb. 16, 2012, which is a national stage application under 35 U.S.C. § 371 of PCT International Application No. PCT/US2010/000696, entitled "VASCULAR ANALYSIS METHODS AND APPARATUS" filed on Mar. 6, 2010, which claims priority under 35 U.S.C. § 119(e) to U.S. Provisional Application Ser. No. 61/209,386, entitled "VASCULAR BIOMARKERS FOR DIAGNOSTIC AND THERAPEUTIC USE" filed on Mar. 6, 2009, each of which are herein incorporated by reference in its entirety.

BACKGROUND OF THE INVENTION

A wide range of imaging methods and devices are commonly used to evaluate different anatomical and physiological conditions in a variety of medical and research environments. Tools have been developed to image body structures based on different physical properties. For example, X-rays, CT scans, MRIs, PET scans, IR analyses and other technologies have been developed to obtain images of various body structures. These tools are routinely used for diagnostic, therapeutic, and research applications. Combinations of two or more different imaging techniques are sometimes used to provide complementary information about a patient.

In conventional medical imaging, a human operator, such as a physician or diagnostician, may visually inspect one or more images to make an assessment, such as detection of a tumor or other pathology or to otherwise characterize the internal structures of a patient. However, this process may be difficult and time consuming. For example, it may be difficult to assess 3D biological structure by attempting to follow 2D structure through a series of stacked 2D images. In particular, it may be perceptually difficult and time consuming to understand how 2D structure is related to 3D structure as it appears, changes in size and shape, and/or disappears in successive 2D image slices. A physician may have to mentally arrange hundreds or more 2D slices into a 3D picture of the anatomy. To further frustrate this process, when anatomical structure of interest is small, the structure may be difficult to discern or it may be difficult to understand how numerous structures relate to a biological whole.

Furthermore, in addition to the time consuming nature of manual inspection, human visual interpretation of images has further shortcomings. While the human visual cortex processes image information to obtain qualitative information about structure in the image, it does not compute quantitative geometry from the image. However, the quantitative geometry of the structure represented in one or more images may contain valuable information about the structure that can be used to diagnose disease, assess the efficacy of treatment and/or perform other analyses of the structure. Such quantitative information about the structure is beyond the capability of conventional human visual image understanding alone.

Image processing techniques have been developed to automate or partially automate the task of understanding and partitioning the structure in an image and are employed in computer aided diagnosis (CAD) to assist a physician in identifying and locating structure of interest in a 2D or 3D image. CAD techniques often involve segmenting the image into groups of related pixels and identifying the various groups of pixels, for example, as those comprising a tumor or a vessel or some other structure of interest. However, conventional segmentation may produce unsatisfactory or incomplete results, particularly when the structure being detected appears in the image at arbitrary locations, sizes and orientations. As a result, the limited geometry that may be extracted from conventional image processing may be unsuitable for use in further analysis based on the extracted geometry.

SUMMARY OF THE INVENTION

Applicant has developed methods and apparatus for extracting geometry from images, scan data, and/or representations of tubular body structures (e.g., blood vessels or other body vessels). Aspects of the invention relate to obtaining vessel geometry, determining one or more structural features from the vessel geometry, and/or analyzing the one or more structural features for medical diagnostic, prognostic, and/or research applications.

Aspects of the invention relate to methods and systems for analyzing vascular structures obtained from vascular imaging and/or reconstruction. In some embodiments, vascular information may be segmented based on one or more morphological features to identify and/or analyze organs, sub-organ, or other body regions of interest (e.g., including tumors, or other regions of diseased tissue that can be identified and/or segmented based on vascular morphology). The segmented information may be used for disease detection, monitoring or evaluating disease progression, monitoring or evaluating disease response to therapy (e.g., including analyzing the mechanism of the therapy), evaluating or detecting therapy toxicity, therapy optimization, etc., or any combination thereof.

In some embodiments, aspects of the invention relate to identifying a precise boundary between tissue or body regions having different vascular morphologies. In some embodiments, aspects of the invention relate to identifying a region or zone having a particular vascular morphology (e.g., a zone that is different from and separates two regions that themselves have similar vascular morphologies). The regions may be organs, or sub-organ regions, or any other regions of interest that can be distinguished based on particular vascular morphologies and/or that are bounded by particular vascular morphologies. In some embodiments, such segmentation techniques are referred to herein as wrapping.

Accordingly, in some embodiments aspects of the invention relate to identifying a volume of interest based on vascular parameters (e.g., by analyzing a vascular geometry). In some embodiments, aspects of the invention relate to providing a vascular geometry within a region of interest. In some embodiments, once the volume has been identified, one or more features within the volume may be analyzed (e.g., based on the vascular geometry within the region) as described herein, e.g., for diagnostic, therapeutic, or other applications as described herein.

In some embodiments, aspects of the invention relate to analyzing vascular and/or other information within a region that has been identified based on vascular morphological segmentation (e.g., a wrapped region). Any suitable information may be analyzed within a wrapped region. In some embodiments, wrapping defines a volume of a region. Accordingly, one or more vascular parameters may be analyzed as a function of volume within the region (e.g., vascular density, microvessel density, binned vascular density, vascular volume, binned vascular volume, etc., or any combination thereof). In some embodiments, this information may be obtained from a "poker chip" representation of the vasculature (e.g., within the wrapped region) as described herein. In some embodiments, the "poker chip" information alone may be sufficient (e.g., for evaluating vessel diameter, volume, density, or any combination thereof). In some embodiments, linking information is provided. In some embodiments, linking information may be used to evaluate vessel branching and other geometrical features as described herein.

In some embodiments, the vasculature of a region of interest may be measured as the total vasculature within a unit volume or area. In some embodiments, the vasculature of a region of interest may be measured as a vascular density, e.g., as the percentage of a region that consists of vasculature. In a volume (e.g., in a 3D representation) the vascular density may be represented as the percentage of the volume that consists of vasculature. In an area (e.g., in a 2D representation or a slice through a volume) the vascular density may be represented as the percentage of the surface area that consists of vasculature. In some embodiments, the relative amount of vasculature may be represented as the vascular surface area within a volume or a slice. For example, in a volume, the surface area of vasculature may be calculated based on the circumference and thickness of all the "poker chips" that represent the vasculature within the volume. However, it should be appreciated that the relative amount of vasculature within a defined volume or area may be calculated using any suitable method as aspects of the invention are not limited in this respect. In some embodiments, the vasculature (e.g., measured by total vascular volume, total vascular density, total vascular surface, etc., or any other metric, or any combination thereof within a 2D or 3D region) may be provided as a value or an average for a region of interest. In some embodiments, the vasculature (e.g., measured by vascular volume, vascular density, vascular surface, etc., or any other metric, or any combination thereof within a 2D or 3D region) may be binned into vessels of different diameter to display a binned distribution of vascular volume or density within a region of interest. In some embodiments, the blood vessels that are analyzed are micro-vessels (e.g., with a diameter of less than 1 mm, less than 100 microns, from 10 to about 100 microns). Accordingly, in some embodiments, micro-vessels may be binned into bins of approximately 10 micron intervals (e.g., 10-20, 20-30, 30-40, 40-50, 50-60, 60-70, 70-80, 80-90, 90-100 microns, etc.). However, any suitable interval may be used (e.g., as illustrated herein) as aspects of the invention are not limited in this respect.

In some embodiments, one or more other morphological features may be analyzed within a region of interest. For example, a geometrical representation of a vascular network refers herein to a mathematical description and/or a model of the geometry of at least some of the vessels in the vascular network. The geometrical representation may include, but is not limited to geometric information such as vessel location, vessel diameter, vessel orientation, vessel length, etc. The geometrical representation may be used to obtain, or may include, higher order geometric features such as how the vessel are linked, vessel branching information, vessel length, vessel length between branching points, vessel curvature and/or tortuosity. The geometrical representation may also be used to determine other features such as vessel density, binned vessel density, vessel surface area, etc., as discussed in further detail below. In general, many potentially useful morphological features of a vascular network may be obtained from the geometric representation of the vascular network. Any one or more of these features, in addition to or instead of the measures of vascular volume (e.g., density, surface area, etc.) may be analyzed alone or in combination for the region of interest.

In some embodiments, a wrapped region may be further segmented into smaller regions of interest. It should be appreciated that any of the analytical techniques described herein for a total wrapped region (e.g., a total tumor volume) may be applied to the vasculature within a smaller region. In some embodiments, a smaller region may be a 2D slice (e.g., a subset of the data representing a 2D region of the region, a vascular hotspot region (e.g., a volume or 2D area within which the vascular density, or other measure of vasculature, is above a predetermined threshold), one or more iso-shells (e.g., a region in a bounded vasculature wherein locations—e.g., discrete volumes in the bounded vasculature—within each iso-shell have a distance from the boundary that are within the same range of values defined by the respective iso-shell) or other region of interest, or any combination thereof.

Accordingly, aspects of the invention provide a hierarchical analysis comprising one or more of the following acts: identifying a first region of interest such as a tumor or organ (e.g., based on morphological features or based on wrapping as described herein), identifying one or more sub-regions of interest within the first-region (e.g., as one or more hotspots, as slices, as iso-shells, or any combination thereof), analyzing one or more vascular morphologies (e.g., a combination of 2, 3, 4, 5, or more) within the sub-region of interest. Non-limiting examples of vascular morphological features include vessel location, vessel diameter, vessel orientation, vessel length, how the vessels are linked, vessel branching information, vessel length, vessel length between branching points, vessel curvature and/or tortuosity, vessel density, binned vessel density, vessel surface area, vascular volume (e.g., density, surface area, etc.), or any others, or any combination thereof.

It should be appreciated that the hot spot regions may be identified and analyzed independently or in conjunction with the use of wrapping techniques.

In some embodiments, the information (e.g., related to vascular morphology) within a region of interest is associated with unit volumes (also referred to as ice cubes). For example, each unit volume may contain a number of vessels, a number of vessel cross-sections, a total vascular volume, a percentage vascularity, a total vascular surface, a percentage vascular surface, a measure of any other morphological feature described herein, or any combination thereof. A quantitative analysis then may be performed using the unit volumes (or ice cubes) to compare one tissue to another (e.g., subject to healthy, subject to diseased, subject to treatment reference, one drug to another, treatment to no treatment, etc., or any combination thereof).

In some embodiments, a hotspot may be identified by setting a threshold of vascular content within a unit volume (e.g., a cubic mm) and identifying any unit volume as being part of a hot spot if the vascular content within the unit volume exceeds the threshold. In some embodiments, the vascular content may be evaluated as the number of vascular "poker chips" within a unit volume. It should be appreciated that aspects of the invention allow the user to select an appropriate unit volume and an appropriate vascular threshold to identify one or more hot spots.

In some embodiments, information from the analysis of a total region (an entire organ, a tumor), a 3D volume, a 2D slice, a hot-spot, an iso-shell, or other sub-region may be used as a reference (e.g., a biomarker) for either a normal tissue, a diseased tissue, a response to therapy, any other disease or condition described herein, etc., or any combination thereof. In some embodiments, a biomarker may be also include a time-dependent change of one or more vascular morphologies based any of these analyses.

It should be appreciated that methods, systems, and techniques described herein may be used to evaluate image information obtained from any suitable source (including image information relating to in vivo or in vitro vascular structures). In some embodiments information may obtained using contrast agents. In some embodiments, information may be obtained using tissue casting and contrast agents. However, aspects of the invention are not limited in this respect in that any data that provides information suitable to analyze vascular structures as described herein may be used.

It should be appreciated that aspects of the invention may be used to evaluate normal organs, normal tissues, diseased tissues, diseased organs, tumors (e.g., tumor models, for example, orthotopic and/or xenotopic tumor models), etc., or any combination thereof. Non-limiting examples of organs and tissues include heart, liver, kidney, brain, lymph nodes, muscles, pancreas, joints, reproductive organs and tissue, gastrointestinal organs and tissue, bones, and combinations thereof.

Accordingly, aspects of the invention may be used for virtual histology of an organ or region as described herein (e.g., a wrapped organ or region). In some embodiments, aspects of the invention provide virtual vascular anatomies of one or more organs or regions (e.g., wrapped organs or regions). These can be used to evaluate a subject's structural information and determine whether it is normal, diseased, indicative of disease progression or response to therapy, etc., or any combination thereof.

In some embodiments, aspects of the invention may be used for radiation planning, targeting, monitoring and/or treatment evaluation. In some embodiments, aspects of the invention may be used for tissue ablation (e.g., tumor ablation) planning, targeting, monitoring, and/or ablation treatment evaluation. In some embodiments, aspects of the invention relate to thrombo-embolization (e.g., virtual or actual).

Some embodiments include a method of identifying a boundary of a portion of a vasculature, the vasculature comprising a geometric representation of a plurality of vessels, the method comprising logically dividing the geometric representation into a plurality of regions, determining at least one feature within each of the plurality of regions, defining the boundary of the portion of the vasculature based, at least in part, on the at least one feature determined within each of the plurality of regions, wherein the boundary forms a volume defining a separation between inside and outside of the portion of the vasculature.

Some embodiments include at least one computer readable medium encoded with instructions that, when executed by at least one processor, performs a method of identifying a boundary of a portion of a vasculature, the vasculature comprising a geometric representation of a plurality of vessels, the method comprising logically dividing the geometric representation into a plurality of regions, determining at least one feature within each of the plurality of regions, and defining the boundary of the portion of the vasculature based, at least in part, on the at least one feature determined within each of the plurality of regions, wherein the boundary forms a volume defining a separation between inside and outside of the portion of the vasculature.

Some embodiments include an apparatus for identifying a boundary of a portion of a vasculature, the vasculature comprising a geometric representation of a plurality of vessels, the method comprising at least one storage medium to store the geometric representation, and at least one computer capable of accessing the at least one storage medium to obtain the geometric representation. The at least one computer is programmed to logically divide the geometric representation into a plurality of regions, determine at least one feature within each of the plurality of regions, and define the boundary of the portion of the vasculature based, at least in part, on the at least one feature determined within each of the plurality of regions, wherein the boundary forms a volume defining a separation between inside and outside of the portion of the vasculature.

Some embodiments include a method of performing vascular analysis using a geometric representation of a plurality of vessels of the vasculature, the method comprising computing a boundary of a portion of the vasculature based on the geometric representation, logically dividing the geometric representation within the boundary into a plurality of regions, and analyzing at least one feature for each of the plurality of regions within the boundary.

Some embodiment include at least one computer readable medium encoded with instructions that, when executed on at least one processor, performs a method of performing vascular analysis using a geometric representation of a plurality of vessels of the vasculature, the method comprising computing a boundary of a portion of the vasculature based on the geometric representation, logically dividing the geometric representation within the boundary into a plurality of regions and analyzing at least one feature for each of the plurality of regions within the boundary.

Some embodiments include an apparatus for performing vascular analysis using a geometric representation of a plurality of vessels of the vasculature, the apparatus comprising at least one storage medium for storing the geometric representation, and at least one computer capable of accessing the at least one storage medium to process the geometric representation. The at least one computer is programmed to compute a boundary of a portion of the vasculature based on the geometric representation, logically divide the geometric representation within the boundary into a plurality of regions, and analyze at least one feature for each of the plurality of regions within the boundary.

BRIEF DESCRIPTION OF THE DRAWINGS

FIG. 68 illustrates a wrapped density field view of mouse heart vasculature;

FIG. 69 illustrates a wrapped density field cross section view of mouse heart vasculature;

DEFINITIONS

Figure 1:
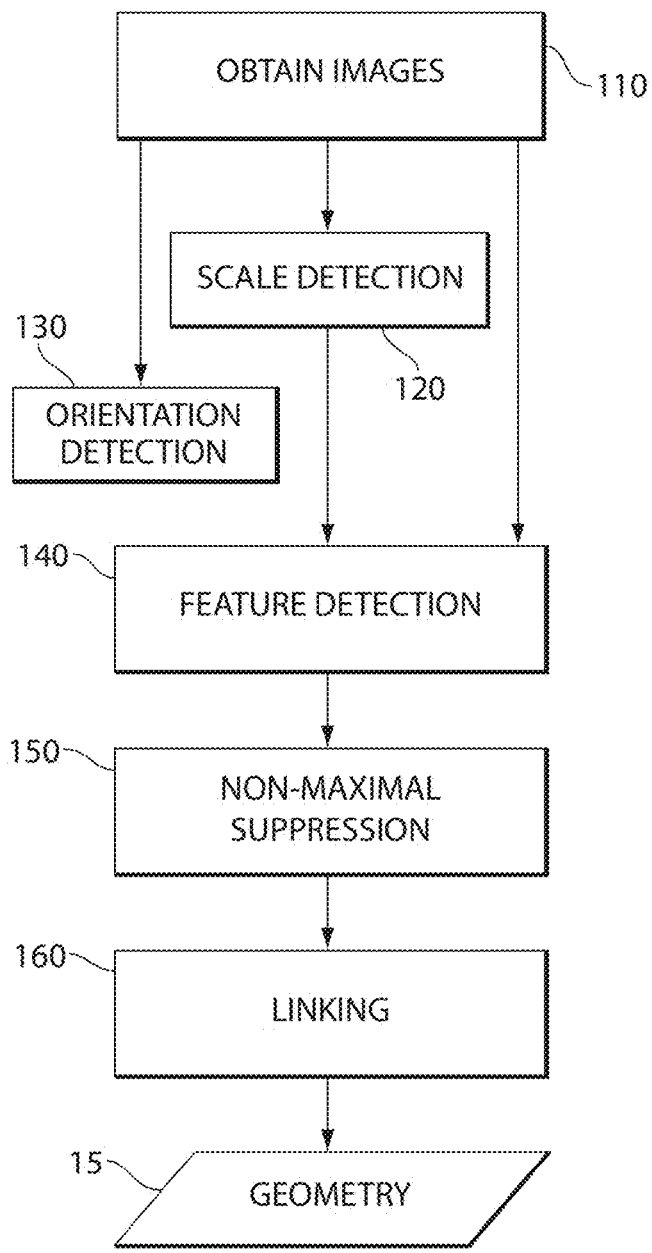
FIG. 1 illustrates a flow chart of extracting geometry from an image, in accordance with some embodiments of the invention.

As used herein, the terms "medical imaging technology" and "imaging technology" are used interchangeably, and refer to any type of technique and/or process used to create images of the human body (or parts thereof) for clinical purposes (medical procedures seeking to reveal, diagnose or examine disease) or medical science (including the study of normal anatomy and physiology). Any imaging technology that yields high resolution three-dimensional information, is useful according to some aspects of this invention. Various types of magnetic resonance imaging (MRI) technology, for example magnetic resonance angiography, various types of computed tomography (CT), also sometimes referred to as computed axial tomography (CAT), and various types of positron emission tomography (PET), are examples of technologies useful according to some aspects of this invention. Imaging technologies useful according to some aspects of this invention allow for three-dimensional image reconstruction from acquired imaging data, for example by multiplanar reconstruction, surface rendering, volume rendering, or image segmentation approaches.

In some embodiments, medical imaging, for example, CT, may be performed without the administration of a contrast agent. In some embodiments, in order to image some lower-contrast structures, for example peripheral vasculature, as related to by some aspects of this invention, medical imaging results may be enhanced by the use of a contrast agent. Contrast agents for medical imaging technologies are well known to those of skill in the art and are, for example, described in W. Krause, *Contrast Agents I—Magentic Resonance Imaging*, Springer, 2002, ISBN 3-540-42247-1, and W. Krause, *Contrast Agents II—Optical, Ultrasound, X-Ray, and Radiopharmaceutical Imaging*, Springer, 2002, ISBN 3-540-43451-8, both incorporated in their entirety herein for disclosure of contrast agents. containing elements of a higher atomic number than the surrounding tissue, for example iodine, barium, barium sulfate, or gastrografin. Contrast agents may be administered via various routes, for example by intravenous injection, or by oral administration. In some embodiments, a contrast agent may be formulated in a way that allows targeted delivery of the contrast agent to a specific tissue, cell type, or target structure, for example to a blood vessel, blood vessel type, or blood vessel substructure in a diseased tissue, for example, a tumor. Formulations of contrast agents useful for targeted delivery, for example, contrast agent encapsulation (e.g. microencapsulated or nanoencapsulated), association, or conjugation in or to a delivery vector, for example, a lipid, a lipoprotein, a protein or peptide, a binding agent (e.g. an antibody, a fragment thereof, an antibody-labeled liposome, e.g., to antigen of blood vessel, organ, disease, etc.), as well as routes and modes of administration of such formulations are known to those of skill in the art.

The term "vasculature" refers to the system of blood vessels in a tissue or body. This includes, for example, arteries (blood vessels carrying blood away from the heart, for example arteries delivering oxygenated blood to a peripheral tissue), veins (blood vessels carrying blood back to the heart, for example veins removing deoxygenated blood from a peripheral tissue), arterioles (small diameter blood vessels branching out from an artery and leading to a capillary), venules (small blood vessels connecting a capillary to a vein), and capillaries.

The term "radiotherapy", sometimes also referred to as "radiation therapy", or "radiation oncology", as used herein, refers to the medical use of ionizing radiation. Radiotherapy may be used alone, or in combination with other clinical interventions, for example administration of anti-angiogenic drugs. Radiotherapy is commonly applied to malignant tissues, for example tumors in order to induce cell death, and/or inhibit proliferation. Radiotherapy may comprise the administration of a single dose of ionizing radiation using a single beam, or a plurality of beams, or the repeated administration of ionizing radiation over a period of time, for example in multiple sessions. The term "ionizing radiation", as used herein, refers to radiation consisting of sub atomic particles or electromagnetic waves that are energetic enough to detach electron atoms or molecules, ionizing them. Examples of ionizing particles are energetic alpha particles, beta particles, and neutrons. Examples of ionizing electromagnetic waves are ultraviolet light, x-rays, and gamma rays.

The terms "imaging-guided radiation therapy" and "imaging-guided radiotherapy", as used herein, refer to any type of radiotherapy in which a beam of ionizing radiation is aimed at a therapeutic target structure using imaging information obtained from the target structure. The imaging information may be obtained before or during the administration of a dosage of ionizing radiation. The terms "image-guided" and "imaging-guided" are used interchangeably herein.

The term "stereotactic radiosurgery", as used herein, refers to a highly precise form of radiation therapy, using highly focused beams of ionizing radiation that are delivered to a target tissue with high precision and converge at the site of a target structure, for example a tumor or a tumor substructure, thus delivering a high dosage of ionizing radiation to said target structure.

The term "chemotherapeutic agent", as used herein, refers to any chemical, for example a drug or compound, used or useful in the treatment of disease. For example, the term refers to cytostatic, cytotoxic, and/or anti-neoplastic drugs used to treat cancer or a combination of drugs used in a standardized cancer treatment regimen. Non-limiting examples of chemotherapeutic agents are alkylating agents, such as cisplatin, carboplatin, oxalyplatin, mechlorethamine, cyclophosphamide, or chlorambucil, anti-metabolites, such as purine analogues azathioprine, mercaptopurine, or pyrimidine analogues, plant alkaloids and terpenoids, such as vinca alkaloids (for example vincristine, viblastine, vinorelbine, vindesine), taxanes (for example paclitaxel, taxol, or docetaxel), or podophyllotoxin and its derivatives (for example etoposide or teniposide), topoisomerase inhibitors, such as camptothecins (for example irinotecan or topotecan), amsacrine, epidophyllotoxin derivatives, and antitumor antibiotics, such as dactinomycin, doxorubicin, epirubicin, bleomycin, plicamycin, mitomycin etc.

As used herein, the term "subject" refers to an individual, for example a human, non-human primate, cow, horse, pig, sheep, goat, dog, cat, rodent, or other mammal.

The term "automatic" or "automated" is used herein to describe methods, processes or acts within a method or process that is performed substantially by at least one computer. An act performed automatically indicates that the corresponding output was determined by the at least one computer. Act in which inputs such as parameters or variables are provided or selected manually (e.g., by a human) are still considered automatic or automated provided at least one computer is computing the result or output.

DETAILED DESCRIPTION

As discussed above, analyzing vessel structures (e.g., blood vessel structures) and identifying structural profiles that are characteristic of one or more physiological conditions or responses (e.g., positive responses to pharmaceutical compounds) may be of interest in many areas of diagnostics, therapeutics and/or treatment. However, the amount of information that can be directly obtained or ascertained from image data (e.g., x-ray, CT, MRI, etc.) may be prohibitively limited in this respect. Accordingly, Applicant has recognized the benefit of developing methods of extracting geometry from images to facilitate the above described analysis. Subsequent to extracting geometrical properties of a vascular network have been from one or more images, the resulting geometrical representation of the vascular network may be analyzed to mine data for physiological, biological, and/or medical purposes.

A geometrical representation of a vascular network refers herein to a mathematical description and/or a model of the geometry of at least some of the vessels in the vascular network. The geometrical representation may include, but is not limited to geometric information such as vessel location, vessel diameter, vessel orientation, vessel length, etc. The geometrical representation may be used to obtain, or may include, higher order geometric features such as how the vessel are linked, vessel branching information, vessel length, vessel length between branching points, vessel curvature and/or tortuosity. The geometrical representation may also be used to determine other features such as vessel density, binned vessel density, vessel surface area, etc., as discussed in further detail below. In general, many potentially useful morphological features of a vascular network may be obtained from the geometric representation of the vascular network.

Applicant has appreciated that some information that may be useful in a physiological, biological, and/or medical context may be obtainable if the boundary of a portion of interest of a vascular network were known and/or defined. For example, if the boundary of the vasculature of a particular organ or a boundary defining the extent of the vasculature belonging to a tumor could be determined, potentially important diagnostic and/or prognostic information may be gleaned from the geometric representation of the vascular network.

Applicant has developed automated techniques for determining and defining a boundary of a portion of interest of a vascular network from a geometric representation of the vascular network. According to some embodiments, a boundary is defined based on at least one feature of the geometric representation of the vascular network. For example, the at least one feature may include (but are not limited to) any one or combination of vessel density, binned vessel density, branch density, measures of curvature and/or tortuosity and/or measures of vessel orientation, length and/or diameter. The boundary may form a volume that defines which vessels are inside the volume and which vessels outside the volume. For example, a organ boundary may define which vessels are part of the organ and which are not. Likewise, a tumor boundary may define which vessels are part of the tumor and which vessels are not. Subsequent to determining a boundary, various morphological attributes of the vasculature may be obtained and analyzed, as discussed in further detail herein.

Following below are more detailed descriptions of various concepts related to, and embodiments of, methods and apparatus according to the present invention. It should be appreciated that various aspects of the invention described herein may be implemented in any of numerous ways. Examples of specific implementations are provided herein for illustrative purposes only. In addition, the various aspects of the invention described in the embodiments herein may be used alone or in any combination, and are not limited to the combinations explicitly described herein.

As discussed above, having the ability to determine the boundary of at least a portion of a vascular network may provide valuable tool for medical diagnostic, prognostic, and/or research applications including, but not limited to, analyzing structures such as blood vessels and the morphological attributes of a bounded vascular network to evaluate their association with disease, responsiveness to therapeutic treatments, and/or other conditions.

It should be appreciated that a geometric representation of a vascular network may need to be obtained before a boundary of at least a portion of the vascular network may be determined and/or defined. The geometric representation of a vascular network may be computed from one or more images of the vascular network or a stored geometric representation may be acquired. Provided below are techniques for extracting a geometric representation of a vascular network from one or more images of the vascular network. Such techniques are described in WO 2009/088963 A2, entitled "Methods of obtaining geometry from images", which is incorporated herein by reference in its entirety.

I. Extraction of a Geometric Representation of a Vascular Network

FIG. 1 illustrates a method of extracting vessel geometry from one or more images of vasculature, in accordance with some embodiments of the present invention. Act 110 includes obtaining image information of at least a portion of a vasculature structure. For example, the image information may be a two-dimensional (2D), three-dimensional (3D) or other dimensional image obtained from scanning an object using x-ray CT, MRI, PET, SPECT, etc. The scanned object may be a live specimen such as a human or other animal (i.e., an in-vivo scan), or obtained from a cast of a specimen's vasculature.

The method of FIG. 1 may be performed on any image of any dimension independent of how the image was obtained, as the aspects of the invention are not limited in this respect. In 2D images, each 2D location having an associated intensity is conventionally referred to as a pixel. In 3D images, each volume location having an associated intensity is conventionally referred to as a voxel. The term voxel is used herein to refer to both 2D and 3D image locations to eliminate the need to specify the dimensionality of the images, as the methods described herein are generic to dimensionality.

Many techniques for extracting information from images use various filtering techniques. For example, filters are often designed such that when applied to a portion of an image (e.g., convolved with a portion of the image) the filter response is relatively large when the filter is applied to an image portion having a feature or characteristic indicative of structure being detected in the image, and relatively small otherwise. The filter detection described below in connection with act 140 is one example of matched filtering. However, other filtering techniques may be used, as the aspects of the invention are not limited in this respect.

When the feature or structure being detected appears in an image at different sizes or scales, the size of the filter kernel should be adjusted to the appropriate scale in order for the filter response to accurately indicate the presence of the desired feature. For example, in an image containing biological vasculature, and in particular, tumor vasculature, the constituent vessels will typically vary greatly in diameter. Accordingly, a filter designed to detect relatively large vessels will not respond accordingly to small vessels, even when applied on the correct location. However, it is not known a priori where large and small vessels are located. Accordingly, successful detection may require determining the scale of the structure in the image prior to applying the filter. This technique is herein referred to as "scale detection." Scale detection may be performed on predetermined portions of an image, or may be determined on a voxel-by-voxel basis, as described in further detail below.

In addition to detecting the appropriate scale, it may be beneficial to detect the orientation in which the filter should be applied. In particular, the feature(s) being detected may appear in the image at arbitrary orientations. For example, in the case of vasculature, the vessel properties being detected may be oriented in any arbitrary direction. Accordingly, even if a filter at the appropriate scale is applied at an image region corresponding to the feature being detected, the filter response may be relatively low if it is not oriented in general alignment with the direction of the feature for which the filter was designed to detect. Accordingly, determining the orientation of the features or properties being detected may benefit filter detection techniques. This technique is herein referred to as "orientation detection."

Conventional filtering techniques combine scale and orientation detection in a single operation. That is, the combination of possible scales and orientations are tested simultaneously and the scale and orientation are selected when the response is maximum. However, Applicant has appreciated that maximum responses may not correspond to optimal scale and optimal orientation simultaneously. Because the response is a combination of scale and orientation, one or both may be sub-optimal while together providing a strong response. Applicant has developed a scale detection operation that is orientation independent. As a result, the operations of scale detection and orientation detection may be separated into two separate operations. In addition, the detected scale may then be used to improve subsequent orientation detection processes.

In act 120, scale detection is performed independently of orientation detection. In some embodiments, scale detection 120 is performed using a filter that is independent of orientation. Scale detection 120 may provide the scale in the image at different regions in the image. In some embodiments, scale detection 120 determines scale at each voxel in the image. Alternatively, a preprocessing operation may be performed to roughly determine which voxels in the image correspond to subject matter of interest (e.g., vessels) and which voxels correspond to background. Scale detection may then be performed only on pixels determined to correspond to subject matter of interest, thus reducing the amount of computations. The result of scale detection is a scale associated with each location at which the filter was applied (e.g., a scale at each selected voxel in the image). An orientation independent scale detection algorithm according to some embodiments is described in further detail below.

In act 130, orientation detection may be performed. To assist in more accurate orientation detection, the scale at the selected regions of the image determined during scale detection 120 may be provided to the orientation detection operation. As discussed above, determining the orientation of subject matter of interest in one or more images may be important for accurate filter detection of the subject matter of interest (e.g., structure, feature, property or characteristic). For example, in embodiments where the subject matter of interest is vasculature, it may be important to detect the direction of the center or longitudinal axis of the vessels before applying a filter that detects the centerline of the vessel. In some embodiments, the scale determined from scale detection 120 may be used to improve orientation detection accuracy. The result of orientation detection is an orientation or direction at each selected voxel indicating the direction of the centerline at the respective location. An orientation detection algorithm according to some embodiments is described in further detail below.

In act 140, filter detection may be performed. In filter detection 140, a filter designed to respond to the subject matter of interest in the image may be applied. In some embodiments, the filter is applied at the scale and/or orientation determined from scale detection and/or orientation detection, respectively. The magnitude of the filter response at selected locations in the image indicates the likelihood that the location includes the subject matter of interest. In some embodiments, the subject matter of interest is vasculature and the filter is designed to respond to the center of a vessel. That is, the filter may be designed to respond to the intensity profile across a vessel and thus respond most strongly when centered on a centerline voxel in the direction of the intensity profile. Because the scale and direction of the subject matter of interest has been determined at selected locations in the image, filter detection may appropriately accurate in detecting the subject matter of interest. Several methods of centerline filtering are discussed in detail below, in accordance with some embodiments of the present invention.

In act 150, non-maximal suppression may be performed on the output of the filter detection operation performed in act 140. As discussed above, the result of a filtering operation (e.g., centerline filtering) generally includes the filter response at each voxel at which the filter was applied. The magnitude of the response is typically proportional to the likelihood that the feature being detected is present at the corresponding voxel location. However, it should be appreciated that many voxel locations will have associated non-zero filter responses. In addition, some voxel locations will have associated local maximum filter responses even though the true location of the feature is elsewhere. However, accurate detection may require discriminating between local maximum and the true maximum location, which corresponds to the most likely location of the structure being detected. Non-maximal suppression 150 attempts to eliminate or suppress all but the true maximum filter responses to accurately detect the subject matter of interest. A detailed description of non-maximum suppression in the context of centerline filtering for vessel detection is described below.

In act 160, linking may be performed. Linking may include various operations that associate voxel locations with each other to form related structures so that geometric properties may be obtained from the linked voxels. For example, in the context of vessel detection, the voxel locations that were determined as centerline voxels after centerline detection and non-maximum suppression may be linked together to form the associated centerline of vessels. That is, analysis may be performed to link together centerline voxels that are likely to have arisen from the same vessel structure. In such a way, the geometry of the vessels may be obtained (e.g., geometry 15). Methods for linking voxels in the context of vessel detection are described in further detail below.

As discussed above, some embodiments are directed to detecting vasculature and extracting the geometry of the vasculature to facilitate various analysis such as diagnosis, therapeutics, drug efficacy, etc. Applicant has developed methods for extracting geometrical information from 3D volumetric images using a match filter based system to segment a vessel network and extract a mathematical (geometry) vessel representation. The geometrical representation of a vascular tree may contain data relating to three-dimensional location, orientation and/or size at any point in the vascular tree of a subject. In some embodiments, a vascular tree may be represented by a series of disks or poker chips (e.g., circular or eliptical disks) that are linked together to form a three-dimensional structure containing information relating to the local size, shape, branching, and other structural features at any point in the vascular tree.

Some embodiments of a vessel representation that employ poker chips are referred to herein as the Poker Chip representation due to the similarity to a stack of poker chips. The Poker Chip representation treats a vessel as an aggregation of infinitesimal cylinder cross-sections with continuously varying diameters. While in theory the "thickness" of each poker chip is infinitesimal, in practice the thickness of each poker chip may be related to the resolution of the image(s) from which the geometry was extracted. Thus, each poker chip may have associated geometry including, for example, center location, radius and orientation, as discussed in further detail below.

Figure 2:
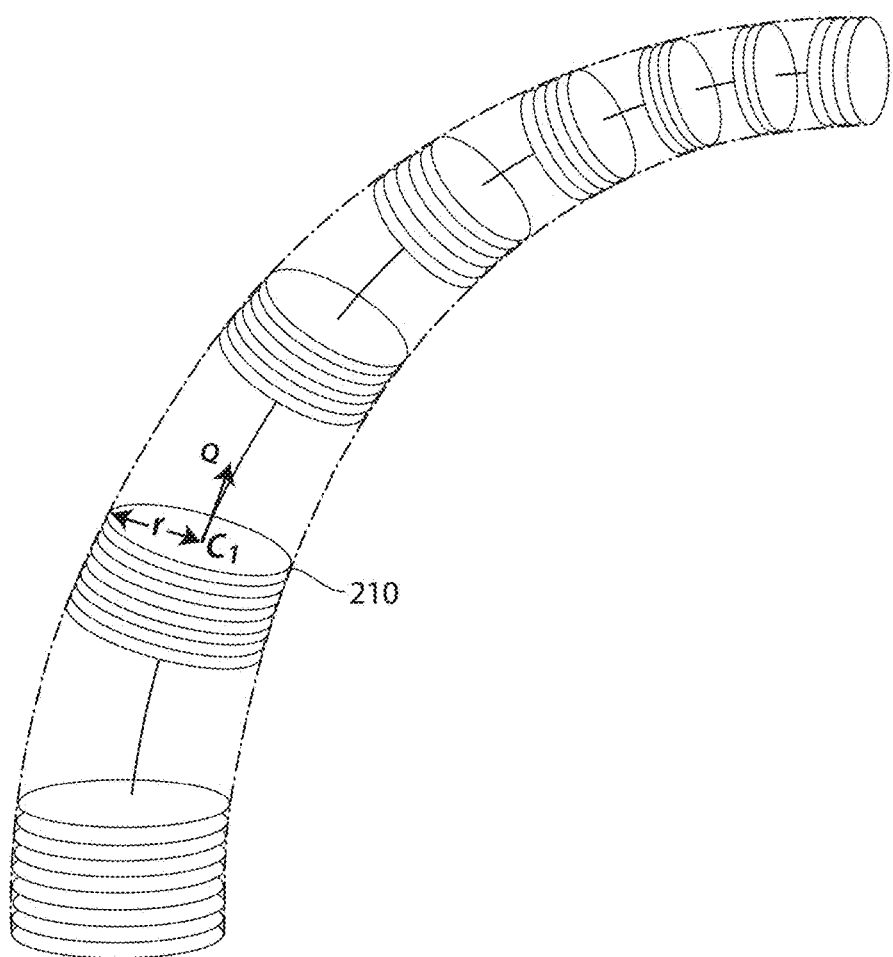
FIG. 2 illustrates a geometrical representation of vessel structure, referred to as the Poker Chip representation, in accordance with some embodiments of the present invention.

FIG. 2 illustrates a schematic of the Poker Chip representation. According to some embodiments, each poker chip 210 is defined by a center location, a radius and an orientation. The center location $c_i$ represents the center of the vessel, for example, determined by centerline filtering, as discussed in further detail below. The radius r represents the radius of the vessel at location $c_i$ and the orientation is the angle of the normal of the poker chip at location $c_i$, and represents the tangent of the centerline of the vessel at location $c_i$. It should be appreciated that the Poker Chip representation may include additional parameters, as the aspects of the invention are not limited in this respect.

Applicant has appreciated that the above Poker Chip representation may be used to determine characteristics of the vasculature that may help in diagnosing disease, providing information on appropriate treatment, and/or assessing the effectiveness of treatment. For example, since the orientation is known at each location, higher level information such as curvature and tortuosity may be computed, as well as vessel density and distribution measures, as discussed in further detail below. Additionally, since vessel diameter may be determined, vessel size and the change in vessel sizes may be computed as well. Various analyses that can be performed using the Poker Chip representation are discussed in further detail below.

To compute some of the higher order information, it may be beneficial to also include in the Poker Chip representation information about neighboring poker chips. For example, information about how the poker chips link together may be valuable in understanding the vessel structure as a whole. As discussed above, Applicant has developed algorithms that facilitate linking poker chips together to provide membership information with respect to which poker chips belong to which vessel and information regarding which poker chips are adjacent to one another. After linking has been achieved, more sophisticated vessel analysis may be performed.

Following below is a more detailed description of algorithms capable of extracting geometry from 3D images to obtain a Poker Chip representation of vasculature present in the images, in accordance with some embodiments of the present invention. While the various algorithms are discussed in connection with detecting and extracting vessel information, the concepts disclosed herein may be applied to detect and associate other structure, as the aspects of the invention are not limited in this respect. In addition, it should be appreciated that distribution analyses according to various aspects of the invention may be applied to information obtained from any vessel image, representation, or combination thereof.

Figure 3A:
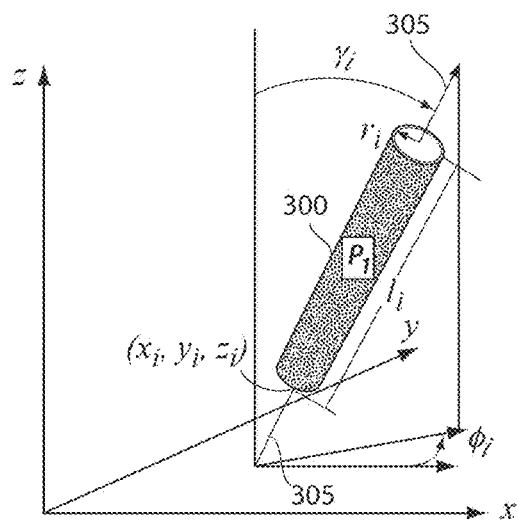
FIG. 3A illustrates a cylindrical segment used to model vessel structure, in accordance with some embodiments of the present invention.

FIG. 3A illustrates one example of a cylindrical segment 300 that may be used to generally model a vessel segment. A configuration of cylindrical segment 300 may be described by a number of parameters in a particular coordinate frame. The position of cylindrical segment 300 may be described by a location of the cylindrical axis 305 at a point $(x_i, y_i, z_i)$ in space, for example, the origin or termination of the cylindrical segment. The orientation of cylindrical segment 300 may be specified by the angle $\phi_i$ from the x-axis and the angle $\gamma_i$ from the y-axis. Since cylindrical segment 300 is axially symmetric, its rotation about the z-axis may not need to be specified. The length of the cylindrical segment may be specified by $l_i$ and the radius of the cylindrical segment 300 may be specified by $r_i$.

Figure 3B:
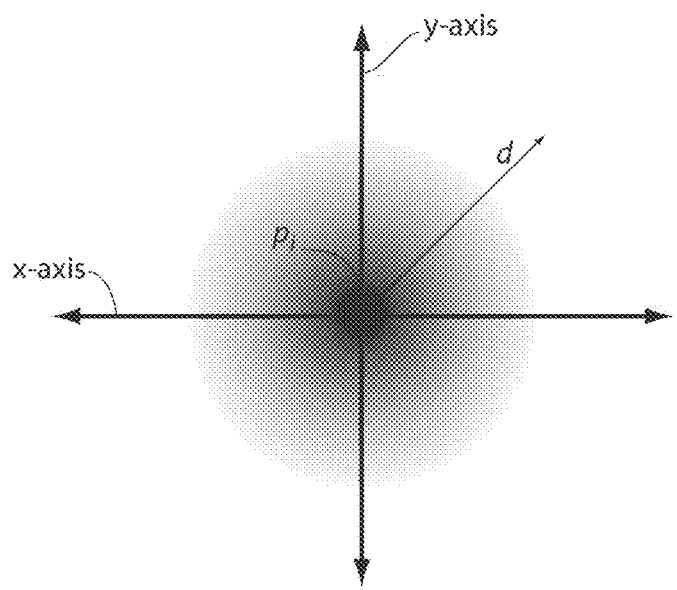
FIG. 3B illustrates a grey scale representation of a characteristic function of a model used to detect vessel structures, in accordance with some embodiments of the present invention.
Figure 3C:
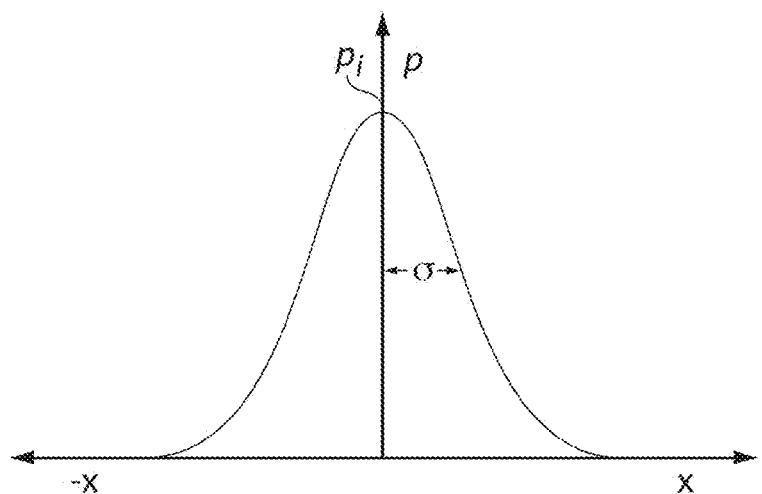
FIG. 3C illustrates a plot of the intensity values along the x-axis at the center of the grey scale Gaussian distribution in FIG. 3B.
Figure 3D:
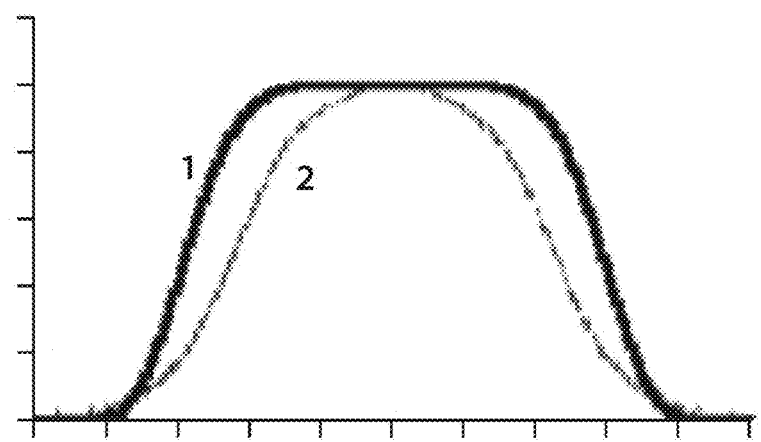
FIG. 3D illustrates a plot of the intensity values along the x-axis of another model of vessel intensity profile.

Applicant has appreciated that the cross-section of a vessel may be characterized by a generally Gaussian shaped intensity distribution. The cross-sectional density of a vessel may be modeled by a Gaussian distribution, centered on the longitudinal axis of the vessel, so that the modeled density is the highest at the center of the vessel. For example, the cross-sectional density distribution of a cylindrical vessel segment, when oriented such that its longitudinal axis coincides with the z-axis, may be modeled as, $$\rho\left(e^{-\frac{1}{r^2}((x-x_i)^2+(y-y_i)^2)}\right) \tag{1}$$

where $\rho$ is the density coefficient at a center of the cylindrical segment and r is the radius of the cylindrical segment, so that the density is modeled as being greatest at the center (i.e., equal to $\rho$) and decays exponentially as a function of radial distance from the center. FIG. 3B illustrates a grey scale representation of the function given in Eq. (1), where darker grey scale values indicate increased density values. FIG. 3C illustrates a plot of the intensity values along the x-axis at the center of the grey scale Gaussian distribution in FIG. 3B. FIG. 3D illustrates a vessel intensity profile that may better model the intensity profile of vessels in an image. Curve 1 and 2 illustrated vessel profile intensity when vessel diameter is larger than the resolution of the scan and when the vessel diameter is smaller, respectively.

Figure 4:
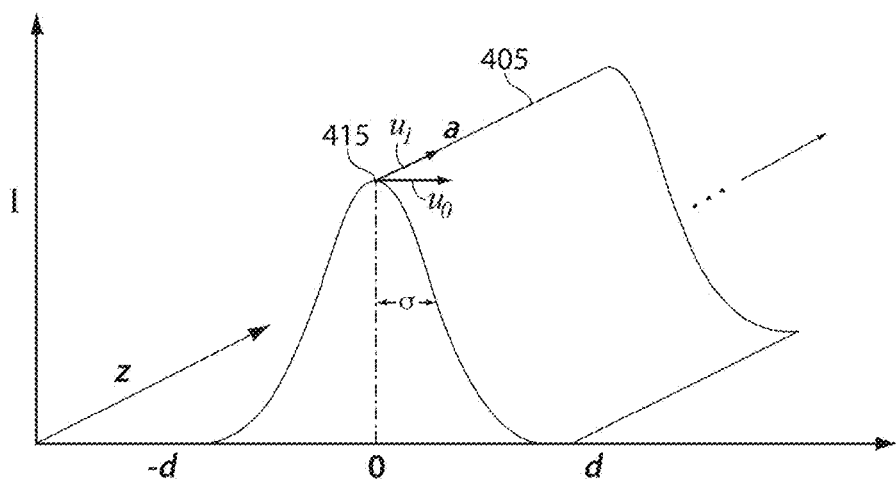
FIG. 4 illustrates schematically a cylindrical vessel segment intensity distribution illustrating a ridge or centerline feature, in accordance with some embodiments of the present invention.

The density distribution along the longitudinal axis of the cylinder (i.e., into and out of the page in FIG. 3B) is substantially uniform and does not vary substantially and may be modeled as a constant function of the cross-sectional distribution along the longitudinal axis, that is, as a constant function of the radial distance d from the center of the distribution. FIG. 4 illustrates schematically a cylindrical vessel segment intensity distribution model. In particular, the model of the cylindrical vessel segment has a maximum density at the center that decays exponentially to the boundary of the vessel as a function of the radial distance d, from the center. At each distance d, the density is uniform along the z-axis. For example, the density at d=0 is the density maximum along the length of the vessel. This density maximum shown by line 405 is referred to as a ridge, and corresponds to the centerline of a vessel.

If the herein described characteristic intensity distribution or similar distribution can be identified in the image, the associated pixels/voxels are likely to belong to a vessel. The characteristic points may be used to facilitate segmenting the image into vessel and non-vessel regions. Some methods of detecting the characteristic shape illustrated in FIG. 4 include performing ridge detection on an image. A ridge point is defined herein as a point in an image wherein the intensity assumes a local extrema in the direction of principal curvature, i.e., the direction having the steepest intensity gradient. For example, at point 415 (and along ridge 405) in FIG. 4, the principal direction of curvature is shown by $u_0$ (i.e., the unit vector (1,0) in the (d, z) coordinate frame). Each point along ridge 405 forms a ridge point since each point is a local maximum along the z-axis. Accordingly, a ridge may be characterized by local derivative information in the image and may be detected by examining the curvature of intensity about points of interest in the image.

Some conventional methods have proposed detecting the ridge using the Hessian operator. However, the Hessian operator requires performing second derivatives of the image information, which reduces the signal-to-noise ratio (SNR) and may result in degraded performance. Applicant has developed methods of detecting the characteristic shape of blood vessels described above using centerline filtering techniques that may avoid some of the performance degradations commonly seen with conventional filters such as the Hessian operator, as discussed in further detail below.

As discussed above in connection with FIG. 1, a non-limiting example of a method for extracting geometry from images may include a number of processing blocks including: a scale detector, an orientation detector, centerline filtering, non-maximum suppression and linkage. Briefly speaking, the system works as follows: firstly, the scale detection and orientation detection modules may be applied on 3D images to obtain correct size and orientation parameters for centerline detection (e.g., scale and orientation parameters for the centerline filters); secondly, based on the parameters obtained from scale detection and orientation detection modules, the centerline filter may be applied on every voxel of a 3D image, or applied on a subsection of voxels for which centerline detection is desired. The generated response field formed by applying the centerline filter indicates the likelihood that the associated voxel corresponds to the vessel centerline; finally, non-maximum suppression and linkage is applied on the centerline response field to extract the vessel centerline and obtain a vessel mathematical representation (e.g., a linked Poker Chip representation). Following below are more detailed descriptions of embodiments of the five main blocks briefly discussed above, e.g., scale detection, orientation detection, centerline filtering, non-maximum suppression and centerline linking.

Scale Detection

As discussed above, scale detection may be applied to estimate the centerline filter size appropriate for each voxel at which centerline detection is to be applied. Applying scale detection on each voxel of a 3D image volume may be relatively expensive computationally. That is, if each voxel in the 3D image is deemed to be a potential centerline point, then scale detection should be applied to each voxel in the image. However, Applicant has appreciated that since vessels occupy only a portion of the volume, it may not be necessary to detect scale on every voxel. In particular, certain voxels may be eliminated based on the image properties of the voxels, for example, the intensity level of the voxel.

In general, intensities from vessels are higher than those in the background. Using a conservative intensity threshold, voxels may be classified as background voxels with a low false positive rate that can be controlled based on how conservative the threshold operator is set. That is, by setting the threshold conservatively, a substantial percentage of the background voxels may be eliminated from scale detection without the risk of eliminating any vessel voxels. The term "background" refers herein to voxels that are not part of the subject matter of interest that is being detected. By eliminating background voxels, the computations needed to perform scale detection can be reduced. That is, by removing at least some voxels from consideration, scale detection need not be performed on each voxel in the image.

Figure 5:
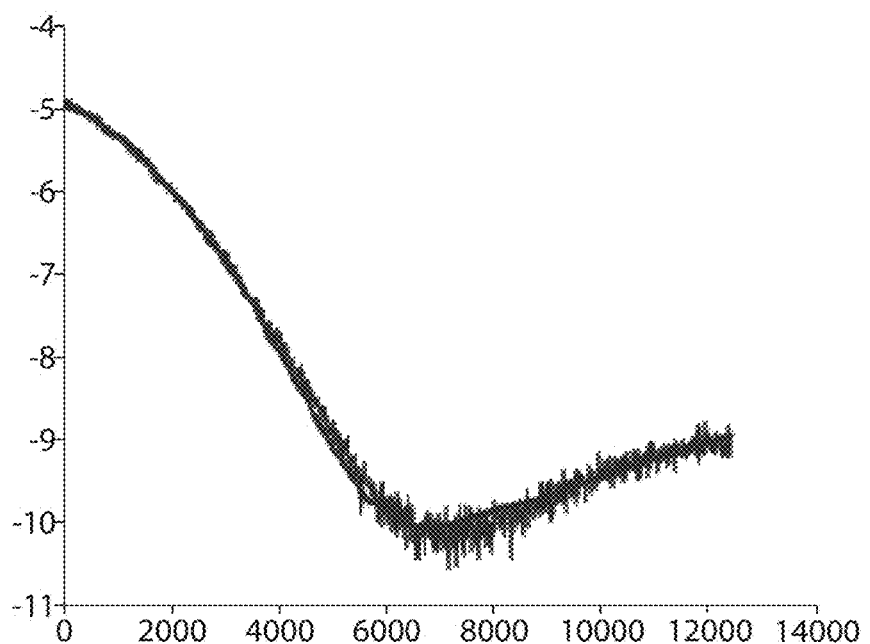
FIG. 5 illustrates an embodiment of a mixture of truncated Gaussian fit to 3D reconstruction intensity data, wherein the vertical axis is in log scale and low part of the horizontal axis is shown.

It is reasonable to model both background intensity and vessel intensities as a Gaussian distribution. In practice, the assumption in FIG. 5 shows that a model using a mixture of truncated Gaussians is a very good fit for the data in low intensity regions. The truncated Gaussian distribution has the Probability Density Function (PDF) as follows:

$$p(I/\mu, \sigma) = \frac{N(I \mid \mu, \sigma)}{\int_{b_1}^{b_2} N(x \mid \mu, \sigma) dx} \quad (2)$$

where $N(I|\mu, \sigma)$ denotes a Gaussian distribution with mean $\mu$ and variance $\sigma$, and b1 and b2 are the truncation points. To capture both background and vessel distributions, the mixture of two truncated Gaussians for the data may be expressed as:

$$p(I) = \sum_{c=0}^{1} \sum_{i} \left\{ w_c \log \left[ \frac{N_{c(I_i|\mu_c, \sigma_c)}}{\int_{b_1}^{b_2} N_{c(x_i|\mu_c, \sigma_c)} dx} \right] \right\} \quad (3)$$

where $w_c$ is the weight percentage of each component. Directly maximizing the likelihood may become challenging because determining the marginal probability may require computations that increase exponentially with the data. In some embodiments, the problem is solved using an Expectation Maximization (EM) algorithm. The EM process iteratively goes through two steps by soft assignment of data (Expectation) and maximizing the whole likelihood (Maximization). That is, an initial approximate distribution may be used to classify voxels as either background or foreground (e.g., vessels) in the Expectation step. Next, the distribution is refined based on the classification (Maximization) and classification (Expectation) is repeated on the refined distribution. This process may be repeated until the process converges on a final classification of background and foreground voxels.

Applying an EM algorithm on a mixture of Gaussians is only one method by which background voxels may be eliminated from consideration, or by which voxels are classified as background and foreground voxels. Other preprocessing or thresholding techniques may be used to reduce the number of voxels on which further processing is performed to reduce the computational expense, as the aspects of the invention are not limited in this respect. In addition, while voxel intensity may be one suitable parameter to use to perform a conservative elimination of voxels belonging to the background, any suitable parameter may be used, as the aspects of the invention are not limited in this respect. For example, higher order properties may be used.

As discussed above, separating scale detection and orientation detection may have benefits over algorithms that perform the two operations simultaneously. Applicant has designed a scale detection filter which does not depend on the orientation of the structure to be detected. According to some embodiments, an orientation independent filter may be developed such that the filter can be mathematically described in spherical coordinates as f=f(r), which is a function that does not depend on orientation. The symmetry of the filter allows the filter to be independent of how the filter is oriented. To accurately detect centerline voxels from 3D images, the response generated by the scale detection filter should be maximum when it is located at a centerline voxel. The scale $\sigma_r$ at a point (x, y, z) inside a cylinder may be defined as the distance to the wall of the cylinder boundary:

$$\sigma_r(x,y,z) = \text{dist}(x,y,z; \text{wall of the cyclinder}) \quad (4)$$

Figure 6:
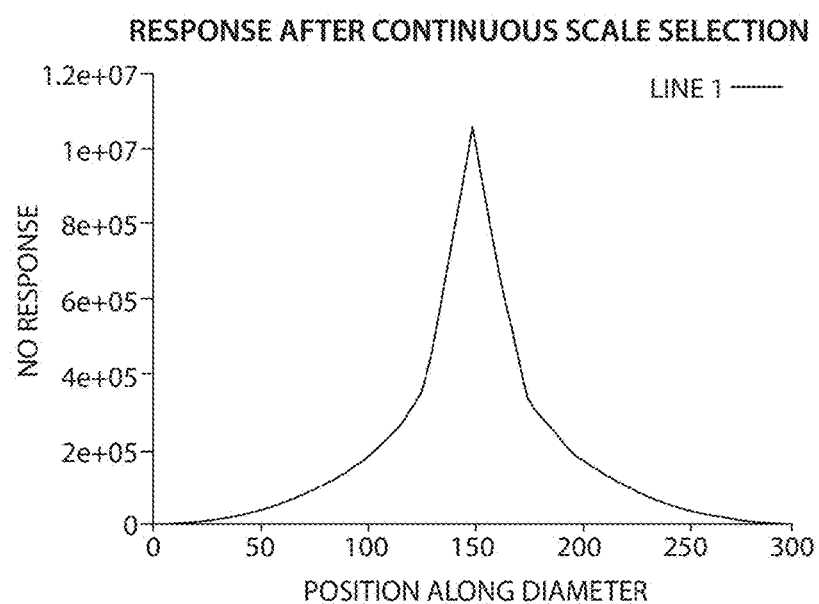
FIG. 6 illustrates an embodiment of a theoretical profile of a centerline filter response using scale detection, in accordance with some embodiments of the present invention.

As shown in FIG. 6, this definition of scale guarantees a unique maximum filter response inside the cylinder after scale selection (in the absence of noise). Normally, the intensity of a 3D image outside of a vessel is significantly lower than the intensity inside the vessel. This rapid intensity decay provides an indication of scale. Applicant has developed a rank-based scale filter that is orientation independent. Given a point X inside a vessel, a rank based scale filter may be defined as:

$$\mathcal{R}(X, r) = \frac{f_-(\{I(X'): |X' - X| = r + 1\})}{\min_r \{f_+(\{I(X'): |X' - X| = 1, \ldots, r\})\}} \quad (5)$$

where R(X, r) is the filter response at image location X with filter radius r, and $f_-$ and $f_+$ are rank functions, respectively. Note that the filter is parameterized by radius only, resulting in filter symmetry that is orientation independent. Given various noise models, there are many ways to choose the rank functions. In order to cope with image reconstruction effects, $f_-$ may be chosen as the median value of the last 10 lowest intensities and f+ may be chosen as the median value of the last 10 highest intensities. That is, the rank function may be determined from characteristics of the image. However, the rank functions may be selected to be any value that facilitates detection of scale, as the aspects of the invention are not limited in this respect. The scale $\sigma_r(X)$ may then be obtained by finding the minimum radius r so that R(X, r) reaches the threshold α:

$$\sigma_r(X) = \min_r \left\{ R(X, r) < \frac{1}{\alpha} \right\} \quad (6)$$

Stated differently, the radius of the scale filter is increased until the filter response no longer satisfies the relationship in Eq. (6). As discussed above, the scale detection filter may be designed to be independent of orientation. According to some embodiments, the kernel or shell of the scale filter is a circle in 2D and a sphere in 3D. As a result, the size of the filter is defined by the radius r, where the center of the filter is located at a target voxel at location X in the image. Since the filter has the same radius in all directions, the application of the scale filter is independent of orientation.

Figure 7:
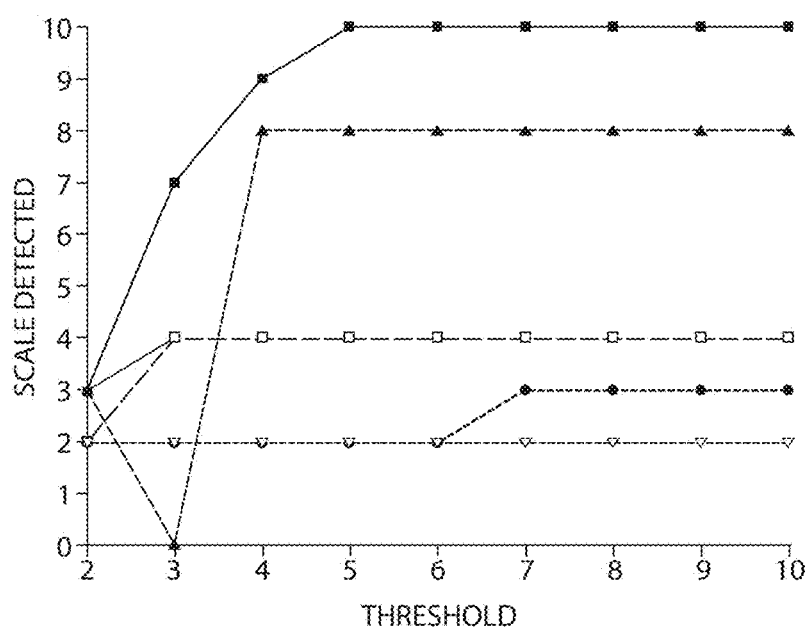
FIG. 7 illustrates an embodiment of a detected scale versus the choice of threshold α.

The criteria for the filter response may be chosen to be any suitable criteria that can robustly determine when the filter kernel has crossed a vessel boundary. The criteria in Eq. (6) is merely exemplary. In some embodiments, the value of α is chosen to be 5. However, other values may be used as well as the aspects of the invention are not limited in this respect. In order to examine the sensitivities of this rank-based scale filter to the choice of the threshold parameter α, a few points inside different vessels may be randomly chosen to see how the selected scale changes depending on the ratio threshold parameter α. FIG. 7 shows that the scale approaches the correct value when α is chosen to be larger than 5.

Figure 8:
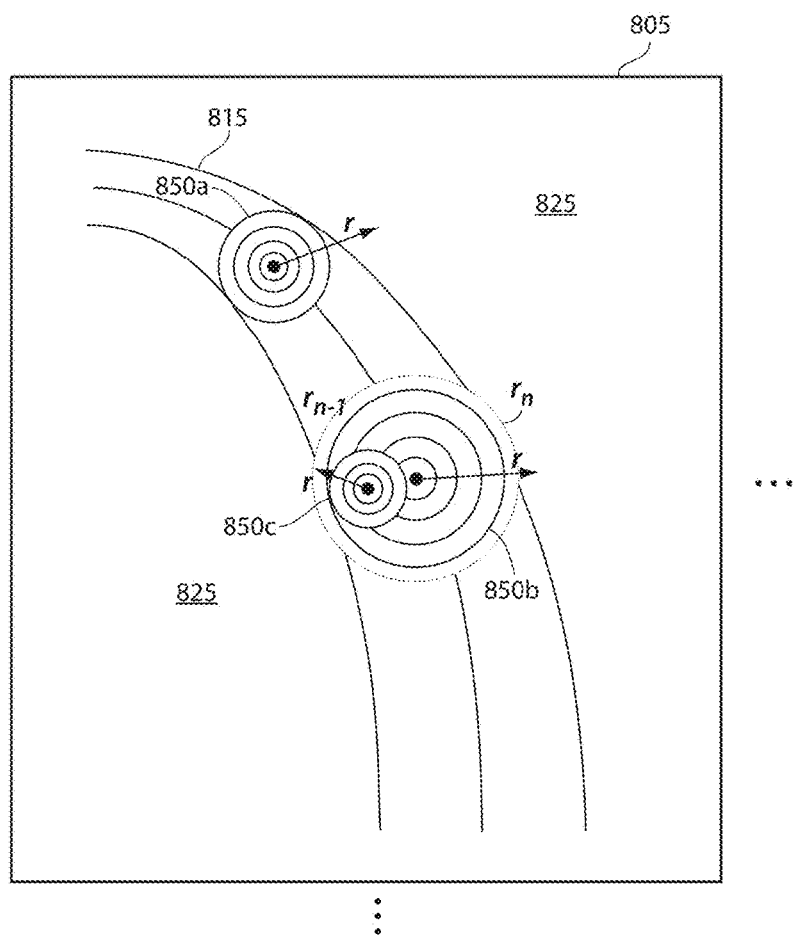
FIG. 8 illustrates pictorial an orientation independent scale filter, in accordance with some embodiments of the present invention.

FIG. 8 illustrates pictorial an orientation independent scale filter, in accordance with some embodiments of the present invention. It should be appreciated that while the scale detection filter in FIG. 8 is shown (and is suitable) in the context of a 2D image for convenience of illustration, the scale detection filter is designed as a 3D filter to detect scale in 3D volumetric images. In particular, the circular filter illustrated in FIG. 8 may be made an expanded to a sphere to detect scale in 3D. In FIG. 8, a portion of an image 805 is shown having a vessel structure 815 within the image portion. It should be appreciated that image portion 805 is schematic and the vessel structure 815 and the background 825 would be comprised of an intensity value at each voxel location in the image portion. Moreover, it should be appreciated that image portion 805 may be a small portion of a much larger image. For the sake of clarity only a single vessel structure is depicted in image portion 805, though the image portion may in reality include any number of vessel structures.

FIG. 8 also illustrates three separate applications of an orientation independent scale filter 850. It should be appreciated that the scale filter 850 may be applied at all of the image voxels or at a selected number of image voxels (e.g., voxels determined to be vessel voxels using a preprocessing techniques such as the intelligent thresholding method described above). The three applications of the filter in FIG. 8 are merely exemplary and are chosen at arbitrary locations to assist in describing the scale detection filter. Each application of the filter begins by placing the filter with a predetermined minimum radius r on a target pixel at which scale is being detected. The scale filter is then applied to the image, for example, by convolving the image pixels that fall under the filter kernel or support with the values of the filter kernel. If a certain criteria is met, the filter is assumed to still be entirely within the vessel and the radius r is increased.

In FIG. 8, the increasing of the filter radius is depicted by the successively larger circles in dashed line. The circles in solid line denote the last filter applied such that the criteria was met. For example, the dotted line circle in filter application 850b shows a circle of $r_n$ that when applied to the underlying image failed to meet the criteria, where n is the number of successively larger radius filter kernels that have been applied to the image. Thus, the scale at the corresponding image location is determined to be $r_{n-1}$. Not only does scale detection provide the appropriate scale to be used in subsequent filtering processes (e.g., centerline detection), it also may indicate the radius of the vessel structure in the Poker Chip representation.

Applicant has used the fact that the intensity of voxels within the vessel, in the absence of noise, is substantially higher than the background voxels to establish the criteria such that the criteria will not generally be met when the filter kernel is extended outside the vessel structure. One embodiment of such a criteria is described in Eq. 5 and Eq. 6. By employing the rank functions illustrated in Eq. 5, and using the criteria in Eq. 6, a robust filter may be designed that will fail to meet the criteria when the filter kernel is increased in size such that it encompasses voxels outside of the vessel. However, the above described scale detection filter is exemplary and other scale detection filters may be used, as the aspects of the invention are not limited in this respect. In addition, any criteria that tends not to be met as a filter is expanded across a vessel boundary may be used, as the aspects of the invention are not limited in this respect.

Because the centerline voxels are not known a priori, the scale detection filter may be applied to non-centerline voxels. As shown by filter application 850b, the scale detection is again stopped when the filter kernel crosses the vessel boundary. Because the target voxel is not a centerline voxel, the radius of the filter will not correspond to the radius of the vessel. However, this may be inconsequential because voxels that are not determined to be centerline voxels are removed in subsequent processing, such as during centerline filtering discussed below. Because only voxels detected as centerline voxels will survive centerline filtering, the radius of the scale detector may accurately reflect the radius of the associated vessel.

Figure 9A:
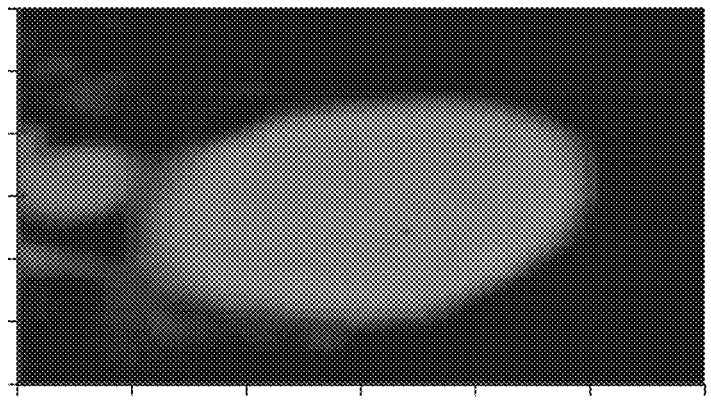
FIG. 9A illustrates an embodiment of how R(X, r) behaviors on real images, wherein a slice of 3D images is shown and blue point is the point X where we apply rank-based scale filter.
Figure 9B:
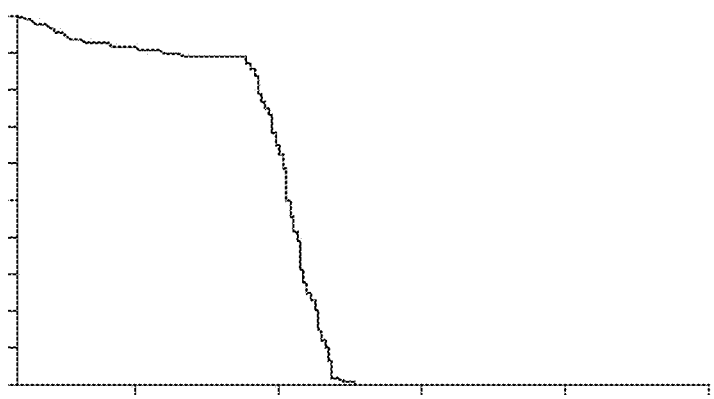
FIG. 9B illustrates an embodiment of how R(X, r) behaviors on real images, wherein the rank-based scale filter's response with different radius is shown—although the intensities have large variation inside vessel, the rank-based scale filter behavior smoothly and have a rapidly decay while cross the boundary of the vessel.

FIG. 9 shows what R(X, r) looks like when it is applied on real images. Although the intensities have large variation inside the vessel, the rank-based scale filter behaves smoothly and decays relatively rapidly across the boundary of the vessel. Thus, rank-based scale filters may have the generally beneficial property of relatively distinct response change as the filter crosses vessel boundaries, and is relatively stable and insensitive to the choice of ratio parameter. Accordingly, scale may be detected at each selected voxel in the image. For example, scale may be detected at each voxel in the image or the reduced number of voxels resulting from performing thresholding on the image to eliminate at least some of the background voxels. The selected voxels at which scale detection is performed can be selected in other ways, as the aspects of the invention are not limited in this respect.

Orientation Detection

As discussed above, centerline filtering may be improved by first determining the orientation at which the centerline filter should be applied. Since scale is detected independent of orientation, orientation detection may be performed separately from scale detection and, in some embodiments, orientation detection uses the scale values detected during scale detection to improve detection of the orientation of the subject matter of interest. In some embodiments, a gradient based orientation detection algorithm may be used, however, other algorithms may be used to detect vessel orientation, as the aspects of the invention are not limited in this respect. Because of the rotational symmetry along the axis of a cylinder on which the vessel structure may be modeled, the intensity along a line parallel to the vessel axis is constant in the absence of noise. In other words, the directional derivative of intensity along the direction v parallel to the vessel axis is zero in the absence of noise:

$$v \cdot \nabla \rho(X) = 0 \qquad (7)$$

It should be appreciated that x-ray decay during image acquisition depends on its penetrating length. Thus, the intensity inside a vessel tends to vary along any direction other than the axis direction. This fact indicates that Eq. (7) may be a necessary and sufficient condition for finding the vessel direction since the above argument holds for any point X inside the vessel. Therefore, the direction of a small cylinder segment at each point X can be estimated by finding a direction vector a along which the intensities have the least change. However, direct estimation from the derivative of one point X tends to be error prone. In some embodiments, all the derivatives inside a small volume centering on the point X may be used to increase the accuracy. To be more precise, the axis direction â may be estimated by finding a direction a that minimizes the sum of the directional intensity gradient along this direction:

$$\hat{a} = \underset{a}{\operatorname{argmin}} \left\{ \iiint_v \|a \cdot \nabla \rho(x, y, z)\| dx dy dz \right\} \qquad (8)$$

where σ(X) is the scale detected at point X and ∥·∥ is the norm discussed herein. In the presence of noise, a directional gradient of intensity convolved with an adaptive Gaussian kernel may be used, as follows.

$$\hat{a} = \underset{a}{\operatorname{argmin}} \left\{ \iiint_v \|a \cdot \nabla (G_{\sigma(x,y,z)} \circ \rho(x, y, z))\| dx dy dz \right\} \qquad (9)$$

In some embodiments, Eq. (9) can be solved by a least square estimation by assuming the noise distribution is Gaussian i.i.d, i.e., the norm in Eq. (9) is an L2-norm. However, it is well known that an L2-norm may be sensitive to outliers present in the input data, and outliers may frequently appear in reconstructed 3D images. In some embodiments, a L1-norm in Eq. (9) may be used.

$$\hat{a} = \underset{a}{\operatorname{argmin}} \left\{ \iiint_v \|a \cdot \nabla (G_{\sigma(x,y,z)} \circ \rho(x, y, z))\|_1 dx dy dz \right\} \qquad (10)$$

$$\underset{a}{\operatorname{argmin}} \left\{ \iiint_v \|a\|_1 \cdot \|\nabla (G_{\sigma(x,y,z)} \circ \rho(x, y, z))\|_1 dx dy dz \right\} \qquad (11)$$

To avoid the trivial solution at a=0 in the above equation, the constraint $\Sigma_i \|a_i\|_2 = 1$ may be used. Since a is independent of the point (x, y, z), a is moved out of the triple integral so that:

$$\hat{a} = \underset{a}{\min} \left\{ \left\| a \cdot \frac{\iiint_v \nabla (G_{\sigma(x,y,z)} \circ \rho(x, y, z)) dx dy dz}{M} \right\|_{L2} \right\} \qquad (12)$$

$$\text{s.t.} \left\{ \sum_i \|a_i\|_2 = 1 \right\}$$

It should be appreciated that in Eqs. (8)-(12), the operation is being performed over a volume v. By performing orientation detection over a neighborhood, rather than at a single voxel, semi-global information may be captured in the orientation assessment. The neighborhood information allows for robust orientation detection in the presence of noise and outliers. However, it should be appreciated that the neighborhood (e.g., the volume v) may be different for detecting direction in relatively large vessels versus relatively small vessels. Accordingly, Applicant has developed an adaptive method that varies the size of the neighborhood based on the scale at a target voxel. That is, the scale determined during scale detection may be used to determine the size of the volume v. In some embodiments, the size of $(2\lfloor s+2 \rfloor+1)$ may be used as the size of volume. However, any adaptive neighborhood based on scale may be used, as the aspects of the invention are not limited in this respect. Thus, the size of the neighborhood used for orientation detection may be adapted according to the scale of the image at each location.

As discussed above, and L1-norm may be used to address outliers. There are a number of ways to solve Eq. (12). In some embodiments, the equation is solved by constraint optimization using Lagrange multipliers. Applying Lagrange multipliers to the above equation obtains:

$$\nabla_a(a^T M^T M a + \lambda a^T a) = 0$$

$$(M^T M)a + \lambda a^T = 0 \qquad (13)$$

Therefore the center line direction, a, may be obtained by computing the eigenvector associated with the smallest eigenvalues of matrix M. Referring back to FIG. 4, solving the above equations to determine the direction a can be pictorial explained. In general terms, the eigenvectors of matrix M indicate the characteristic directions of curvature. The relationship between these characteristic directions of curvature may be employed to identify the direction of the centerline. The eigenvalues and associated eigenvectors of a matrix may be determined in various ways, for example, by any number of well known iterative methods of diagonalizing a matrix or analytically by directly solving the relationship:

$$Mu = \lambda u \qquad (14)$$

where M is the matrix of Eq. 13, u is an eigenvector of matrix M, and $\lambda$ is an eigenvalue associated with u. The magnitude of each eigenvalue of the matrix M is related to the "significance" of the associated eigenvector. Stated differently, the eigenvalue indicates how much the curvature along the associated eigenvector contributes to the local curvature determined by the matrix M. Accordingly, a in Eq. 13 is the eigenvector associated with the smallest eigenvalue and indicates the direction in which the change in intensity is the smallest. The largest eigenvalue of the matrix M is associated with the principal direction of curvature.

In FIG. 4, the linearly independent eigenvectors $u_0$ and $u_1$ (i.e., eigenvectors $u_0$ and $u_1$ are orthogonal) are shown on the illustrated intensity curve. The eigenvalue $\lambda_0$ herein denotes the eigenvalue having the greatest absolute value and is referred to as the principal eigenvalue. Accordingly, the associated eigenvector $u_0$ indicates the principal direction of curvature at a target pixel and $\lambda_0$ is related to the magnitude of the curvature. The eigenvalue $\lambda_1$ (referred to as the secondary eigenvalue) is related to the magnitude of curvature in the direction of $u_1$, i.e., in a direction orthogonal to the principal direction of curvature indicated by $u_0$. Along the ridge of the Gaussian profile (i.e., in the direction $u_1$), the intensity should be substantially zero and the change in intensity relatively small and in the noiseless case is zero (i.e., the intensity does not change as a function of z in the direction of the centerline). Accordingly, by determining the eigenvector associated with the smallest eigenvalue, the direction a which corresponds to the direction of the centerline may be determined. Thus, the orientation of the centerline may be determined at each of the selected voxels.

Centerline Detection

Having determined scale and orientation for the feature detection filter, the feature of interest may be detected. According to some embodiments, centerline detection is performed using a Gaussian centerline filter. For example, assume the density inside the vessel satisfies the Gaussian model:

$$I(r) = I_0 e^{-\frac{r^2}{2\sigma^2}} \qquad (15)$$

Here, r is in the direction perpendicular to the vessel axis; $\sigma$ is the radius of the vessel; and $I_0$ is the intensity at the center. In order to detect a Gaussian vessel, a filter with radial variation corresponding to the 2nd derivative of the Gaussian may be used:

$$h(r) = \left(\frac{r^2}{\sigma^2} - 1\right) e^{-\frac{r^2}{\sigma^2}} \qquad (16)$$

The application of this filter corresponds to a volume integral over space. This volume integral should vanish if the filter is embedded in material with constant density. However the 2nd derivative of the Gaussian does not, i.e., $$\int_0^\infty \left(\frac{r^2}{\sigma^2} - 1\right) e^{-\frac{r^2}{\sigma^2}} r\, dr = 1 \qquad (17)$$

This problem can be fixed by adding an offset, $$\int_0^\infty \left(\frac{r^2}{\sigma^2} - 2\right) e^{-\frac{r^2}{\sigma^2}} r\, dr = 0 \qquad (18)$$

Therefore, the centerline filter has the form $$f(r) = \frac{e}{4\Pi\sigma^2}\left[2 - \left[\frac{r}{\sigma}\right]^2\right] e^{-\frac{r^2}{2\sigma^2}} \qquad (19)$$

This filter has a positive core when $r<\sqrt{2}\sigma r<$ and negative shell when $r>\sqrt{2}\sigma$.

Applicant has appreciated that in the presence of noise, a centerline filter that closely mimics the shape of a Gaussian as described above may at times be inaccurate, especially in situations where vessel structures are relatively close together. In particular, the continuous decay of the Gaussian may incorrectly detect or fail to detect centerline voxels in certain situations, such as when vessel structures are close together and/or in circumstances where relatively small vessel structures appear nearby relatively large vessel structures.

Figure 10A:
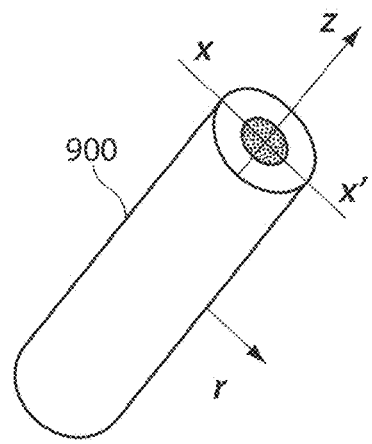
FIG. 10A illustrates a centerline filter, in accordance with some embodiments of the present invention.

Applicant has appreciated that a modified centerline filter may be more effective at accurately identifying centerline points, particularly in the presence of noise. According to some embodiments, centerline detection is performed using a filter that better matches the profile of vessel structures in an image. FIG. 10A illustrates a matched filter in accordance with some embodiments of the present invention. Filter 900 includes an inner core and an outer core. Rather than a Gaussian kernel, filter 900 includes a step function between the inner and outer core. As a result, the filter support is more compact and the filter is able to more accurately detect vessel structures that are close together. In addition, because the filter better matches vessel profiles, centerline detection may be more accurate. An example of values assigned to the matched filter 900 according to some embodiments include:

$$f_s(r, z) = \begin{cases} 1 & r \le s \text{ and } z \le \sqrt{2}\,s \\ 0 & s < r \le \sqrt{2}\,s \text{ and } z \le \sqrt{2}\,s \\ -1 & r > \sqrt{2}\,s \text{ or } z > \sqrt{2}\,s \end{cases} \quad (20)$$

Figure 10B:
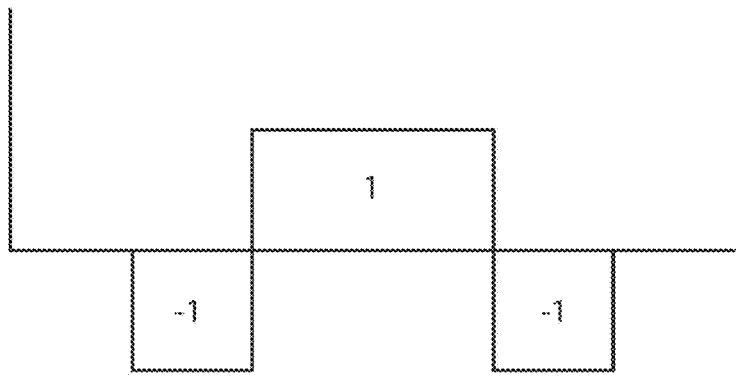
FIG. 10B illustrates a profile of the centerline filter illustrated in FIG. 9A along the line x-x', in accordance with some embodiments of the present invention.
Figure 12:
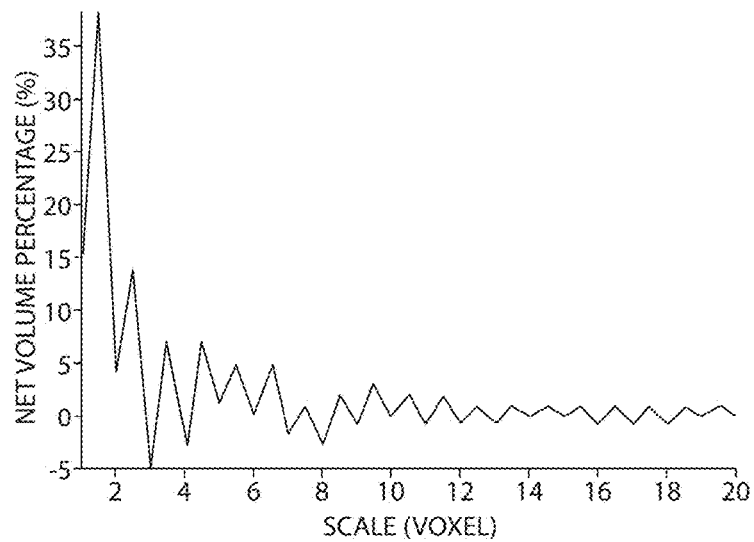
FIG. 12 illustrates net volume of the center line filter versus different scales.

An illustration of the profile of the above filter along the axis x-x' is shown pictorially in FIG. 10B. As shown, the size of the matched filter is based on the scale s detected during scale detection. Applying this filter, the centerline response may be given as:

$$r(x,y,z) = \iiint T[f(r,z)G(0,\sigma)]I(x,y,z)dxdydz \quad (21)$$

where $G(0, \sigma)$ is a Gaussian smooth kernel. When the scale of the filter is small (e.g., when scale detection determines that the local scale is relatively small), the filter defined by Eq. (20) may not have a zero net volume (volume of the positive core minus the volume of the negative core). This may cause detection difficulties because the filter may have non-zero response when applied to a non-zero uniform background. As shown in the FIG. 12, when the scale of the filter is small, the net volume percentage may be quite large. For example, for a centerline filter with scale of 1.5, the net volume is 35% of the total volume of the filter. Thus, the filter may generate filter bias in the favor of small scale.

Therefore, to address this bias the filter described above may be modified as:

$$f_s(r, z) = \begin{cases} 1 & r \le s \text{ and } z \le \sqrt{2}\,s \\ 0 & s < r \le \sigma(s) \text{ and } z \le \sqrt{2}\,\sigma(s) \\ -w_s & r > \sigma(s) \text{ or } z > \sqrt{2}\,\sigma(s) \end{cases} \quad (22)$$

where, $$\sigma(s) = \begin{cases} \sqrt{2}\,s + 0.5 & \text{if } s < 10 \\ \sqrt{2}\,s & \text{otherwise} \end{cases} \quad (23)$$

and $w_s$ is a function of scale s so that, $$\iiint_{r > \sigma(s) \text{ or } z > \sqrt{2}\sigma(s)} w_s dxdydz = \iiint_{r \le s \text{ and } z \le \sqrt{2}s} dxdydz \quad (24)$$

Figure 10C:
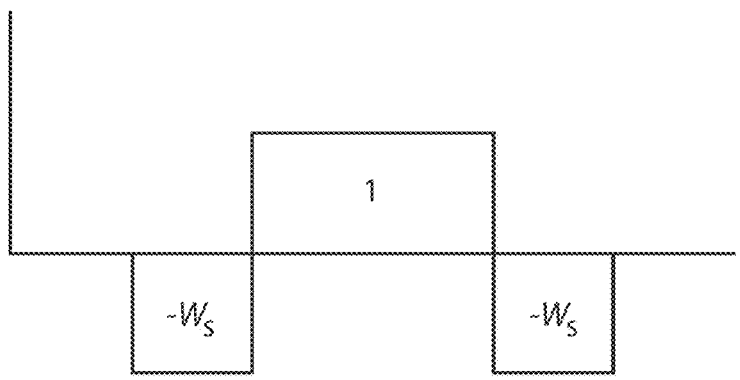
FIG. 10C illustrates another profile of the centerline filter illustrated in FIG. 9A along the line x-x', in accordance with some embodiments of the present invention.
Figure 11:
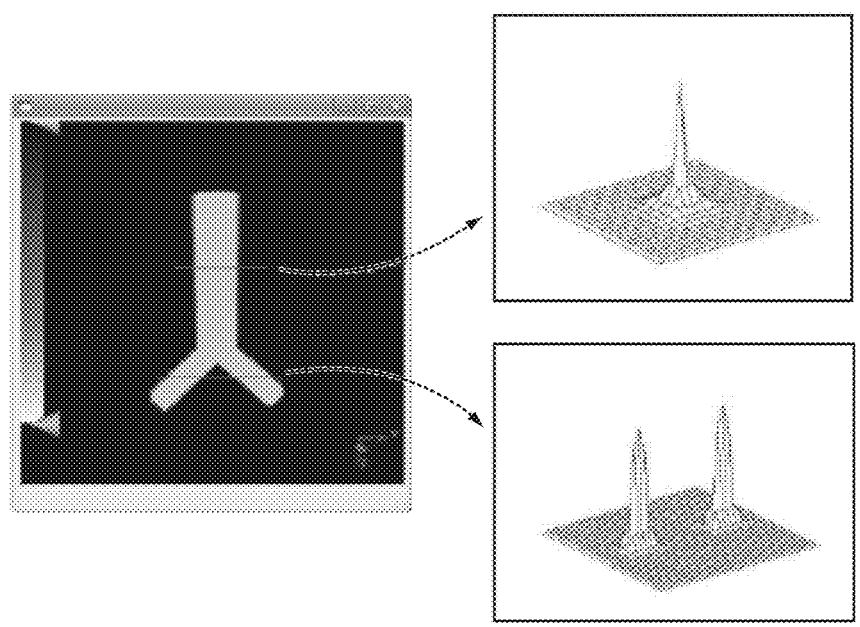
FIG. 11 illustrates centerline filtering on a 3D volume data set, in accordance with some embodiments of the present invention.

An illustration of the profile of the filter expressed in Eq. (22) along the axis x-x' is shown pictorially in FIG. 10C. The matched filters described above may be particularly effective at accurately detecting centerline voxels in the presence of noise and in circumstances when subject matter of interest is positioned in close proximity to each other.

The matched filters described above may be applied to a plurality of selected voxels in the image. Accordingly, for each selected voxel at which the matched filter is applied, there will be an associated filter response indicative of the likelihood that the corresponding voxel is a centerline voxel. However, only the maximum filter responses may be of interest. That is, the maximum filter responses are those that are most likely to be centerline voxels. Accordingly, filter responses that are not maximum may be suppressed such that only those voxels having maximum filter responses remain.

Non-Maximum Suppression

In some embodiments, non-maximum suppression may be performed. For example, after centerline filtering, each voxel has a response. The response on each voxel indicates how likely it is that the voxel is a centerline voxel. Since the center line voxel should have the maximum response in the plane perpendicular to the axis, the purpose of non-maximum suppression is to suppress non-maximum responses to eliminate non-centerline voxels. On each voxel, a cutting plane perpendicular to the vessel axis may be used to suppress the non-maximum responses. On the cutting plane, only local maximums of centerline filter responses are kept and all other responses are suppressed. Interpolating the centerline location in order to achieve sub-voxel accuracy is described below.

In some embodiments, location interpolation on the cutting plane may be performed. After obtaining the direction of the cylinder, a cutting plane perpendicular to this direction may be used to apply the non-maximum suppression as an analog to the traditional computer vision edge detection problem. Given an arbitrary voxel x, the voxel x may be tested to determine whether the voxel is a local maxima. According to some embodiments, the cutting plane may be centered on x and the centerline response R(x) may be compared with any other responses in its cutting plane neighborhood $N(x, v_x)$. That is, the response field in the neighborhood N (e.g., a 3×3×3 neighborhood) may be projected onto this cutting plane. If the response at voxel x is larger or equal to all of the responses of neighborhood voxel, voxel x may be labeled as a local maxima. Otherwise, voxel x is labeled as a non-maxima voxel and suppressed. This test may be expressed as:

$$IsMaxima(x) = \begin{cases} \text{true} & R(x) \ge R(y), \forall y \in \mathcal{N}(x, v_x) \\ \text{false} & \text{otherwise} \end{cases} \quad (25)$$

where N(x,vx) denotes the cutting plane neighborhood of the point x. Once the neighborhood is determined, the parabolic function as shown below may be used to interpolate the sub-voxel maximum location.

$$r(x,y) = ax^2 + by^2 + cxy + dx + ey + f \quad (26)$$

Given the above response model and the centerline filter responses in a small region around the center, the following equations may be used:

$$an^2 + bm^2 + cmn + dn + em + f = r(n, m) \quad (27)$$

$$a(n-1)^2 + bm^2 + cm(n-1) + d(n-1) + em + f = r(n-1, m)$$

$$\vdots \qquad \qquad \vdots$$

$$a(n-1)^2 + bm^2 + cm(n-1) - d(n-1) - em + f = r(1-n, -m)$$

$$an^2 + bm^2 + cmn - dn - em + f = r(-n, -m)$$

This linear form can be written as a matrix form $$A \begin{bmatrix} a \\ b \\ c \\ d \\ e \\ f \end{bmatrix} = \begin{bmatrix} r(n, m) \\ r(n-1, m) \\ \vdots \\ r(1-n, -m) \\ r(-n, -m) \end{bmatrix} \quad (28)$$

where $$A = \begin{bmatrix} n^2 & m^2 & mn & n & m & 1 \\ (n-1)^2 & m & m(n-1) & n-1 & m & 1 \\ \vdots & \vdots & \vdots & \vdots & \vdots & \vdots \\ n^2 & m^2 & m(n-1) & 1-n & -m & 1 \\ n^2 & m^2 & mn & -n & -m & 1 \end{bmatrix} \quad (29)$$

The maximum location is determined by the stationary condition $$\frac{\partial r}{\partial x} = \frac{\partial r}{\partial y} = 0.$$

That is, $$2ax + cy\_d = 0$$

$$cx + 2by + e = 0 \quad (30)$$

Therefore, $$\begin{bmatrix} x \\ y \end{bmatrix} = -\begin{bmatrix} 2a & c \\ c & 2b \end{bmatrix}^{-1} \begin{bmatrix} d \\ e \end{bmatrix} \quad (31)$$

$$= \frac{1}{4ab - c^2} \begin{bmatrix} -2b & c \\ c & -2a \end{bmatrix} \begin{bmatrix} d \\ e \end{bmatrix}$$

$$= \begin{bmatrix} \frac{ce - 2bd}{4ab - c^2} \\ \frac{cd - 2ae}{4ab - c^2} \end{bmatrix}$$

In some embodiments, the size of the neighborhood $N(x,vx)$ is determined based characteristics of the image in the neighborhood. There is a natural question of how big the neighborhood size should be chosen in the non-maximum suppression algorithm. In some embodiments, the smallest size of 3×3×3 may be used, but this choice may cause outliers to survive non-maximal suppression in noisy regions. An alternative method of choosing the parameter is to use the results from radius and/or scale detection. In some embodiments, to avoid suppressing real vessels which are close to each other, a conservative approach may be used when choosing the neighborhood:

$$n = 2\left\lfloor \frac{s}{\sqrt{2}} \right\rfloor = 1 \quad (32)$$

It should be appreciated that the neighborhood in Eq. (32) is exemplary and an adaptive neighborhood, for example, based on scale may be determined in other ways, as the aspects of the invention are not limited in this respect.

Linking

As discussed above, the output from centerline filtering and non-maximum suppression processes provides a 3D field in which each point is marked as either belonging to or not belonging to a centerline. In some embodiments, centerline points can be associated with other information such as radius, strength and orientation of the cylinder element (e.g., using the Poker Chip representation). The task of cylinder element linking may include connecting centerline points and identifying the junctions to generate a vessel network. In some embodiments, practical difficulties may arise associated with one or more of the following: 1) small pieces of centerline may be missing; 2) due to digitization, the centerline segments after non-maximum suppression form "zig-zags." 3) small outlier centerline segments may appear to be present due to noise where there is no real centerline; and 4) junction region may confuse the linking algorithm and lead to wrong linkages. Applicant has developed a linking method that addresses one or more of these difficulties.

In some embodiments, a local cylinder element linking algorithm may be used as follows: 1) start with a most prominent cylinder segment; 2) search in front of the cylinder segment until no more directly connected successors exist; 3) search behind the cylinder segment until no more predecessors exist; 4) mark all the connected cylinder elements; and 5) repeat the above steps until no more cylinder segments are left unmarked. An example of a linking method according to some embodiments, is described in further detail below.

A single branch of a vessel may be modeled as a digitization of a smooth, 3D curve which connects all the poker chips that belong to this branch. Given a point y that has already been selected as part of a branch (e.g., a centerline point with a large response), point y is linked to a nearby point based on a given criteria. For example, linking may be selected to prefer connecting to a point which is close to point y (distance), that does not require a large change in the expected direction $v_y$ (direction), and that has a response that is as similar to the response at point y as possible (response). Each candidate point x may be subjected to this criteria to determine which candidate is the most likely link.

According to some embodiments, the criteria is determined using a probabilistic model. For example, the above tests may be performed by finding the point x which maximizes the posterior possibility, $$Pr(L_y = x | x, v_x, r_x) \quad (33)$$

Without knowing the prior information, maximizing the posterior probability is the same as maximizing the likelihood, $$Pr(x, v_x, r_x | L = x) \quad (34)$$

If the tests of the distance, direction and response are conditional independent given $L_y = x$, it may be sufficient to provide marginal distribution for each tests.

$$Pr(x, v_x, R_x | L_y = x) = Pr(dist(x, y), \vec{xy}, R_y | L_y = x) \quad (35)$$

$$= Pr(dist(x, y) | L_y(x, y), \vec{xy})Pr(\vec{xy} | L(x, y))$$

$$Pr(r_y | L(x, y))$$

$$= Pr(dist(x, y) | x)Pr(\vec{xy} | v_x)$$

$$Pr(R_y, s_x | R_x, s_y) \quad (7)$$

Among the three tests defined above, Applicant has determined that distance tends to be the most reliable. Therefore, it is possible to build a probability model for this distance test. According to some embodiments, a Gaussian model is chosen for the distance test to penalize the distance between point y and candidate x exponentially:

$$Pr(dist(x, y) | x) = \frac{1}{\sqrt{2\pi}} \exp\left(-\frac{|x-y|^2}{2}\right) \quad (36)$$

As discussed above, another useful test is determining the extent of direction change in the linked centerline points (e.g., as determined from orientation detection) that would be incurred by linking point y with candidate point x. However, Applicant has appreciated that the direction of the centerline from the orientation detection may zig-zag locally due to digitization. Therefore, relying entirely on the direction obtained from the orientation detection may lead to linking errors. To address this difficulty, some embodiments employ a super Gaussian model to test the possibility of connecting point y with candidate x, given the centerline direction of point x.

$$Pr(\vec{xy} | v_x) = \frac{1}{Z} \exp\left(-\frac{\theta(\vec{xy}, v_x)^4}{\sigma^4}\right) \quad (37)$$

The super Gaussian model has a flat top which allows the test to tolerate relatively large angle variation. As discussed above, the centerline response and scale may also be used to test the viability of linking point y with candidate x. It is reasonable to assume that the centerline responses and scale are smoothly changing along a single branch. In the other words, linking to a point which causes centerline to rapidly change may be assigned a low probability. With this intuition, a response test model may be constructed as follows:

$$Pr(R_y, s_y | R_x, s_x) = Pr(s_y|R_x, s_x)Pr(R_y|R_x, s_x, s_y) \quad (38)$$
$$= Pr(s_y|s_x)Pr(R_y|s_y, R_x, s_x)$$
$$= \frac{1}{Z}\exp\left(-\frac{(s-s_x)^2}{2\sigma_s^2(s)}\right)\exp\left(-\frac{\left(\frac{R_y}{s_y^3} - \frac{R_x}{s_x^3}\right)^2}{2\sigma_r^2}\right)$$

where Z is the normalization factor, $\sigma_s(s)=\max\{0.5, 0.2 s\}$. Thus, the above test may be employed in connection with the algorithm described above to link the centerline points (e.g., the centerline points that survived non-maximum suppression). Due to errors in the direction finder and grid discretization, some non-centerline points survive from non-maximum suppression. However, the number of those points may be reduced by applying an occupancy constraint. The occupancy constraints operate on the notion that if a local space is occupied by a previously linked branch, then it is not likely possible to be the center of another branch. In the other words, a high confidence may be assigned to long branches to suppress weak branches, if the weak branch occupies the same space as the strong branch.

As a result of linking the centerline points together, each of which represents a poker chip having a center location (the centerline point), a radius and a direction of the centerline at the center location, further geometry of the vessel may be computed. Referring back to the schematic of the Poker Chip representation in FIG. 2. Having computed each of the center location $c_i$, the radius r and the orientation a, and having linked the adjacent poker chips, additional geometry of the blood vessels may be determined. For example, the linked orientation parameters capture information about the geometry of the centerline. For example, by integrating the orientation vectors, the centerline curve may be obtained. That is, because the orientation vectors represent the tangents of the centerline curve at each location $c_i$, the centerline curve may be recovered from linked tangents by integrating over some desired segment of poker chips.

Figure 13:
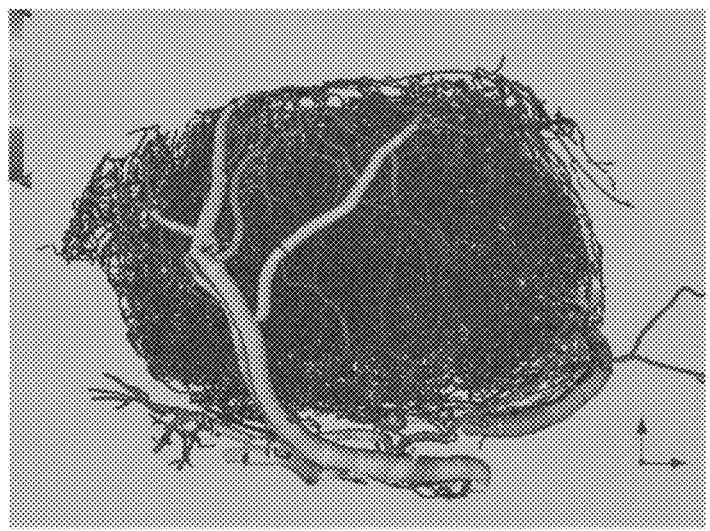
FIG. 13 illustrates a geometrical representation of vasculature obtained from a 3D volumetric image, in accordance with some embodiments of the present invention.

In addition, the linked poker chips may be used to determine higher order and/or more sophisticated geometrical properties. For example, derivatives of the linked orientation vectors may be used to determine the curvature of the vessel. The centerline curve, length of the curve and curvature parameters may be used to determine various tortuosity parameters, which may be used to characterize the vessels. Moreover, the Poker Chip representation carries distribution information with respective to the density of vessel material, the relative distribution of vessels at different radii, etc. These geometrical, structural and distribution parameters may be used in a number of ways to analyze vasculature, as discussed in further detail below. FIG. 13 illustrates a geometrical representation of vasculature using the linked Poker Chip representation, wherein the geometry was extracted from a 3D volumetric image using the methods described herein.

According to some embodiments, the linking algorithm may be performed in parallel. Since linking is generally local and may not need to rely on the information from far away voxels, the algorithm can be parallelized by dividing the image into small blocks. Then individual CPUs may operate on a single block without the need to communicate with other blocks. Because of the computation requires some neighborhood information, each block may include a fixed margin overlapping with its neighbor's margin. The speed gained by parallelization is the number of processors divided by one plus overhead caused by margin. In one example, dividing a volume of 2000×2000×1400 into 500× 500×500 blocks and using 8 processors produced a gain of 4.49 times processing speed.

The margin for parallelization may be chosen based on the following: 1) the margin for the scale selection $m_s = r_{max}+1$; 2) the margin for the smoothing $m_{sm}=3\sigma$, 3) the margin for the gradient computation $mg=1$; 4) the margin for the direction detection $m_d=m_g+r_{max}+1+m_{sm}$; 5) the margin for centerline filtering $m_c = \max\{2r_{max}, m_d\}$; and 6) the margin for the non-maximum suppression $m_{sprs}=r_{max}+m_c$.

Because the block algorithm for parallelization needs to divide the volume into blocks at beginning and assembling the blocks into a volume at the end, away to transform between global coordinates and block coordinates may be needed. The block id $(b_x, b_y, b_z)$ for a point (i, j, k) in the global coordinate is given as:

$$b_x = \left\lfloor \frac{i}{s} \right\rfloor \quad (39)$$
$$b_y = \left\lfloor \frac{j}{s} \right\rfloor$$
$$b_z = \left\lfloor \frac{k}{s} \right\rfloor$$

The local coordinates in its block is (i', j', k')

$i'=i-b_x s$ $j'=j-b_y s$ $k'=k-b_z s \quad (40)$

The dimension ($s_x$, $s_y$, $s_z$) of the block ($b_x$, $b_y$, $b_z$, b) is:

$$s_x(b_x) = \begin{cases} \mod(N_x, s) & \text{if } b_x = \left\lfloor \frac{N_x}{s} \right\rfloor - 1 \wedge \left\lfloor \frac{N_x}{s} \right\rfloor \neq 0 \\ 0 & \text{if } b_x < 0 \\ s & \text{otherwise} \end{cases} \quad (41)$$

$$s_y(b_y) = \begin{cases} \mod(N_y, s) & \text{if } b_y = \left\lfloor \frac{N_y}{s} \right\rfloor - 1 \wedge \left\lfloor \frac{N_z}{s} \right\rfloor \neq 0 \\ 0 & \text{if } b_y < 0 \\ s & \text{otherwise} \end{cases}$$

$$s_z(b_z) = \begin{cases} \mod(N_y, s) & \text{if } b_z = \left\lfloor \frac{N_z}{s} \right\rfloor - 1 \wedge \left\lfloor \frac{N_x}{s} \right\rfloor \neq 0 \\ 0 & \text{if } b_z < 0 \\ s & \text{otherwise} \end{cases}$$

Given a point (i', j', k') at block ($b_x$, $b_y$, $b_z$, b), the global offset in the file is:

$$pos = i' s_y s_z + j' s_z + k' + \underbrace{\begin{pmatrix} b_z N_x N_y s_z(b_z - 1) + \\ b_y N_x s_y(b_y - 1) s_z(b_z) + b_x s_x(b_x - 1) s_y(b_y) s_z(b_z) \end{pmatrix}}_{\text{block offset}} \quad (42)$$

The number of blocks in the x dimension is $$n_{bx} = \left\lceil \frac{N_x}{s} \right\rceil,$$

the number of block in the y dimension is $$n_{by} = \left\lceil \frac{N_y}{s} \right\rceil$$

and the number of blocks in the z dimension is $$n_{bz} = \left\lceil \frac{N_z}{s} \right\rceil,$$

A one dimensional block ID $1=(1, \ldots, n_{bx}n_{by}n_{bz})$ to 3D index $$b_x = \left\lfloor \frac{l}{n_{by}n_{bz}} \right\rfloor \quad (43)$$

$$b_y = \left\lfloor \frac{l \ldots b_x n_{by} n_{bz}}{n_{bz}} \right\rfloor$$

$$b_z = l - b_y \; n_{bz} - b_x n_{by} n_{bz}$$

Three dimensional block ID ($b_x$, $b_y$, $b_z$) to one dimensional block ID.

As discussed above, the linked Poker Chip representation may be used to determine a number of geometrical and structural parameters of the vasculature, and also may be used to determine distribution information of the vasculature. Provided herein is a description of methods that utilize the extracted geometry to analyze the vasculature for diagnostic, treatment efficacy assessment, therapeutic, and other applications, or any combination thereof.

II. Determination of a Boundary of Region(s) of Interest of a Vascular

As discussed above, having the ability to determine the boundary of at least a portion of a vascular network of interest may provide a valuable tool for medical diagnostic, prognostic, and/or research applications including, but not limited to, analyzing structures such as blood vessels and the morphological attributes of a bounded vascular network to evaluate their association with disease, responsiveness to therapeutic treatments, and/or other conditions. Subsequent to obtaining a geometric representation of a vascular network, the vessel geometry may be used to determine a boundary of at least a portion of the vascular network. A boundary may define the vasculature of a particular organ, a tumor or any other portion of a vascular network of interest. Techniques described herein may be used to bound an organ and also to bound a region (e.g., a tumor) within the organ, as the aspects of the invention are not limited for use with any particular type of vasculature.

Figure 14:
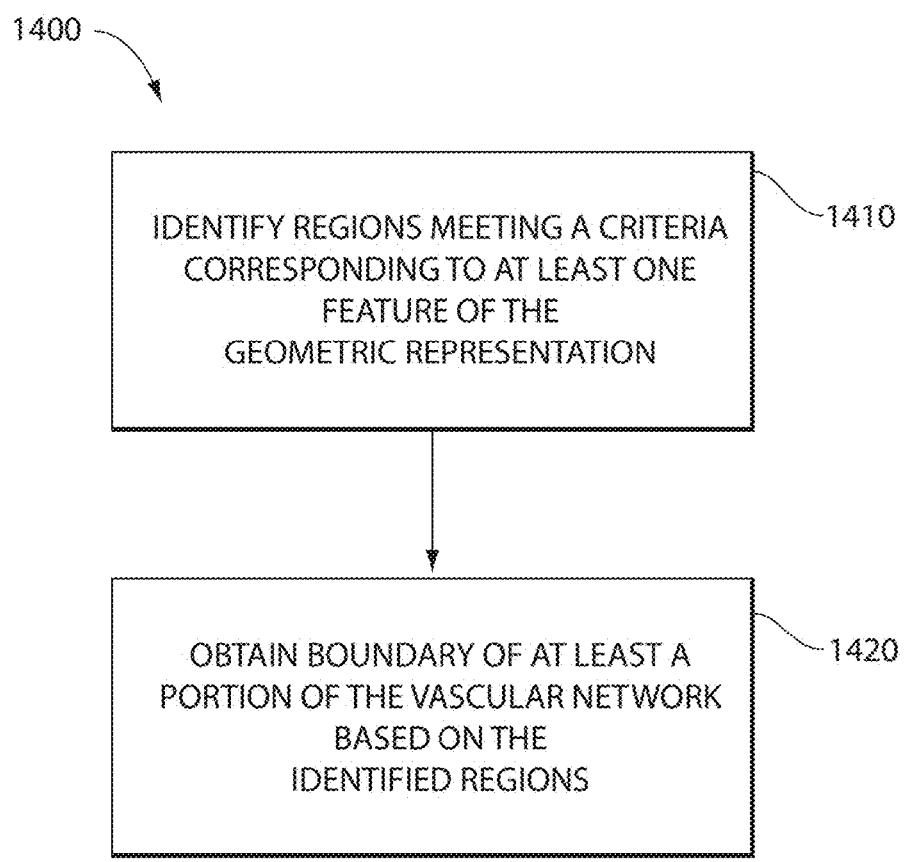
FIG. 14 illustrates a method of determining a boundary for a portion of a geometric representation of vasculature.

FIG. 14 illustrates a method of identifying the boundary of at least a portion of a vascular network, in accordance with some embodiments. For example, method 1400 may be performed on a geometric representation of a vascular network obtained using any of the techniques described in the foregoing or using any other suitable technique, as the aspects of the invention are not limited for use with geometric representations obtained in any particular way. Moreover, method 1400 may be applied to a previously obtained geometric representation that was stored locally or remotely or transmitted from another location. The geometric representation may be obtained from images or generated by other means, as the aspects of the invention are not limited in this respect.

In act 1410, regions of the geometric representation are evaluated and those regions that meet a selected criteria are identified. The criteria may be any measure(s) corresponding to one or more features of the geometric representation of the vascular network. Suitable criteria may include any one or more measures that can distinguish between vessels within the portion of the vascular network of interest and vessels outside the portion of the vascular network of interest. As an example, Applicant has appreciated that vessels that are part of a tumor region may have characteristics that distinguish the tumor vessels from vessels that are not part of a tumor region (e.g., that distinguish between tumor vessels and vessels associated with healthy tissue). That is, tumor vasculature may have vessel structure that is different from normal or healthy vasculature such that the vessels of the tumor vasculature can be bounded (also referred to herein as "wrapped"). Similarly, vessels within an organ of interest may have one or more defining characteristics that assist in defining a boundary between vasculature within a desired organ and those outside of the organ. With a boundary defined, further analysis may be performed on the bounded vasculature, as discussed in further detail below. It should be appreciated from the foregoing that any distinguishing morphological feature of the geometric representation may used to facilitate defining a boundary of the portion of the vascular network that is of interest.

As discussed above, the criteria may include any one or combination of vessel features of the vessel geometry that facilitates distinguishing between vessels within the vasculature of interest and vessels outside the vasculature of interest. For example, vessel density may be one feature of vessel geometry capable of distinguishing a boundary of a portion of a vasculature. According, to some embodiments, the Poker Chip representation may be used to compute vessel density. For example, the number of Poker Chips per defined volume may be computed as a measure of vessel density. The vessel density may then be converted into a three-dimensional (3D) scalar field to assist in identifying a boundary of the vasculature of interest, as discussed in further detail below. Other measures besides (or in addition to) vessel density may be used to facilitate boundary identification, as the aspects of the invention are not limited for use with any particular feature or morphological attribute.

As discussed above, the Poker Chip representation may be further processed to incorporate higher order information such as how the poker chips are linked together to form the vessels in the vascular network. The information obtainable via linking the poker chips together may be used as a measure, either alone or in combination, to distinguish vessels of interest (e.g., to distinguish between healthy and diseased vessels, vessels belonging to a specific organ, or both). Link information may be used to obtain information related to how often vessels branch within a vascular network. Branch frequency may then be used to distinguish between vessels and assist in defining a boundary of the vasculature of interest. For example, the number of vessel branches per predetermined volume may be used as a feature to facilitate determining the boundary of a portion of a vascular network.

Other higher order features may also be used. Link information may provide information as to morphological attributes such as curvature and tortuosity. These measures may also be used to facilitate boundary determination. For example, some criteria may be established based on curvature and/or tortuousity and the geometric representation may be converted to a 3D scalar field based on regions that meet the criteria and regions that do not. Similarly, vessel orientation, vessel length, vessel diameter or any other vessel geometry measure for which a suitable criteria can be established that distinguishes vessels that belong to a desired portion of a vascular network may be used to facilitate determining a boundary either alone or in any combination, as discussed in further detail below.

In act 1420, the identified regions are used to define a boundary of at least a portion of the vascular network of interest. According to some embodiments, a selected one or combination of features suitable in distinguishing a portion of a vascular network is used to convert the geometric representation of the vascular network to a 3D scalar field representation based on whether regions of the geometric representation meet a predetermined criteria. That is, the geometric representation may be logically divided into volumes of a desired size. Each volume may be evaluated according to a given function of at least one feature of the geometric representation. For example, each volume may be assigned one or more values according to the evaluation function and compared to a designated criteria. According to some embodiments, the conversion illustrated in equation 44 may be used to convert the geometric representation of the vascular network to a 3D scalar field representation of the vascular network.

$$\phi_0(x, y, z) = \begin{cases} 0 & \text{if } F(G) \text{ meets } C \\ 1 & \text{Otherwise} \end{cases} \quad (44)$$

Where F is a function of the geometric representation G and C is a desired criteria. According to the 3D scalar field representation, the vascular network is represented as a binary function $\phi(x, y, z)$, where regions (e.g., predetermined volumes) that meet a given criteria are assigned a value of zero. As discussed above, the geometric representation may be logically divided into volumes of a desired size. Each volume may be evaluated according to a given function of at least one feature of the geometric representation. For example, each volume may be assigned one or more values according to the evaluation function and compared to a particular criteria. The resulting representation may be binarized to separate volumes that meet a criteria and volumes that do not.

As shown by equation 44, the criteria C may be defined as any criteria suitable for distinguishing between vessel structures inside and outside a portion of the vascular network of interest (e.g., vessels within and without the boundary of the portion of the vascular network of interest). Likewise, the function F may be any function of the geometric representation of the geometric representation G. Accordingly, by evaluating F(G) over the domain of the geometric representation of the vascular network and comparing the evaluation to the criteria C, the geometric representation may be converted into a 3D scalar field representation.

Figure 15:
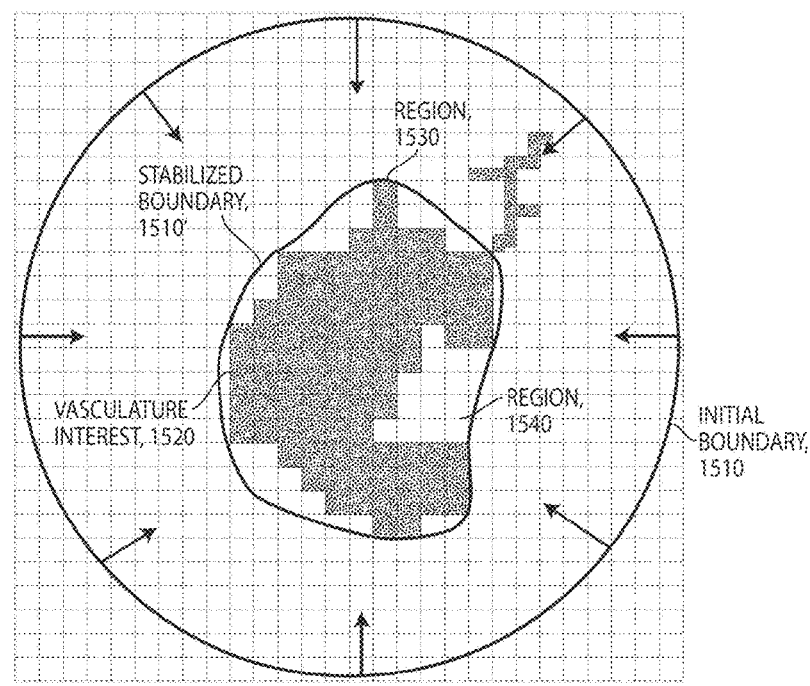
FIG. 15 is a schematic of boundary evolution over a 2D scalar field representation.

It should be appreciated that any function may be evaluated and compared to any criteria, such that any one or combination of features of the vessel geometry may be used to convert the geometric representation to a 3D scalar field, which in turn may be further processed to identify the boundary, as discussed in further detail below. FIG. 15 illustrates a 2D cross-section of a 3D scalar field representation. In FIG. 15, the areas denoted as black are regions in which the corresponding one or more features of the vessel geometry that were evaluated meet the predetermined criteria. For example, the black regions may indicate portions of the geometric representation of a vascular network in which the vessel density exceeds a desired threshold. However, the black regions may denote portions of the vessel geometry wherein any one or more geometric features meet a predetermined criteria, as the aspects of the invention are not limited for use with any particular feature or combination of features of the vessel geometry.

Applicant has appreciated that the density of one or more features of the vessel geometry may be a useful measure in identifying the boundary of a vessel network. That is, the function F may be a density function $\rho$ such that equation 44 can be expressed as:

$$\phi_0(x, y, z) = \begin{cases} 0 & \text{if } (\rho(x, y, z) > T) \\ 1 & \text{otherwise} \end{cases} \quad (45)$$

Where $\rho$ is the density of one or more features of the geometry of the vessel network and T is a desired threshold. According to some embodiments, the density may be vessel density, branching density/frequency, binned vessel density (e.g., vessel density of vessels having a desired range of diameters), etc. The function $\rho(x,y,z)$ may be evaluated over each location (e.g., logically defined volumes over the domain of the geometric representation) in the geometric representation and compared with the threshold T. Locations having densities that exceed threshold T may be assigned the scalar value 0 and all other locations assigned the scalar value 1. It should be appreciated that whether locations that meet or do not meet the criteria are assigned 0 or 1, respectively, is arbitrary and the values may be switched or any scalar values may be used (e.g., the 3D scalar field representation need not be binary). Once a 3D scalar field representation based upon a given function and criteria (e.g., ρ(x,y,z) and threshold T) is generated, the 3D scalar field representation may be further processed to determine the boundary.

It should be appreciated that since all functions and criteria may be converted into the same scalar field representation, the boundary may be determined by processing the resulting scalar field representation in generally the same fashion regardless of what function/criteria was used to generate the scalar field representation. As a result, the following techniques may be applied to any scalar field representation to identify the boundary independent of the choice of function/criteria used in the converting the geometric representation of the vascular network to a 3D scalar field representation.

Techniques for identifying the boundary from a 3D scalar representation may include representing the boundary as an implicit surface by ϕ(x, y, z)=0 and using level set techniques that progress according to a partial differential equation (PDE) that informs how a surface evolves. According to some embodiments, the PDE may characterize principles analogous to heat diffusion/divergence to locate the boundary. For example, the 3D scalar field ϕ(x, y, z) may be treated as a temperature field with ϕ-values between 0 to 1. It should be appreciated that the domain [0,1] is arbitrary and any other domains may be used. As shown in equation 44, the ϕ-value may be fixed at identified regions to be zero and at the boundary of the entire scalar field to one. In the other words, identified regions are the heat sink and boundary of the whole region is the heat source. For example, assume ϕ is a temperature field which is initialized as shown in equation 44. Once initialized, ϕ may be propagated according to a partial differential equation (PDE), some embodiments of which may be expressed as, $$\frac{\partial \phi}{\partial t} = -\nabla(v\phi - \gamma \nabla \phi) \quad (46)$$

Which characterizes temperature changes due to divergence of heat flux plus heat diffusion, where the velocity vector v may be expressed as, $$v = \alpha \frac{\nabla \phi}{|\nabla \phi|} - \beta \nabla \left( \frac{\nabla \phi}{|\nabla \phi|} \right) \frac{\nabla \phi}{|\nabla \phi|} \quad (47)$$

The first term controls the behavior of the boundary when there is no change in the conditions at location x, y, z (e.g., when the boundary is not encountering a region labeled as zero). For example, the first term may represent a uniform speed of the heat flux along the normal direction of ϕ-field. The second term controls how the boundary behaves in regions of curvature. According to some embodiments, α is chosen to be unity such that the boundary progresses at a constant velocity when no temperature change is encountered. However, α may be assigned any value (or may be a user selectable variable), as the aspects of the invention are not limited in this respect. The negative sign preceding the parameter β establishes curvature direction so that convex parts move in and concave parts move out. β may be selected to achieve a desired behavior in the presence of curvature, as discussed in further detail below.

The final term in equation 46 controls the smoothness of the boundary. The term can be viewed as a diffusion term that prohibits the heat field to change rapidly so that the boundary smoothly transitions between gaps to prevent holes from forming (e.g., the final term operates to fill in holes that may be present in the 3D scalar field representation so that a smooth, continuous boundary may be achieved). The γ parameter controls the level of "viscosity" of the boundary and may be selected to achieve a desired performance, as discussed in further detail below. After the boundary is initialized, the boundary may be evolved according to equation 46 until ϕ is stabilized and/or a desired number of iterations have been performed. During evolution, locations having a zero value remain zero.

FIG. 15 illustrates a schematic of a boundary applied to a 2D scalar field representation of a portion of a schematic vasculature network both at initialization (1510) and after the boundary has stabilized (1510'). It should be appreciated that the 2D scalar field is shown for convenience of illustration and while techniques described herein may be applied in two dimensions, three dimensional vascular analysis is preferred to support full three dimensional vascular analysis. As discussed above, black regions in FIG. 15 (e.g., regions labeled with a zero scalar value) denote portions of a geometric representation of a vascular network evaluated according to a particular function of the vessel geometry that meet a designated criteria. For example, the black regions may denote portions of the geometric representation having a vessel density (e.g., number of poker chips per volume) that exceed a designated threshold. However, as discussed above, the black portions may denote regions of the geometric representation that evaluate according to any function to meet any criteria, as the aspects of the invention are not limited in this respect (e.g., branch density, vessel curvature or tortuosity, vessel orientation, vessel length, etc).

The initial boundary 1510 is applied to the 2D scalar field representation such that the boundary initially over-encompasses the vasculature of interest (e.g., the boundary may be initialized such that it encompasses the entire geometric representation of the vascular network). The boundary may then be evolved in the direction indicated by the arrows (as controlled by the first term and α) until the boundary stabilizes as shown schematically by final boundary 1510'. As shown, the final boundary encloses the vasculature of interest 1520 (e.g., a tumor) relatively closely without breaks or holes. In 3D, the boundary forms a volume containing the vasculature of interest and defines which regions are inside the boundary and which regions are outside the boundary. Preferably, the 3D boundary is a closed or substantially closed volume enclosing the vasculature of interest.

As discussed above, the first term causes the boundary to evolve inwards in the direction of the arrows. The second term describes how the boundary penalizes high curvature. For example, the second term causes the boundary to slow down in regions of high convex curvature so that the boundary does not evolve past such regions such that relatively high curvature regions like region 1540 is enclosed by the boundary due to the operation of the second term. The third term provides a smoothness constraint on the boundary. For example, the third term prevents the boundary from entering region 1540 by requiring that the smoothness constraint be met. It should be appreciated that γ may be chosen (or presented as a user selectable variable) to achieve a desired smoothness and/or ensure that holes/gaps of certain sizes are filled, as discussed in further detail below.

Figure 16A:
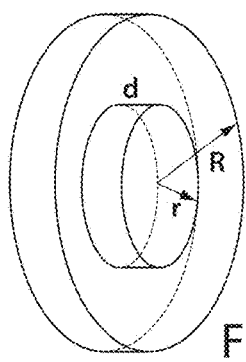
FIG. 16A illustrates a disc having a hole in the center having a thickness d, radius R and a hole having a radius r.
Figure 16B:
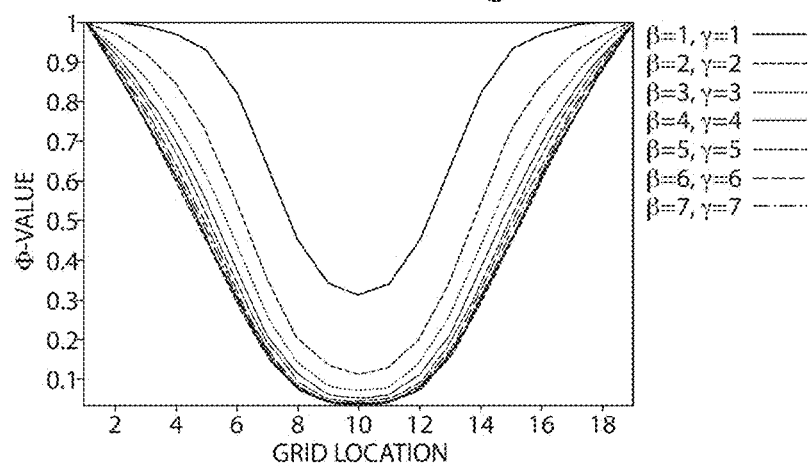
FIG. 16B illustrates selection of β and γ parameters to achieve desired boundary behavior.
Figure 16C:
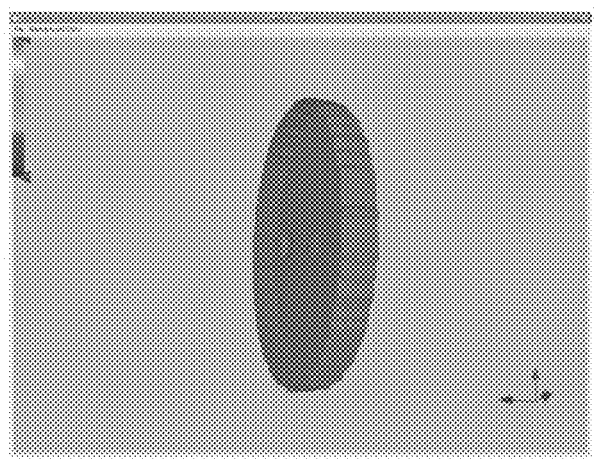
FIG. 16C illustrates the result of boundary evolution encountering the disc with parameters β and γ both set to a value of five.

The parameters α, β, and γ may be selected to achieve a desired behavior for boundary evolution (or may be presented such that a user can select a value for the parameter(s)). According to some embodiments, α is fixed at unity and β and γ are selected to achieve satisfactory boundary behavior. For example, β and γ may be chosen such that openings formed by the irregularity of the vasculature and/or necrotic regions of a tumor are filled and/or the boundary otherwise encloses the vasculature of interest according to a desired smoothness that accurately reflects the extent of the vasculature of interest. FIGS. 16A-16C shown a selection of parameters β and γ using synthetic data for illustration. FIG. 16A illustrates a disc having a hole in the center (similar simulations may be performed with a torus or other shapes as well). The disc has a thickness d, radius R and a hole having a radius r.

The structure illustrated in FIG. 16A may be geometrically and/or morphologically similar to structures that may be encountered by a boundary evolving on a 3D scalar field converted from a geometric representation of a vascular network. FIG. 16B illustrates the profile of the final evolution φ-field on the axis of the disc's rotation symmetry (i.e., the φ-value of the boundary versus the grid location) for a number of different combinations of β and γ. FIG. 16C illustrates the result of boundary evolution encountering the disc with parameters β and γ both set to a value of five (5). It should be appreciated that with the value set as such, the hole in the middle is closed and the boundary correctly covers the hole. It can be shown that with the parameters β and γ both set to a value of 5, any hole with radius r that is less than or equal to two times the thickness d will be filled. However, the parameters β and γ may be selected to be any value to properly locate the boundary according to the type of vasculature being bounded or wrapped. It should be appreciated that while the parameters β and γ may be fixed at any values that result in generally desirable boundary behavior, the parameters may also be made available as user selected values to allow robust boundary identification across a wide variety of vascular structures.

As discussed above, the techniques described for locating the boundary are based, at least in part, on defining the boundary as the implicit surface φ(x,y,x)=0 and using level set principles to evolve the boundary. However, due to the discrete nature of the 3D scalar field, further processing may be necessary to precisely locate the boundary (e.g., to precisely locate the implicit surface φ(x,y,x)=0). This may be achieved by searching for a zero crossings of φ and interpolating. According, to some techniques, a Marching Cubes algorithm may be performed to locate the boundary precisely and/or define a 3D mesh defining the location of the boundary (e.g., a mesh that describe locations wherein φ(x,y,x)=0).

Marching Cubes is well known algorithm for constructing a 3D mesh defining a surface described in William E. Lorensen, Harvey E. Cline: *Marching Cubes: A high resolution 3D surface construction algorithm*. In: *Computer Graphics*, Vol. 21, Nr. 4, July 1987, which is herein incorporated by reference in its entirety. According to some embodiments, a Marching Cubes algorithm is performed on the 3D scalar field after stabilization to construct a mesh (e.g., a triangulated surface) defining the boundary of the vasculature of interest. However, it should be appreciated that any method may be used to locate the boundary and/or generate a geometric representation of the boundary (e.g., a mesh), as the aspects of the invention are not limited in this respect.

Figure 17:
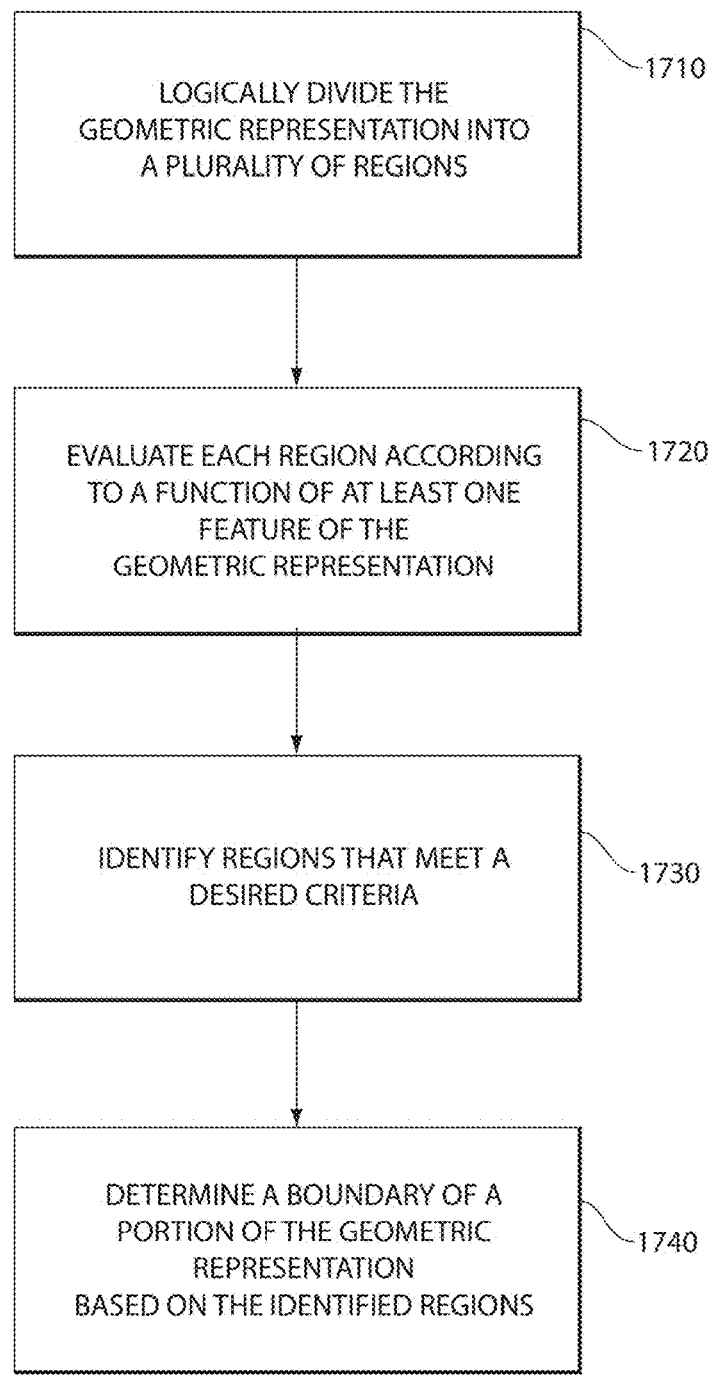
FIG. 17 illustrates a method of determining a boundary for a portion of a geometric representation of vasculature.

FIG. 17 illustrates a method of defining a boundary of vasculature of interest from a geometric representation of a vascular network, based on the foregoing and in accordance with some embodiments. First, a geometric representation of a vascular network (e.g., as obtained using any of the extraction techniques described herein or otherwise acquired) is logically divided into a plurality of regions (1710). For example, the geometric representation may be logically divided into a plurality of volumes of a desired size (which may be variable).

Each of the plurality of regions may be evaluated according to a function of at least one feature, property, parameter and/or attribute of the geometric representation (1720). For example, the vessel density (e.g., the number of poker chips per region) may be computed for each region, the vessel density of a particular vessel diameter (binned vessel density) may be computed for each region, the number of branch points may be computed for each region, some measure of curvature, tortuosity, vessel orientation, vessel length, etc. may be computed for each region. It should be appreciated that the function may include one or multiple features to be evaluated, as the aspects of the invention are not limited in this respect.

The evaluated regions may then be compared to a desired criteria to identify regions that meet the criteria (1730). The criteria may be any suitable criteria that facilitates distinguishing the plurality of regions. The criteria may be a single value (e.g., a threshold) or may be a more complex criteria. For example, if multiple features are evaluated, the criteria may include a threshold for each criteria. The criteria may include a range of values or a combination of a range of values. Any suitable criteria may be used, as the aspects of the invention are not limited in this respect.

The boundary of a portion of the vasculature of interest may be located based on the identified regions that meet the criteria (1740). According to some embodiments, the boundary is located by first labeling each region according to whether the region meets the criteria to generate a 3D scalar field representation of the geometric representation of the vascular network. The boundary may be located by applying an evolving boundary informed by a PDE, such that the evolving boundary stabilizes to suitably describe the boundary of the vascular of interest. However, the boundary may be located in other ways, as the aspects of the invention are not limited in this respect.

Figure 18:
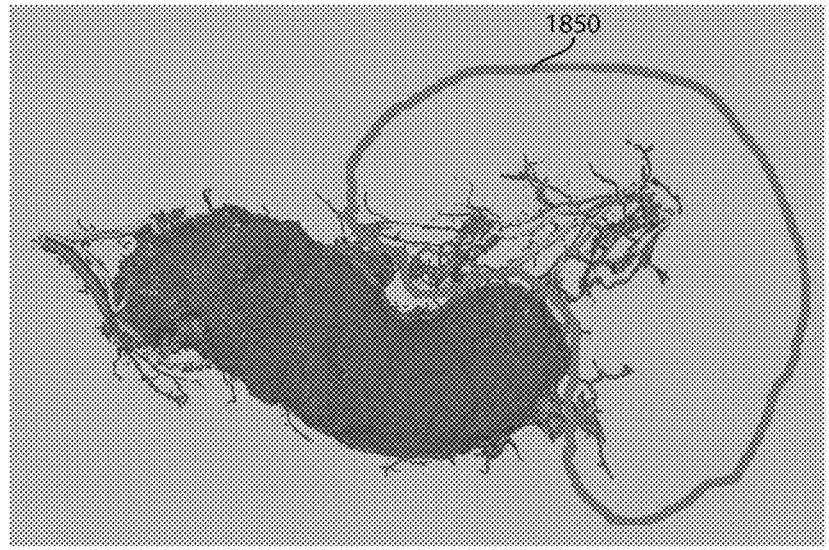
FIG. 18 illustrates noise regions within a geometric representation of vasculature.
Figure 19:
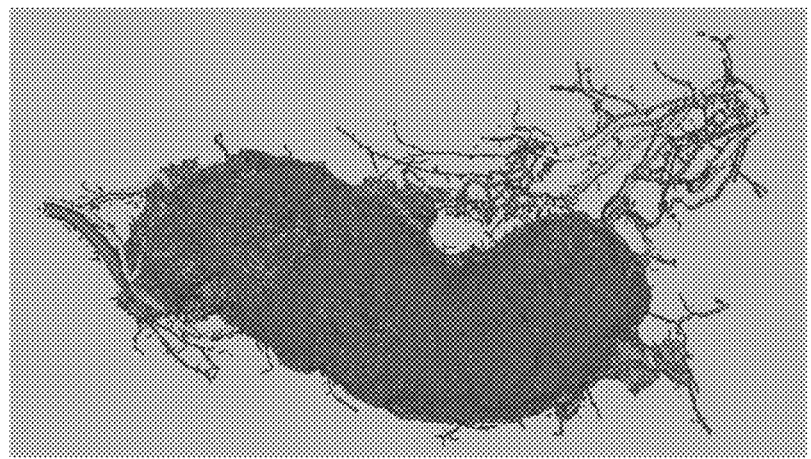
FIG. 19 illustrates a portion of a vascular network for which a boundary has been determined.

In some instances, evaluation and criteria techniques may identify one or more noise regions that are not part of the vasculature of interest. For example, FIG. 18 illustrates a geometric representation of a vascular network having vessels denoted by contour 1850 that may meet the designated criteria but are not part of the vasculature of interest. For example, the vessels within contour may meet a designated criteria but are not part of a tumor for which the boundary is intended to identify. Applicant has appreciated that such regions are typically smaller and/or isolated from the main (intended) regions. Accordingly, these regions may be removed by applying the techniques described herein to label all the regions, compute a volume for each region, and keep only a number of the largest regions equal to the number of regions expected for the vasculature of interest. FIG. 19 illustrates the bounded vasculature with the noise vessels correctly excluded from the boundary.

Figure 20:
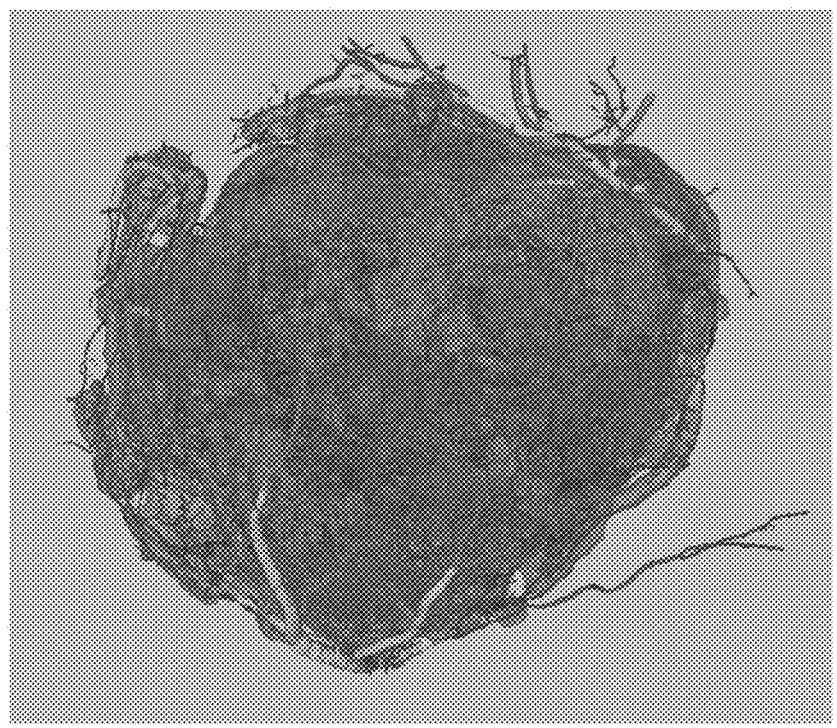
FIG. 20-22C illustrates a number of different types of vasculature and results of performing boundary finding.
Figure 21A:
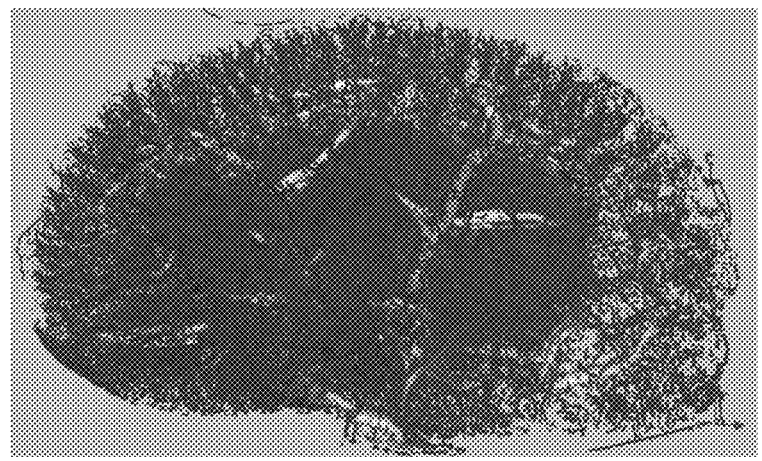
Figure 21B:
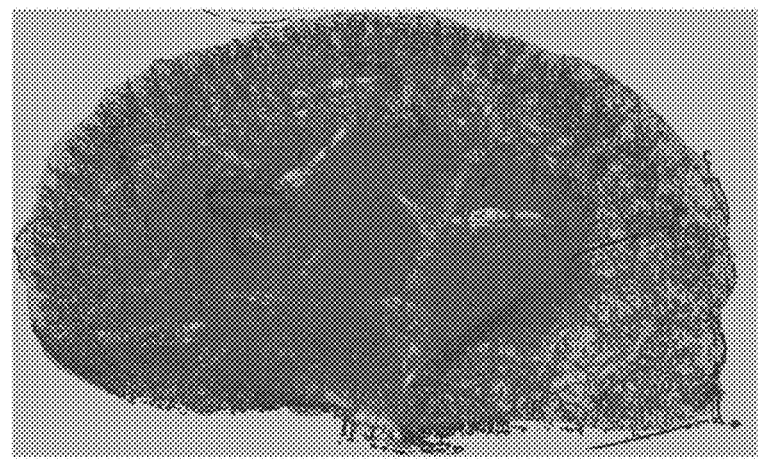
Figure 22A:
Figure 22B:
Figure 22C:

FIGS. 20-22 illustrate a number of different results of applying boundary finder techniques described herein to exemplary types of vascular networks. FIG. 20 illustrates a bounded (wrapped) tumor. FIG. 21A illustrates an extracted geometric representation of the vasculature of a kidney (e.g., as extracted from one or more images of the kidney using any technique described herein) and FIG. 21B illustrates the bounded or wrapped kidney vasculature using boundary finder techniques described herein. FIG. 22A illustrates the vasculature of a portion of the thigh muscle, which includes in the top right quadrant a lymph node of interest. FIG. 22B illustrates the wrapped lymph node wherein the vessels of the thigh that are not part of the lymph node have been excluded from the boundary by the automated techniques applied to the vasculature, embodiments of which are described in the foregoing. FIG. 22C illustrates a magnified view of the bounded lymph node. It should be appreciated that the above bounded vasculature of merely a few examples of the numerous vasculatures and vasculature structures that may be bounded to facilitate further analysis, as discussed in further detail below.

III. Analysis of Bounded Vasculature

As discussed above, bounded vasculature may provide a valuable tool to perform vascular analysis for diagnostic, prognostic other medical or research purposes. For example, analyses enabled by boundary finding techniques may facilitate drug efficacy assessment, detection of diseased tissue, disease diagnosis, comparisons of diseased with healthy tissues, quantification of diseased behavior, etc. In general, once a region of interest (e.g., a volume of vasculature of interest) has been identified by determining the boundary of the region, numerous analyses may be performed on the bounded region, exemplary analyses of which are described in further detail below.

Figure 23:
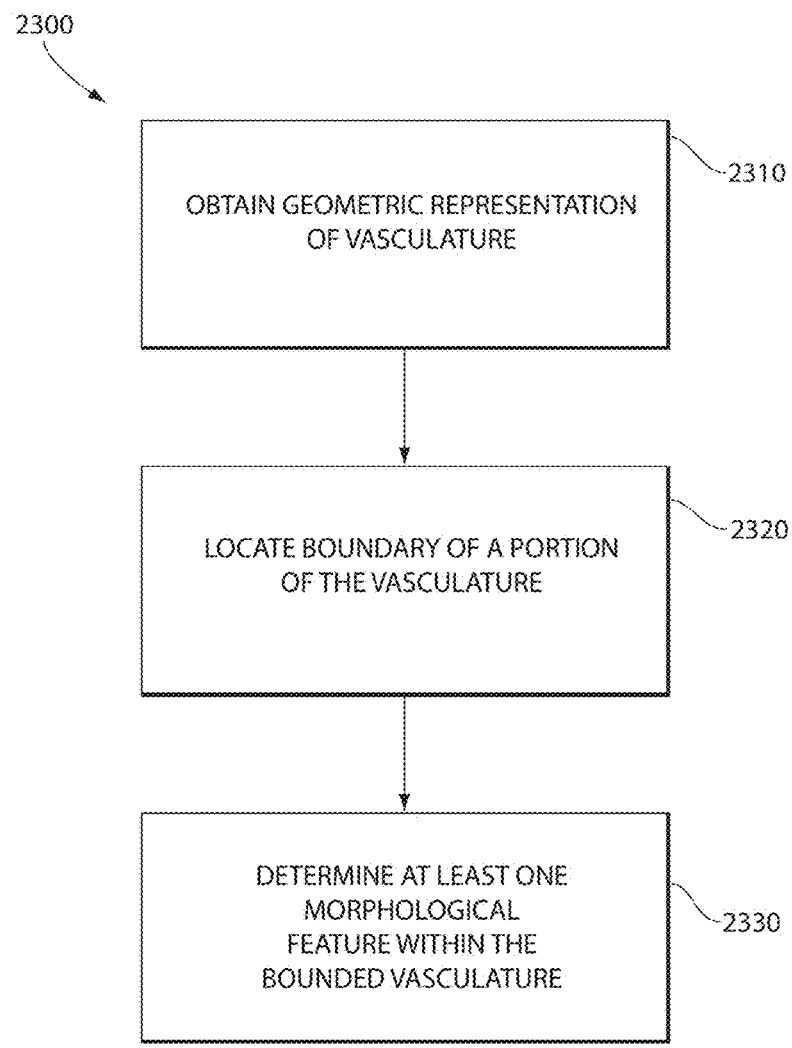
FIG. 23 illustrates a method of performing vascular analysis.

FIG. 23 illustrates a method of performing vascular analysis, in accordance with some embodiments. In act 2310, a geometric representation of a vasculature is obtained. As discussed above, the geometric representation of a vasculature may be obtained by receiving a pre-existing geometric representation or computing a geometric representation of the vasculature (e.g., using techniques for geometric extraction described herein). In act 2320, one or more regions of interest of the vasculature may be bounded or wrapped based on one or more features of the geometric representation. In act 2330, the one or more bounded regions of vasculature may undergo further processing to analyze any desirable feature, characteristic, attribute or morphology of the bounded region(s) of vasculature. Following below are non-limiting examples of analyses that may be performed on bounded vasculature.

Applicant has appreciated that some techniques for performing morphological analysis on a bounded vasculature may include identifying one or more regions of interest and evaluating the one more regions according to desired characteristics or one or more morphological features. A number of exemplary morphological features that may be of interest for any number of diagnostic, prognostic or medical purposes are listed in Table 1 below, some of which are discussed in further detail below.

TABLE 1

Vessel Density
Binned Vessel Density
Binned Vessel Population
Binned Vessel Volume
Vessel Population Density
Binned Vessel Population Density
Mean Vessel Density TABLE 1-continued Vessel Density Standard Deviation
Hot Region Ratio
Vessel Density Distribution
Vascular Surface Density
Binned Vascular Surface Density The term "binned" refers to an analysis performed on populations of vessels that have been categorized into a plurality of bins, wherein vessels in each bin share values of a property as defined by the corresponding bin. For example, bins may define ranges of vessel diameters such that vessels belong to the bin defining the diameter of the vessel. The vessels in each bin may then be evaluated separately to obtain information about properties of vessels in the respective bins (e.g., the locations assigned to a bin may be evaluated together and independent of the other bins to determine one or more morphological feature on a per bin basis.

In the case of vessel diameter binning, binned vessel density may be mathematically expressed as, $$bmvd(\phi) = \frac{V_{vessel}(\phi)}{V_{tumor}} = \frac{\pi n(\phi) l \phi^2}{4 V_{tumor}} \quad (48)$$

where $V_{vessel}(\phi)$ and $V_{tumor}$ are the vessel volume of diameter $\phi$ and tumor volume, respectively. It should be appreciated that tumor is being used as an exemplary bounded vasculature, however, the region may be an organ or other vasculature of interest that has been bounded. According to the above definition, vessel density may be expressed as, $$mvd = \sum_{\phi} bmvd(\phi) \quad (49)$$

That is, the vessel densities computed inside the bounded vasculature (or a region of interest) are summed over all bins (e.g., over all vessel diameters). Another morphological measure includes binned vessel population, which is the number of vessels of each diameter range and may be mathematically expressed as, $$bmvp(\phi) = P_{vessel}(\phi) = n(\phi) l \quad (50)$$

where $P_{vessel}(\phi)$ is the population of vessels of diameter $\phi$, which may be computed using the Poker Chip representation. For example, the binned vessel population may be computed by $n(\phi)l$ which is the number of poker chips in a region times the unit thickness of the poker chips (which may be related to the level of discretation of the geometric representation of the vascular network or chosen otherwise). As with binned vessel density, the vessel population may be computed by summing over vessels of all diameters in the region of interest. Another measure that may be useful relates to binned vessel volume which computes the volume of vessels of particular diameters in a given region of interest, and can be expressed mathematically as, $$bmvv(\phi) = V_{vessel}(\phi) = \pi \phi^2 n(\phi) l \quad (51)$$

Where $V_{vessel}(\phi)$ is the vessel volume of diameter $\phi$. The Poker Chip representation may be used to compute the binned vessel volume, for example, using the last expression where $n(\phi)$ is the number of poker chip with a diameter $\phi$ in a desired region and l is the unit thickness of the poker chips. The total vessel counterpart may also be computed by summing over vessel volumes of all diameters. Another measure that may be used to analyze a bounded vasculature includes binned vessel population density, which may be mathematically expressed as, $$bmvpd(\phi) = \frac{P_{vessel}(\phi)}{V_{region}} = \frac{n(\phi)l}{V_{region}} \quad (52)$$

Where $P_{vessel}(\phi)$ is the population of vessels of diameter $\phi$ and $V_{region}$ is the volume of a desired region. The binned vessel population density may also be computed using the Poker Chip representation, for example, using the last expression where $n(\phi)$ is the number of poker chip with a diameter $\phi$ in a desired region and l is the unit thickness of the poker chips. The total vessel counterpart may also be computed by summing over vessel population densities of all diameters. Another measure that may be used to analyze a bounded vasculature includes binned vessel surface density, which may be mathematically expressed as, $$bvsd(\phi) = \frac{S_{vessel}(\phi)}{V_{tumor}} = \frac{\pi n(\phi)l\phi}{V_{tumor}} \quad (53)$$

Where $S_{vessel}(\phi)$ and $V_{tumor}$ are the vessel surface of diameter $\phi$ and tumor volume, respectively. It should be appreciated that the bounded vasculature need not be a tumor and may be any vasculature network of interest for which a boundary has been computed. The binned vessel surface density may also be computed using the Poker Chip representation, for example, using the last expression where $n(\phi)$ is the number of poker chips with a diameter $\phi$ and l is the unit thickness of the poker chips. The total vessel counterpart may also be computed by summing over vessel population densities of all diameters.

Other measures may be computed based on analyzing morphological properties in volumetric regions (also referred to as ice-cubes). Such analysis may be performed to compute any number of morphological feature including, but not limited to, vessel population density, vessel volume density, vessel surface density, etc. When the morphological property is vessel population density, the ice-cube analysis may be expressed as, $$\rho(x, y, z) = \sum_{p_i \in N(x,y,z)} \frac{l}{L^3} \quad (54)$$

where $N(x,y,z)$ is a selected neighborhood of locations centered at the point $(x,y,z)$ in the bounded geometric representation, l is the unit thickness of, for example, a poker chip and L is the dimension of the ice-cube (e.g., the size of the selected neighborhood). It should be appreciated that any size for L may be selected. For example, for oncological purposes, L may be set to approximately 420 μm so that it is consistent with the biological observation that tumor vessels typically provide oxygen to cells up to approximately 200 μm away. However, any size neighborhood may be chosen, for example, to suit a particular type of analysis and/or application. The ice-cube density measure may facilitate computation of further morphological attributes of the bounded vasculature, some of which are described in Table 2 below.

TABLE 2

| | |
|---|---|
| Mean vessel ice-cube density in a region | MD (x) = E[ρ] |
| Standard Deviation of vessel ice-cube density in a region | DV (x) = Var[ρ] |
| Hot region ration in a region | $HRD(x) = \frac{Volume[\rho > T]}{Volume[\rho \geq 0]}$ |
| Vessel ice-cube density distribution in a region | $DI(\rho) = \frac{Hist(\rho)}{\sum_y Hist(\rho)}$ |

Any one or combination of the above morphological properties may be used to analyze a bounded vasculature. Some embodiments include identifying regions of interest within a bounded vasculature using one or more of the morphological properties described herein. For example, one or more morphological properties may be evaluated over the bounded vasculature and regions that meet a certain criteria may be identified. For example, any one or combination of morphological properties may be evaluated for the bounded vasculature and regions that evaluate to a value that exceeds a desired threshold may be identified.

When such identified regions of interest are evaluated against a threshold, they may be referred to as hot spots or hot regions to indicate that the identified regions include morphological properties that are generally of interest due to having relatively high values with respect to the evaluated morphological properties as compared to other regions in the bounded vasculature. When the evaluating function is vessel density and the criteria is a threshold, hot spot regions may be computed as, $$hr(T)=\{(x,y,z)|\rho(x,y,z) \geq T\} \quad (55)$$

It should be appreciated that equation 55 may be generalized by replacing $\rho(x,y,z)$ with $F(G_{bounded})$ where F is any function operation on the bounded geometric representation of the vasculature ($G_{bounded}$) and the threshold T is generalized as any criteria C. For example, F may be any function that evaluates one or more morphological properties of the bounded geometric representation, either morphological properties discussed herein or other properties and C may be any designated criteria. As such, the hot regions may be of particular diagnostic or prognostic interest or may be suitable for evaluating the efficacy of treatment and/or may be particularly attractive targets for therapy (e.g., radiation therapy), as discussed in further detail below. It should be appreciated that such regions of interest may be identified using any evaluation function and any criteria, as the aspects of the invention are not limited in this respect.

Another morphological measure is the hot region ratio which is defined as the ratio between the hot region volume and the volume of the bounded vascular (e.g., tumor volume, organ volume, etc.). The hot region ratio may provide additional useful morphological information of the bounded vasculature to assist in any number of diagnostic or prognostic assessments, treatment efficacy or any other type of assessment.

Other regions within a bounded vasculature may be identified independent of morphological content, for example, identified based on the region's location within the bounded vasculature. One class of such regions are referred to herein as "iso-shells", which are regions in a bounded vasculature wherein locations (e.g., discrete volumes in the bounded vasculature) within each iso-shell have a distance from the boundary that are within the same range of values defined by the respective iso-shell. A mathematical description of an iso-shell may be expressed as:

$$\mathcal{R}(i \mid \delta) = \{(x, y, z) \mid i\delta \le d(x, y, z) < (i+1)\delta\} \quad (56)$$

where, $$d(x, y, z) = \frac{dist(x, y, z)}{\max\{dist(x, y, z)\}} \quad (57)$$

That is, the bounded vasculature is logically divided into a number of shells, each having a thickness $\delta$. Each location (e.g., each volume) of the geometric representation that is within the boundary is labeled as belonging to one of the shells based on the locations distance from the boundary (i.e., each iso-shell contains the locations of the bounded geometric representation having a distance from the boundary within the range defined by the respective iso-shell) Analysis may then be performed on each iso-shell to assess various characteristics of regions of the vasculature at different distances from the boundary. It should be appreciated that any feature, characteristic, property or morphological attribute may be computed for the iso-shells, such as any of the morphological attributes described herein. For example, vessel density, binned vessel density, branch density, any one or combination of measures of vessel orientation or length, or metrics associate with curvature or tortuosity, etc., or any of the measures in Table 1, or that are described below.

Figure 24:
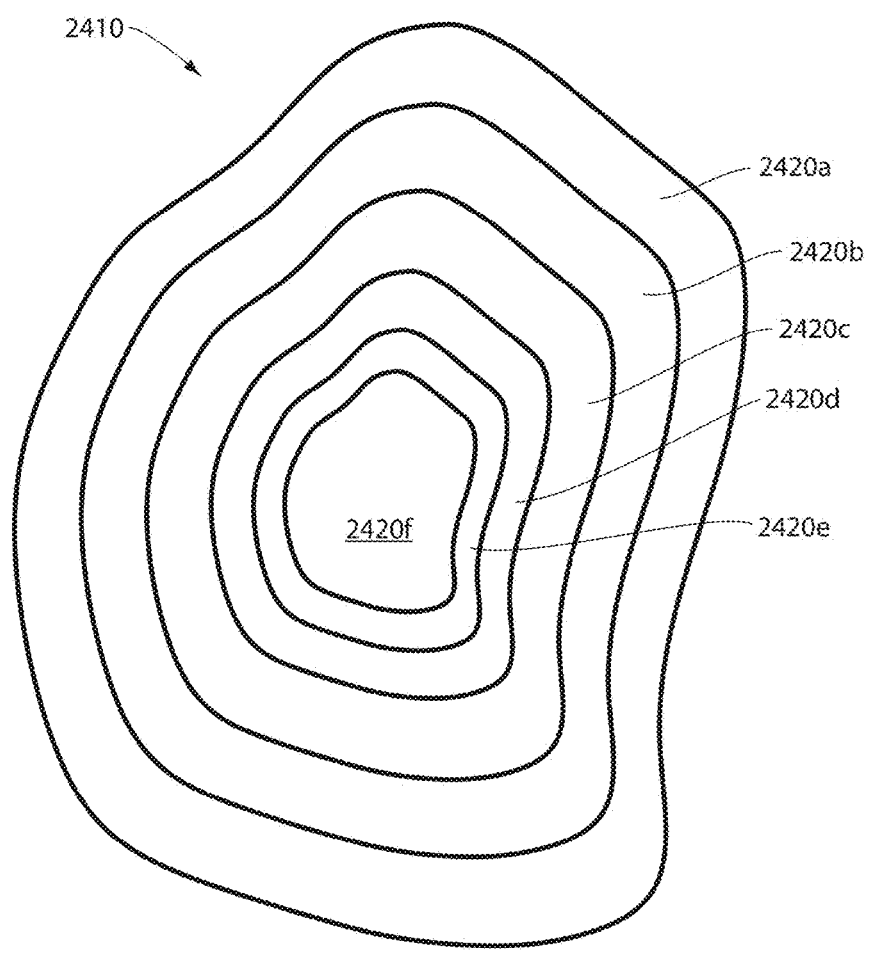
FIG. 24 illustrates a schematic of an iso-shell computation.

FIG. 24 illustrates a schematic of a bounded region that has been divided up into a plurality of iso-shells. For example, a bounded vasculature 2410 is schematically illustrated with a number of iso-shells, each an increasing distance away from the boundary. Each shell 2420 contains the locations having a distance from the boundary within the range defined by the thickness of the associated iso-shell. While the shells are shown as 2D in FIG. 24, the computation is not so limited and is preferably performed in 3D. Each shell may then be processed to determine one or more morphological features of the shell. It should be appreciated that the shells may be chosen to have the same thickness or the thicknesses may be variable. For example, the thickness of the shell may decrease as the distance from the boundary of the respective shell increases, or vice-versa. Other regions that are defined based on location within the vessel (e.g., relative to the boundary) may be computed and used for analysis as well, as the aspects of the invention are not limited in this respect.

Figure 25:
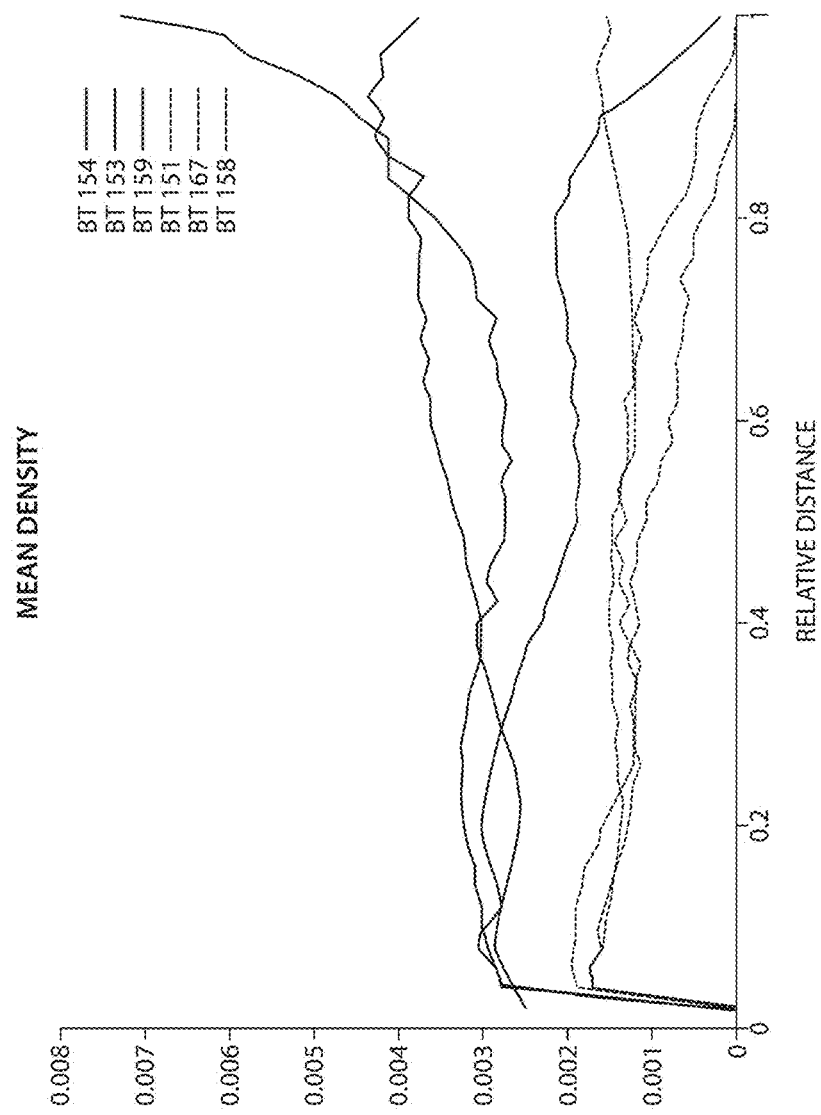
FIGS. 25-28 illustrate plots of respective morphological features evaluated for a number of iso-shells.

FIGS. 25-28 illustrate exemplary morphological features computed for a number of computed iso-shells. FIG. 25 illustrates plots of the average vessel density in a number of different iso-shells. Such a measure may be used for example to determine where in a tumor or organ a particular drug targets and is the most effective. For example, if an iso-shell analysis is performed on a bounded vasculature at different points in time during treatment, it can be observed which iso-shells are undergoing the greatest amount of change from a vessel density perspective. This information may not only inform as to the efficacy of the treatment but also may provide insight into how particular treatments operate and/or how they impact the vasculature, which may in turn allow for improvements to the treatments.

Figure 26:
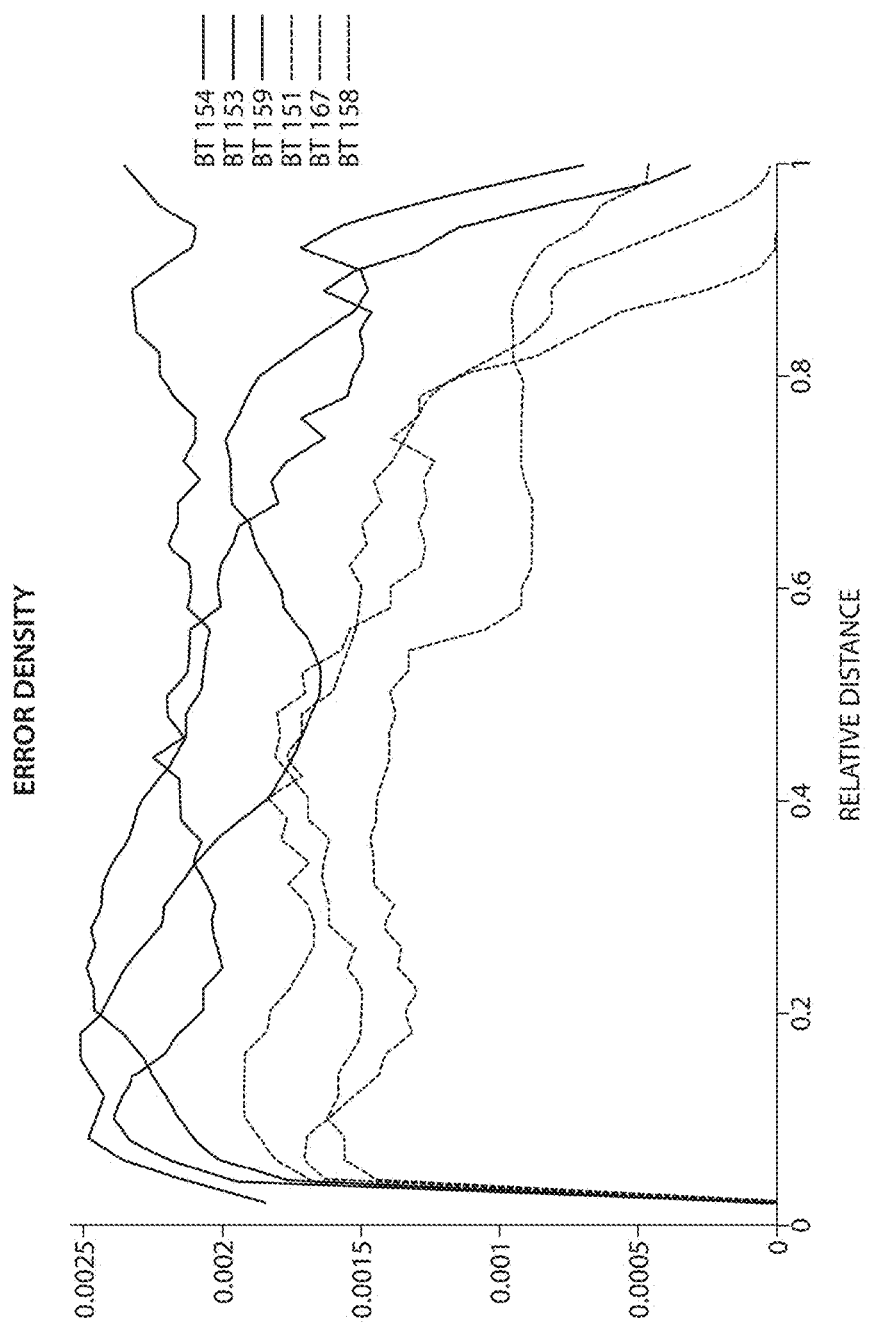
Figure 27:
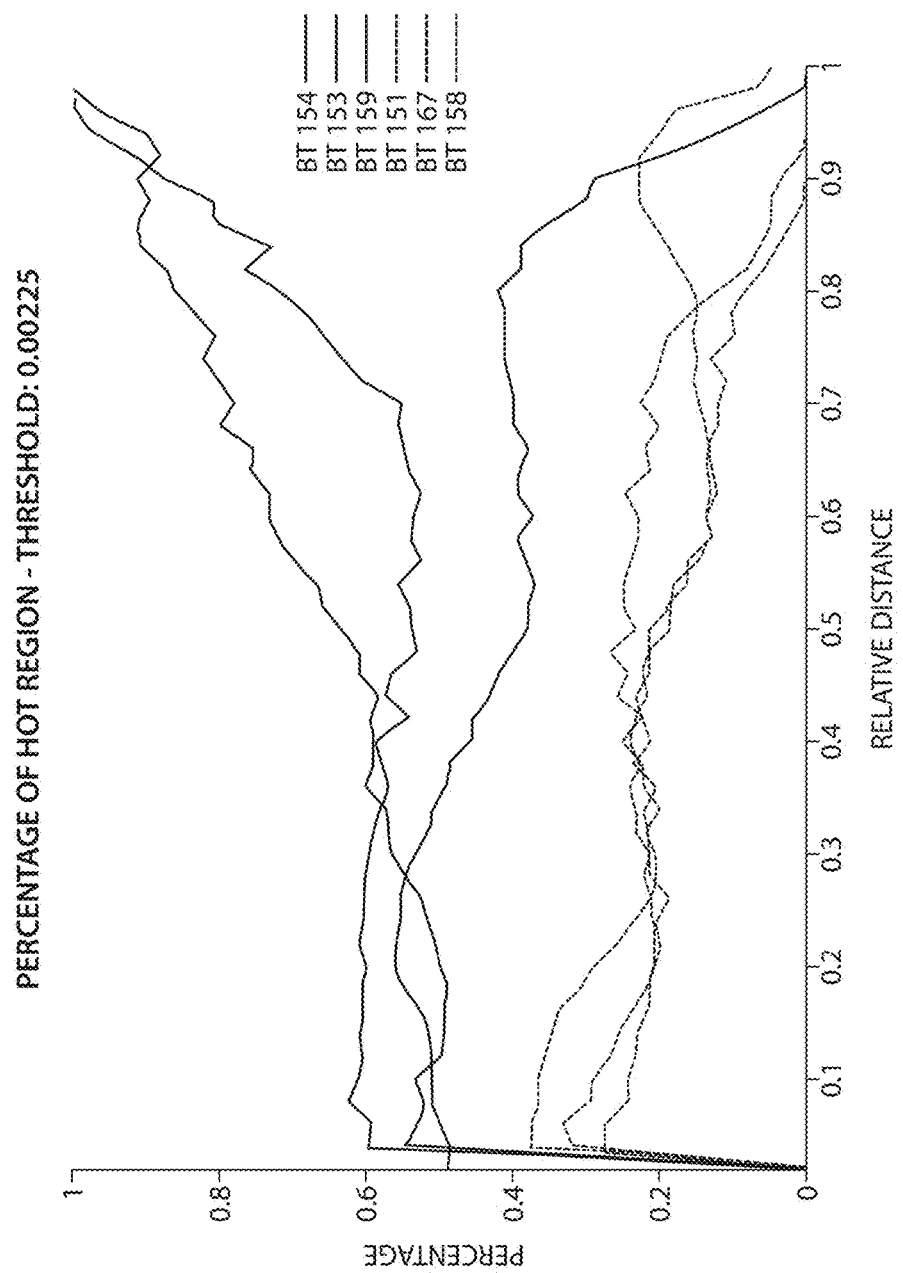
Figure 28:
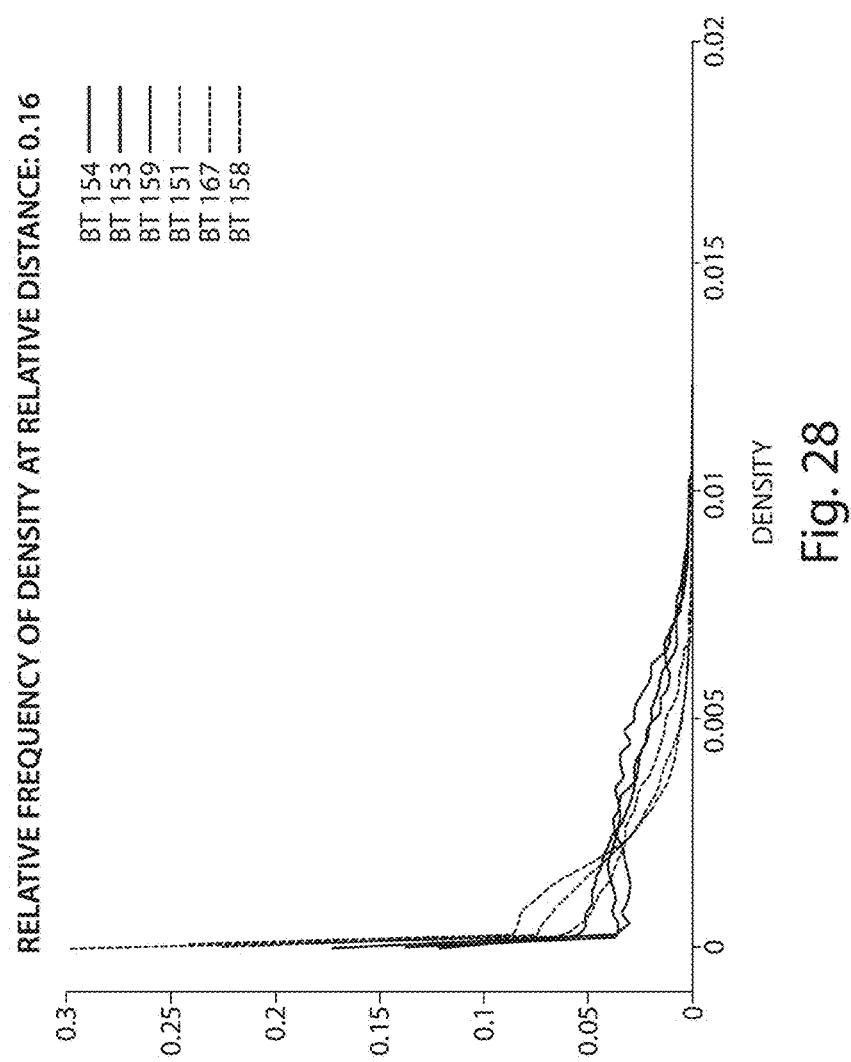

FIG. 26 illustrates plots of the standard deviation of vessel density in a number of different iso-shells. FIG. 27 illustrates plots of hot spot ratios in a number of different iso-shells. For example, the hot spots may be those regions in which the vessel density exceeds a designated threshold, or may denote some other evaluation that meets a designated criteria. FIG. 28 illustrates plots of density distribution in a number of different iso-shells. It should be appreciated that the morphological measures computed within the iso-shells may be computed using ice cube concepts. For example, the one or more morphological measures may computed for each defined volumetric region within the iso-shells. It should be appreciated that one or more morphological features within the iso-shells may be tracked over time to assist is assessing treatment efficacy or to gain insight into how a treatment operates (e.g., what one or more morphological traits does the treatment impact).

Figure 29:
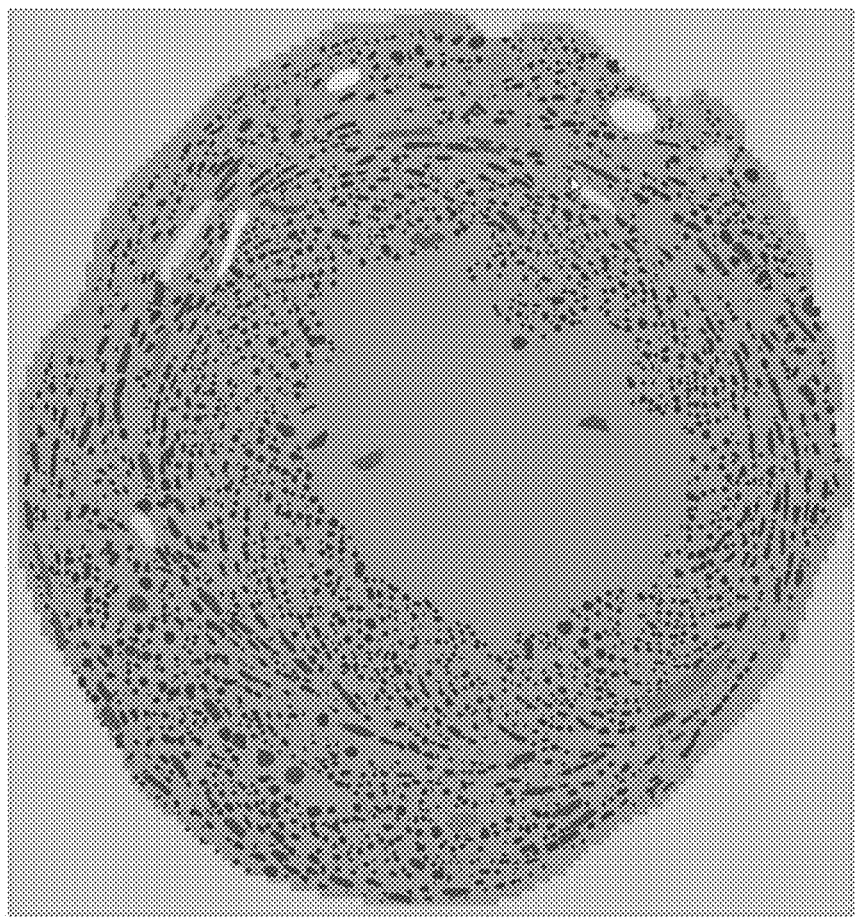
FIG. 29 illustrates a 2D slice of a geometric representation of a vascular network on which vessel density has been evaluated and displayed.

2D slices of the geometric representation within the bounded vasculature may be provide another region-based analysis tool that may be useful in providing diagnostic, prognostic or other medical information. FIG. 29 illustrates a 2D cross-section of the geometric representation of the bounded portion of a vasculature (e.g., a heart). Within the 2D cross-section, any of the above analyses may be performed, including but not limited to hot spot analysis, evaluation of one or more morphological properties, iso-shell analysis, etc. In FIG. 29, the morphological attribute evaluated and displayed is vessel density. However, any other analyses may be performed within one or more 2D slices of the geometric representation of the bounded vasculature, as the aspects of the invention are not limited in this respect.

Bounded vasculature of an organ can be compared to examples of bounded vasculature of healthy tissue to assess disease or for any other diagnostic, prognostic or analytic purpose. Bounded tumors may be compared with healthy tissue to quantify severity or otherwise assess characteristics of the tumor. Moreover, bounded tumors obtained at different points in time may be compared to assess treatment efficacy, tumor evolution, etc. Bounded vasculature may be analyzed in other different respects, some of which are discussed in further detail below, as the aspects of the invention are not limited in this respect.

Figure 30:
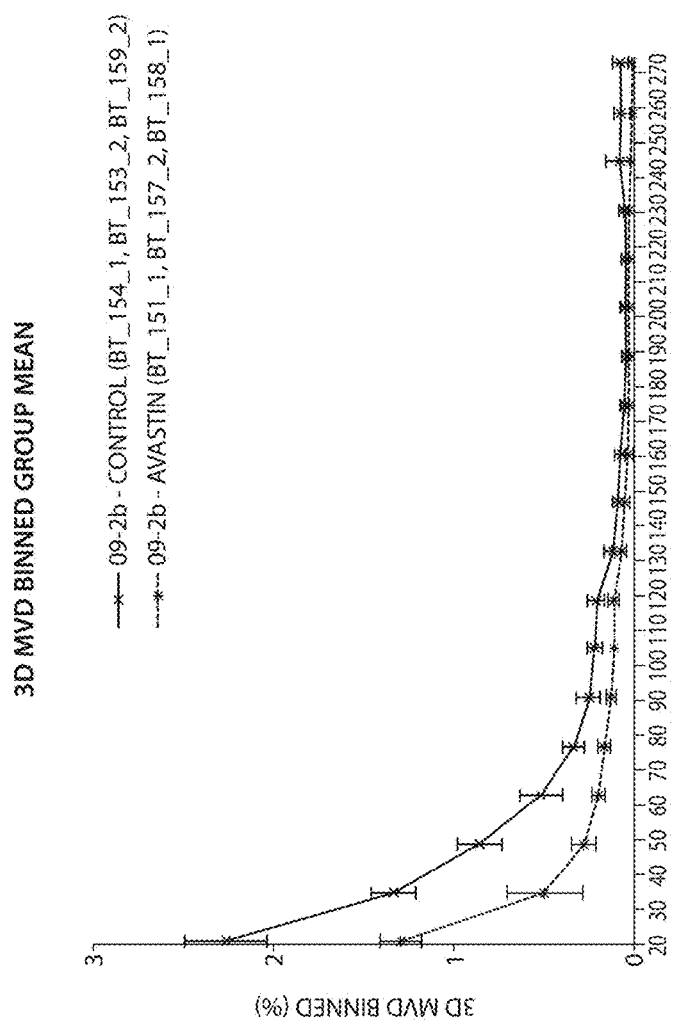
FIG. 30-32 illustrate different morphological features plotted as a function of vessel diameter for control and treated vasculatures.
Figure 31:
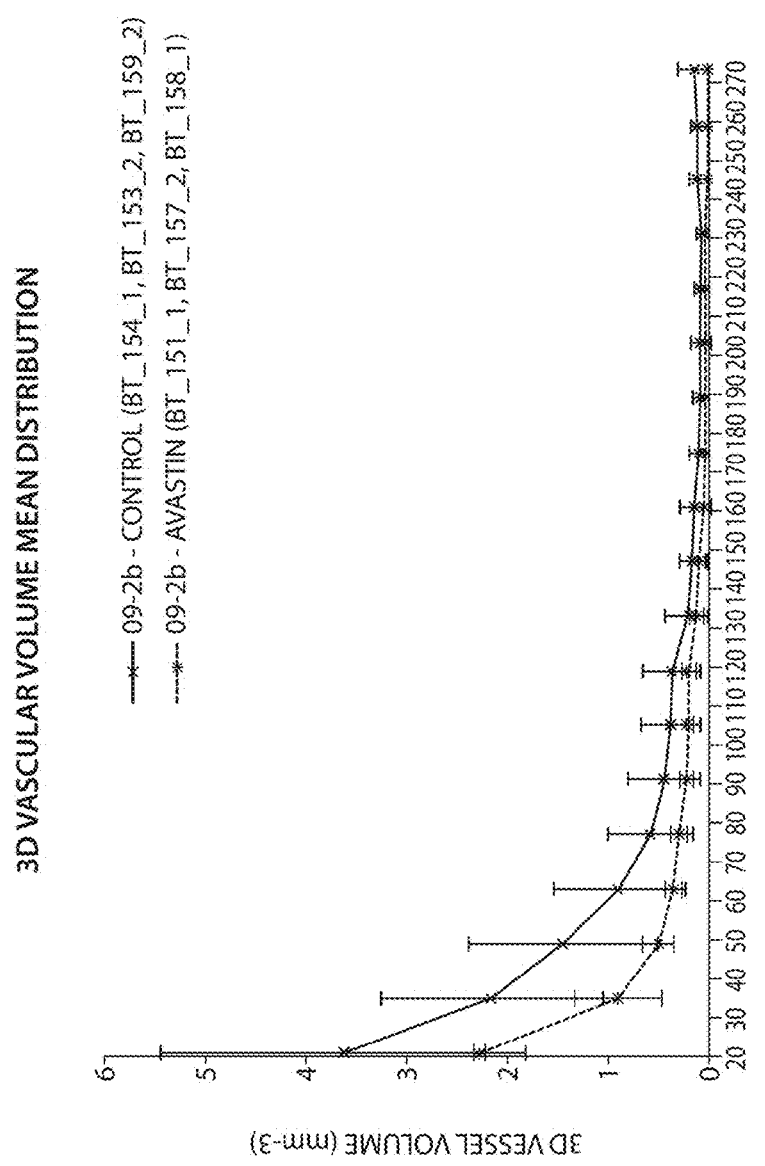
Figure 32:
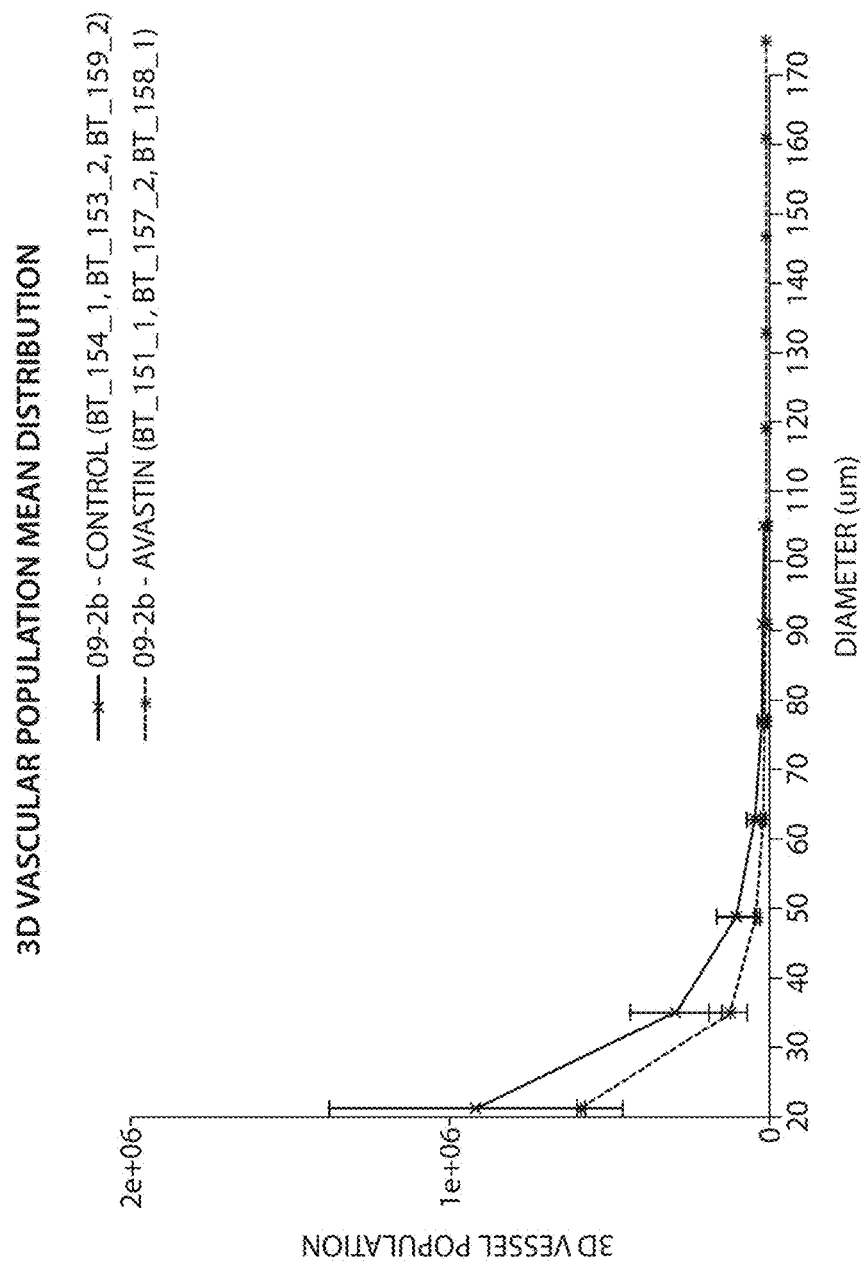
Figure 33:
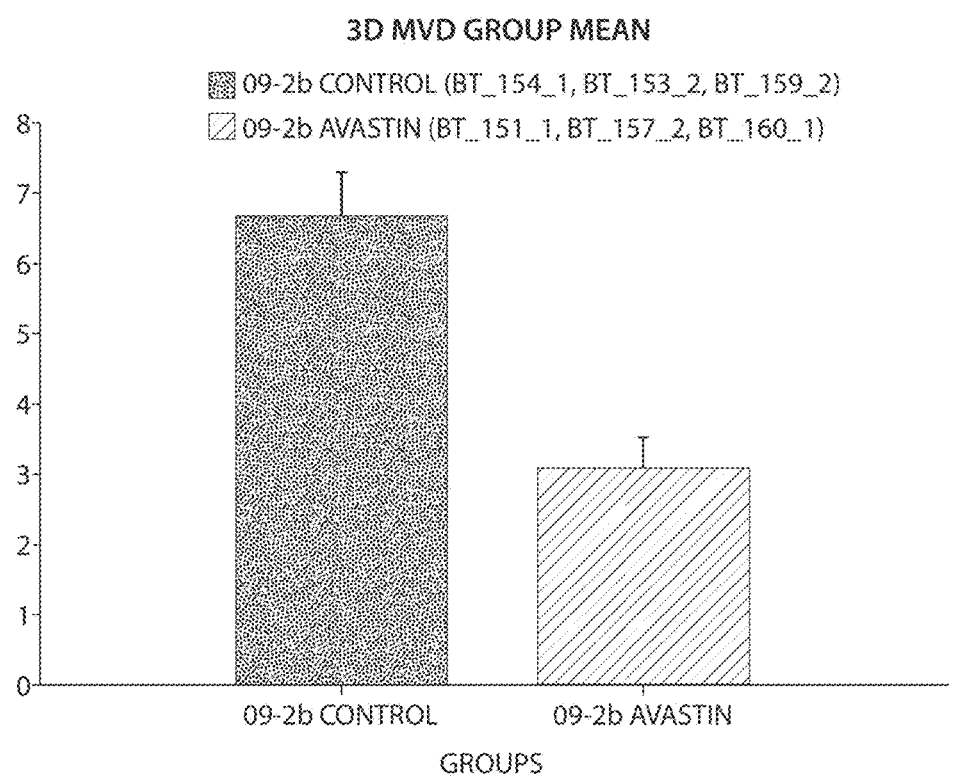
FIG. 33 illustrates a morphological feature for both a control and treated vasculature.

As discussed above, computed morphological features may be used to compare the same features obtained from healthy tissue, or to compare the same features extracted from a bounded vasculature at different points in time to, for example, assess the effectiveness of treatment. FIGS. 30-33 illustrate examples of using various morphological properties described herein to, for example, quantify diseased vasculature and/or assess the effectiveness of a particular treatment. FIGS. 30-32 illustrate plots of a respective morphological feature as a function of vessel diameter for a control vasculature and for a vasculature treated with Avastin. As clearly shown, there are differences in the corresponding morphological features between the control and treated vasculatures, indicating that the treatment is impacting the vasculature. Moreover, the impact may differ depending on the vessel size. That is, differences between the control and treated plots may be larger or smaller depending on the diameter of the vessel. Applicant has appreciated that the differences may be quantified to define a range wherein differences are different enough to help determine which vessel diameters are being targeted and impacted by the treatment.

According to some embodiments, diameter ranges that are being effected by a treatment (e.g., drug treatment, radiation therapy, etc.) are determined. The diameter range may depend on cell line type, tissue type (e.g., particular organ, tumor, etc.) and the type of treatment. It may be a relatively tedious and time consuming process to manually find the treatment effective range amongst the relatively large amount of combinations of cell line types, tumor types, and drugs. Furthermore, manual processes are prone to errors. Applicant has developed a computer implemented method of determining a treatment effective range using measures that determine statistically significant changes.

According to some embodiments, Welch's t-test may be used to analyze a control and treated population. Welch's t-test is a statistical hypothesis test which can answer the question of whether two means are equal, given two groups of data having different variance. Welch's t-test defines the statistic t:

$$t = \frac{\overline{X_1} - \overline{X_2}}{\sqrt{\frac{\alpha^2}{N_1} + \frac{\alpha_2^2}{N_2}}}$$

Where $X_i$, $\alpha_i^2$ and $N_i$, are the $i^{th}$ sample mean, variance and size, respectively. The degree of freedom v may be approximated as:

$$v = \frac{\sqrt{\frac{\alpha^2}{N_1} + \frac{\alpha_2^2}{N_2}}}{\frac{\alpha_1^4}{N_1^2(N_1-1)} + \frac{\alpha_1^4}{N_2^2(N_2-1)}}$$

Figure 34:
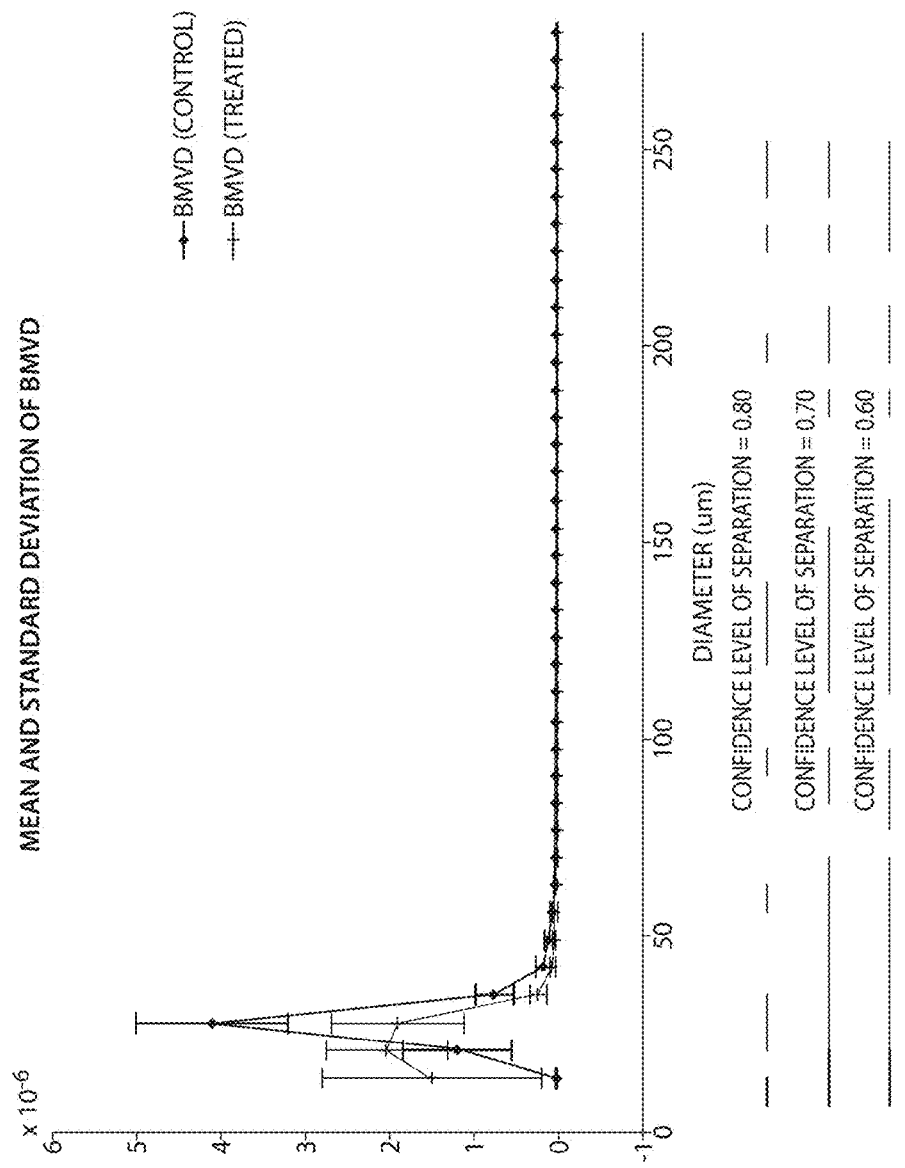
FIG. 34 illustrates Welch's t-test applied to morphological data obtained from control and treated vasculatures.
Figure 35:
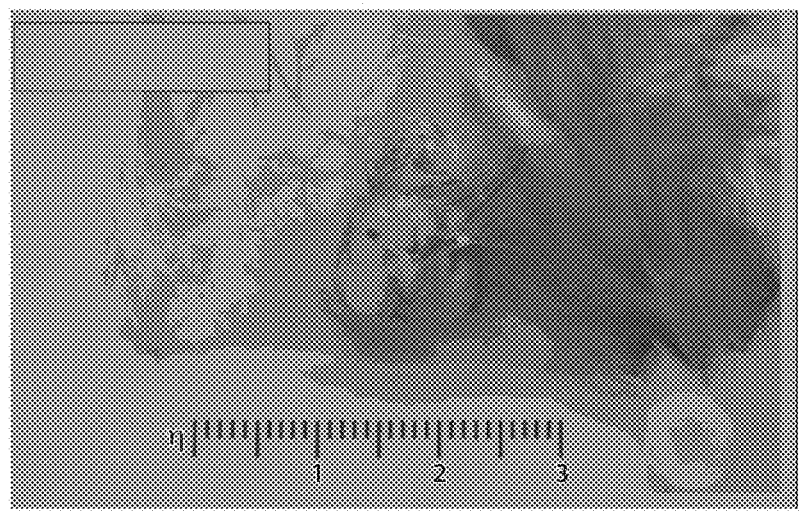
FIG. 35 illustrates a subcutaneous mouse tumor xenograft prior to perfusion.

Once t and v are computed, these statistics can be used with a t-distribution to test whether the two population means are equal under a given confidence interval. The result of the t-distribution test indicates which ranges have statistically significant changes. Other approaches to identifying statistically significant changes may be used, as the aspects of the invention are not limited in this respect. FIG. 34 illustrates an example of determining statistically significant differences between a control and a tumor treated with Avastin for two weeks.

As discussed above vessel density may be an important morphological indicator (e.g., bio-marker) when assessing a bounded vasculature. According to some embodiments, the vessel density in a small volume V at location (x, y, z) may be expressed as, $$p(x, y, z) = \frac{\sum_{r=r_{min}}^{r_{max}} vol(r)}{V}$$

where r is the radius of the vessels, and $r_{min}$ and $r_{max}$ may be chosen depending on the analysis being performed (e.g., 10 μm and 50 μm, respectively such that the volume V=0.022 mm³). This defines a density field inside the bounded vasculature. Vessel density may be a valuable prognostic indicator for a wide range of tissue types. The joint distribution of density and diameter may therefore be useful to understand various treatment processes such as the anti-angiogenesis drug mechanism. According to some embodiments, the Poker Chip representation may be used as each poker chip with radius r at location (x, y, z) has the information of vessel diameter and vessel density ρ at point of (x, y, z). Therefore, a (density, diameter)-joint histogram h(r, ρ) can be constructed.

Numerous examples of morphological features that may be computed for a bounded vasculature are described herein. It should be appreciated that these morphological features may be used alone or in any combination to assist in vascular analysis. The various morphological attributes may be used in any number of different ways including the techniques described herein and in published application numbers WO2006/069379, WO2008/016652, WO2008/002648, WO2009/088963, the disclosures of which are incorporated by reference herein in their entirety. Provided below are a number of examples of techniques that may be performed using one or more morphological attributes of a bounded vasculature.

It should be appreciated that some or all of the embodiments of the invention can be automated as described herein.

It also should be appreciated that any one or more structural parameters described herein may be evaluated by comparison to a reference parameter. In some embodiments, a reference parameter may be an amount or score for that parameter in a normal or healthy subject. In other embodiments, a reference may represent a diseased condition. In some embodiments, a change or amount of any structural parameter that is correlated or associated with a disease or condition as described herein may be a statistically significant change or difference in that parameter in a diseased or test subject relative to a reference subject. In some embodiments, a difference or change in a structural parameter may be an increase or a decrease in a particular parameter (or a combination of parameters). An increase in a parameter may be at least a 5%, 10%, 20%, 30%, 40%, 50%, 60%, 70%, 80%, 90%, 100%, or greater increase in that parameter in a test subject relative to a reference subject. Similarly, a decrease in that parameter may be at least a 1%, 5%, 10%, 20%, 30%, 40%, 50%, 60%, 70%, 80%, 90%, 100%, or greater decrease of a measure of that parameter in a test subject relative to a reference subject. Once an amount of change or difference in a parameter has been correlated or associated with a disease or condition, that level may be used in subsequent methods according to the invention. Accordingly, in some embodiments, a difference of at least at least 1%, 5%, 10%, 20%, 30%, 40%, 50%, 60%, 70%, 80%, 90%, 100%, or more of any given structural parameter (e.g., tortuosity, density, volume, or any other individual structural feature or distribution of structures or structural features as described herein) relative to a reference value may be used as a threshold for methods of the invention. It should be appreciated that higher or lower or intermediate values may be used. It also should be appreciated that different parameters may have different threshold or reference levels. Also, different parameters (and/or different levels for each parameter) may be associated with different conditions or diseases. Accordingly, specific disease or condition values or thresholds may be identified for different parameters or combinations thereof. These threshold values may be used for disease detection, diagnosis, monitoring, or for any other therapeutic, clinical, or research application described herein (e.g., in automated methods described herein).

These and other aspects of the invention are illustrated by the following non-limiting examples.

EXAMPLES

Example 1: Disease, Tissue, and Regional Analysis of Vasculature

In some embodiments, aspects of the invention may be used to evaluate, detect, and/or monitor any diseases or conditions associated with changes in vascular structure. Diseases associated with changes in vascular structure (e.g., that can be detected by the presence of abnormal vascular patterns at a given time or abnormal structural changes observed as a function of time) include, but are not limited to, cancer, heart diseases and related circulatory disorders, eye diseases, skin disorders, and surgical conditions. For example, diseases and conditions associated with changes in vascular structure include, but are not limited to, tumor angiogenesis, recurrent and progressive cancers, coronary artery disease, cardiomyopathy, myocardial ischemia, arteriosclerosis, atherosclerosis, atherosclerotic plaque neovascularization, arterial occlusive disease, ischemia, ischemic or post-myocardial ischemia revascularization, peripheral vascular disease (including diabetic retinopathy), thromboembolic diseases (e.g., stroke, pulmonary embolism, brain aneurisms, and deep venous thrombosis), claudication, rheumatologic disorders (e.g., arthritis), immune disorders (e.g., rheumatoid arthritis, vasculitis, Wegner's granulomatosis, and systemic lupus erythematosis (SLE)), pulmonary disorders (including, emphysema, COPD, idiopathic pulmonary fibrosis, pulmonary arterial hypertension, and other respiratory disorders), myeloma, vascular proliferative disorders, gastrointestinal disorders (e.g., Crohn's disease, ulcerative colitis, and inflammatory bowel disease (IBD)), gynecologic disorders (endometrial polyp, vaginal bleeding, endometriosis, dysfunctional uterine bleeding, ovarian hyperstimulation syndrome, preeclempsia, polycystic ovarian syndrome (PCO), cervical cancer, and cervical dysplasia), skin disorders (infantile hemangioma, verruca vulgaris, psoriasis, neurofibromatosis, epidermolysis bullosa, Stevens-Johnson syndrome, and toxic epidermal necrolysis (TEN)), eye disorders (macular degeneration, maculopathies, diabetic retinopathy, and retinopathy of prematurity (retrolental fibroplasia)) wound healing, inflammation associated with immune responses, ischemia including limb ischemia and cardiac ischemia, Alzheimer's disease and other disorders such as wound dehiscence, Buerger Disease (thromboangitis obliterans, arteriosclerosis obliterans (ASO), ischemic ulcers) multiple sclerosis, idiopathic pulmonary fibrosis, HIV infections, plantar fasciosis, plantar fasciitis, Von Hippel-Lindau Disease, CNS hemangioblastoma, retinal hemangioblastoma, thyroiditis, benign prostatic hypertrophy, glomerulonephritis, ectopic bone formation, and keloids.

These different diseases are characterized by different changes in vasculature structure. Accordingly, in one aspect of the invention, parameters and scoring methodologies are used to detect, diagnose, and monitor particular diseases and their related therapies based upon particular characteristics of vasculature structure indicative of the disease. Even within each disease category, different diseases can be characterized by different changes in vasculature structure. Accordingly, structure mining and scoring can be fine-tuned to increase the sensitivity for particular types of disease within a category (e.g., lung cancer score, breast cancer score, etc., can be developed). Patient-specific scoring parameters can also be developed to follow the progression of a specific disease or disorder in a patient.

Structural vasculature changes include changes in vascular architecture and vascular morphology affecting blood vessels and/or lymph vessels. Structural changes can involve neovascularization (including the growth of large blood vessels (e.g., arteriogenesis) and the growth of microvasculature (angiogenesis)), large blood vessel expansion, and vascular necrosis. Angiogenesis involves the formation of new blood vessels that sprout from preexisting blood vessels. Angiogenesis is different from vasculogenesis, which is the de novo formation of vessels that occurs primarily during development. Vasculogenesis is rarely associated with a disease or disorder. However, aspects of the invention can be used to study the natural process of vasculogenesis to help identify and understand defects in de novo blood vessel formation.

Angiogenesis is often associated with tumor growth and is a useful biomarker for cancer. Angiogenesis also can be associated with conditions where new blood vessel growth occurs in response to a reduced oxygen supply or blood flow (whether due to thrombosis, embolism, atherosclerosis, or other chronic occlusion or narrowing of the vasculature). Certain respiratory, cardiovascular, and inflammatory disorders also are associated with angiogenesis.

Angiogenic blood vessels have structural characteristics that are different from those of established blood vessels. For example, the branching patterns and tortuosity of angiogenic blood vessels are very different from those of normal blood vessels. These and other structural features are found predominantly in microvasculature and can be used for mining and scoring vasculature structural images. However, changes in larger blood vessels such as arteries and veins also may be associated with certain diseases or disease stages (e.g., growth and development of large tumors or late-stage tumors).

The vasculature that supports a tumor is typically associated with the connective tissue of the tumor (the stroma) that supports the malignant cells (in the parenchyma). A discussed above, tumor blood vessels are irregularly spaced and characterized by heterogeneous structural patterns or features. However, the formation of tumor blood vessels and other forms of angiogenesis may involve a series of characteristic stages (see, for example, Dvorak, 2003, American Journal of Pathology, Vol. 162:6, pp. 1747-1757, the disclosure of which is incorporated herein by reference in its entirety). Early stage angiogenesis may be characterized by vascular hyper-permeability, fibrin deposition and gel formation, and edema. This may result in the enlargement of micro-vessels such as venules. The cross-sectional area of an enlarged micro-vessel may be about 4 fold that of a normal micro-vessel. The perimeter of an enlarged micro-vessel may be about 2 fold that of a normal micro-vessel. Enlarged micro-vessels may occupy about 4-7 fold the volume of normal micro-vessels in a region of active angiogenesis. The appearance of enlarged micro-vessels may be followed by the appearance of "mother" vessels that are enlarged, thin-walled, serpentine, and hyper-permeable. Mother vessels may undergo a process of bridging whereby trans-luminal bridges are formed dividing the blood flow within the vessel into smaller channels. A developing mother vessel also may contain one or more glomerular bodies that may expand to divide the lumen of the mother vessel into several smaller channels that are typically tortuous. Bridging and glomerular body formation in mother vessels may lead to the appearance of small capillaries characteristic of angiogenesis. However, certain mother vessels persist as abnormally enlarged vessels with thin walls. These vascular malformations are often characterized by the presence of an asymmetric muscular coat and perivascular fibrosis. Small arteries and arterioles also may increase in size in diseased tissue. Aspects of the invention include detecting and/or monitoring any one or more of the blood vessel structural changes described herein. In one embodiment, the presence of one or more patterns (e.g., individual structural features or distributions) characteristic of new blood vessel formation may be used to detect or monitor a disease. In another embodiment, the presence of one or more specific patterns (e.g., individual structural features or distributions) may be used to determine the stage of angiogenesis (e.g., early-stage, mid-stage, late-stage, etc.) in a body region.

Accordingly, abnormal changes in blood vessel size (diameter and/or length) can be early signs of diseases such as cancer or other disease associated with an increased blood supply. Changes in blood vessel size may occur before any structural signs of angiogenesis appear. In one embodiment, aspects of the invention are useful to detect blood vessels (e.g., capillaries) that are swollen and/or longer than normal. For example, aspects of the invention are useful to detect abnormally long intrapapillary capillary loops in situ (e.g., associated with early stages of cancer in oesophageal mucosa).

In some embodiments, blood vessel changes indicative of necrosis in tumor tissues may be indicative of the aggressiveness of the tumor tissue and/or the likelihood of metastasis, and/or the responsiveness to therapy, and/or the efficacy of a therapeutic treatment (e.g., a candidate drug), and/or an therapeutic treatment selection and/or modification (e.g., a change in drug or dose for an individual patient). Accordingly, in situ patterns (e.g., individual structural features or distributions) indicative of necrosis may be useful biomarkers for patient prognosis. In certain embodiments, necrosis within a region of a tumor may be indicated by one or more of the following patterns (e.g., individual structural features or distributions) within that region: a collapse in blood vessel structure, poor vascularization (e.g., a low blood vessel density relative to other regions of the tumor or relative to the perimeter of the tumor), a change in blood vessel size or shape over time, a lower than threshold number of blood vessels, blood vessels (e.g., in the microvasculature or the capillaries) that are separated by a greater than threshold distance (e.g., by more than 100 microns, more than 150 microns, or more than 200 microns) within a volume of the tumor, micro-vessel diameter and/or density indicative of undervascularization, etc., or any combination thereof. In some embodiments, a volume of avascularization or undervascularization may be evaluated or quantified and used as an indicator of necrosis. It should be appreciated that other indicia of necrosis may be used, alone or in combination with blood vessel features. Other indicia may include indicia of tissue collapse or cavitation that may be visualized (e.g., using CT etc.) and/or indicia of tissue viability using one or more markers of metabolic activity (e.g., ones that may be analyzed using a PET scan, etc.).

Aspects of the invention may be used for the detection (e.g., the automatic detection) of necrotic areas in a subject (e.g., in a tumor in a subject). A necrotic region is an avascular region within the boundary of a diseased tissue. Methods of the invention may be used to detect (e.g., automatically) the transition between the vascularized diseased tissue and avascular region that defines the boundary of the necrotic region.

Aspects of the invention also may be used to detect or evaluate (e.g., automatically) a response to therapy. For example, a response to therapy (e.g., to a specific drug and/or a specific dosage of a drug, and/or to a combination of drugs and specific dosages of these drugs, etc.) can be detected and assessed as follows. Changes in the vascular patterns (e.g. vessel normalization/straightening, disappearance of smaller diameter vessels leading to lower microvessel density and to skewing of the vessel diameter distribution towards the larger vessels) may be detected and/or evaluated within the volume defined by the boundary of the diseased tissue and the boundary of the necrotic area. An increase in the absolute volume size of the necrotic area and/or the rate of such change while the total volume of the disease (e.g. tumor) volume stays constant may be detected and/or evaluated as an indicator that the therapy is effective. An increase in the ratio between the absolute volume size of the necrotic area and the total disease (e.g., tumor) volume and/or the rate of change in this ratio may be detected and/or evaluated and used as an indicator that the therapy is effective. A ratio of the diseased tissue volume and the necrotic region volume may be detected and/or evaluated and when it approaches 1 and the overall diseased tissue volume starts shrinking it provides an indication that a therapy is effective.

Structural representations of blood vessels can be mined to identify and evaluate certain patterns (e.g., individual structural features or distributions) that can be used to provide a score that is related to the probability that the blood vessels are normal or abnormal (e.g., disease associated). Patterns (e.g., individual structural features or distributions) for scoring blood vessels include, but are not limited to, the following: diameter, curvature, tortuosity (including, for example, the degree of tortuosity, the length of the blood vessel along which abnormal tortuosity is observed, etc.), variability or heterogeneity (including spatial variability or heterogeneity over distance or in a volume), branching shape or pattern, branching density, branching hierarchy, blood vessel density, distribution of vessel size (ratio of microvasculature to macrovasculature) a field effect (the presence of blood vessels bending towards a specific region), blood vessel diameter distribution, variability of the geometric orientation of blood vessels or fragments thereof, and the distribution of the orientation(s) within a field. The score may have more significance if two or more of these parameters are evaluated. In some embodiments, a score is generated using one or more of these structural parameters combined with additional information such as patient-specific medical information (e.g., age, weight, height, gender, etc.) and the presence of one or more additional indicators of disease such as a visible lesion on an X-ray or other image. In some embodiments, a score can be provided for a tumor. An example of a useful score is one that reflects the vascularity of a tumor. An abnormally high vascularity (measured as a higher than normal blood vessel number, density, length, or combination of the above) is generally indicative of a more aggressive or invasive tumor. In one embodiment, vascularity is evaluated by measuring the volume of the lumen of angiogenic vasculature (the volume within the blood vessel tree associated with a tumor). In another embodiment, a measure of vascularity is provided by dividing the volume of the angiogenic lumen by the volume of the solid tumor. Additional information can be gleaned from obtaining a score (or other structural evaluation) at two or more times. A changing score (or other structural evaluation) is indicative of an evolving vasculature that could be associated with a disease or disorder. It should be appreciated that the patterns (e.g., individual structural features or distributions) described herein can be identified and analyzed for a field of analysis without imposing a connectivity on the vessels being studied. In some embodiments, it may be sufficient to analyze only fragments of blood vessels in order to detect one or more structural features of individual vessels or geometrical features of a field of vessels that are different from normal features. For example, blood vessel fragments having an average length of 0.5 mm, 1 mm, 5 mm, 10 mm, 50 mm, 1 cm, 5 cm, 10 cm, 50 cm, etc. may be used. However, it should be appreciated that shorter or longer or intermediate lengths may be used.

The scoring and mining aspects of the invention described herein can be automated. Accordingly, diseased (e.g., angiogenic) vasculature can be automatically detected amidst normal vasculature. Various vasculature parameters can be automatically detected and scored, either separately or in any combination, including vessel tortuosity, vessel branching, vessel density, and total intra-vascular volume, but the invention is not limited to any particular parameter or combination.

In one embodiment, aspects of the invention can be used to detect blocked blood vessels, and thromboembolic events, including stroke, lung emboli, blocked micro-coronaries, deep-vein thrombosis, etc. Blocked blood vessels can be detected (1) directly by detecting structural changes in the blocked blood vessel (e.g., detecting a clot, wall thickening, or other signs of reduced flow) and/or (2) indirectly by detecting new vasculature that was generated in response to the blockage. In general, the formation of collateral blood vessels is more ordered than angiogenesis associated with cancer. One aspect of the invention described herein also allows clots to be detected in small blood vessels.

As discussed above, aspects of the invention can be used to screen the entire vasculature structure of a human or other animal to screen for any form of abnormality in any tissue. Alternatively, a subset of the body may be screened. Accordingly, vasculature structures such as a vascular tree can be analyzed for one or more organs or tissue types. In addition, only a portion of the vasculature may be analyzed within any target volume as opposed to the entire vascular tree in that volume. This may be done by analyzing structure data focused on the area of interest, or large amounts of structure data may be obtained, but an analysis may be restricted to a subset of the available data. In some embodiments, only a portion of a vascular tree may be represented and/or analyzed, for example only those vessels that are of a particular size. In other embodiments, only fragments of a vascular tree are represented and/or analyzed if the fragments are sufficiently informative to provide patterns (e.g., individual structural features or distributions) of interest. Fragments may include branches or may be unbranched. The portion of the vasculature being analyzed may be statistically significant, such that any observation (normal or abnormal) is physiologically significant. For example, branched structures may not be required for the analysis if a sufficient number of vessel substructures are analyzed to confidently detect any other patterns (e.g., individual structural features or distributions) that may be associated with vasculature changes (e.g., angiogenesis) such as high vessel density. In aspects of the invention, vascular patterns may be detected and/or evaluated in situ in a volume of 1 mm$^3$, 2 mm$^3$, 5 mm$^3$, 1 cm$^3$, 2 cm$^3$, 5 cm$^3$, 10 cm$^3$, etc. However, smaller or larger or intermediate volumes also may be analyzed.

Different tissues and organs have different and characteristic blood vessel patterns (e.g., the lung which is highly vascularized). Accordingly, in one embodiment, structural analyses and associated structural parameters may be optimized for evaluating different tissues.

In some embodiments, scan data is obtained and/or analyzed for one or more organs (e.g., lung, heart, colon, brain, liver, pancreas, kidney, breast, prostate, etc.) or tissue (e.g., skin, bone, etc.) or portion of any of the above.

Brains may be evaluated for signs of brain tumors and/or other neurological disorders that can be associated with changes in vascular patterns. For example, Alzheimer's may be associated with certain vascular abnormalities. In one embodiment, one or more changes in blood vessel pattern (e.g., shape and/or size) may be detected as an indicator of high blood pressure in the brain.

In some embodiments, certain specific regions of organs or tissues are focused on. For example, atherosclerosis is typically found in certain parts of the arterial tree (e.g., bifurcations, side branches, regions opposite flow dividers, and other areas where angiogenesis often occurs in association with atherosclerosis) and certain cancers tend to occur more frequently in certain organ or tissue regions (e.g., colon cancers are not distributed evenly along the length of the colon).

In other embodiments, aspects of the present invention may be used to follow up with individuals who have been identified as having one or more other indicia of disease (e.g., fecal occult blood, a colon polyp, a lung nodule, one or more cysts or other indicia of disease). Aspects of the invention may be used to confirm the presence of a disease, determine a location for the disease-associated lesion, or provide an evaluation or prognosis of a disease. For example, aspects of the invention may be used to determine whether abnormal vasculature is present at the site of a lesion (e.g. a colon polyp, a lung nodule, a bladder cyst, a prostate cyst, a breast cyst, a spot on a mammography, or any other cyst, lump, or spot that may be detected physically, visually, or using any other diagnostic technique) and help evaluate the likelihood of a malignancy (or other carcinogenic disease stage) associated with the lesion. Accordingly, aspects of the invention may be used for virtual malignancy detection (e.g., virtual colonoscopy, virtual colon malignancy detection, virtual bronchoscopy, virtual lung malignancy detection, virtual mammography, virtual cystoscopy, etc.).

In other embodiments, aspects of the invention may be used for screening a cancer patient to evaluate the extent of a cancerous lesion and/or to screen for the presence of one or more metastatic lesions (e.g., one or more loci associated with angiogenesis). A cancer patient may be screened upon initial diagnosis of a primary cancer. In addition or alternatively, a cancer patient may be screened at least once after an initial cancer treatment (e.g., surgery, radiation, and/or chemotherapy). This screening may include the original cancer locus to detect any cancer recurrence. This screening may include similar body tissue to screen for the presence of other lesions in the same tissue or organ (e.g., the entire colon may be screened when a cancerous lesion is detected in one region of the colon, the second breast may be screened when a cancerous lesion is detected in one breast, etc.). This screening also may be extended to the whole body or to one or more other loci suspected of containing a metastatic lesion. In one embodiment, a cancer patient may be screened several times after an initial cancer treatment (e.g., at time intervals of about 6 months, about 1 year, about 2 years, about 5 years, or at other time intervals).

In one embodiment, a follow up procedure may involve screening one or more organs or tissues for the presence of a metastatic lesion. Different cancers may have different characteristic patterns of metastasis. Accordingly, different target loci may be screened for different cancers. For example, metastatic breast cancer typically spreads to the lungs, the liver, bone, and/or the CNS. Therefore, one or more of these tissue types or organs may be screened after a patient is diagnosed with breast cancer. Similarly, other target loci may be screened after a patient is diagnosed with another cancer type. In some embodiments, the entire body of a cancer patient may be screened for indicia of metastasis.

In one aspect, an initial screen may be performed on an entire body, or an entire organ, using a low resolution representation and/or, for example, analyzing only one or two or a small number (e.g., less than five) pattern parameters in order to detect indicia of a disease. Subsequently, the presence and or nature of the disease may be diagnosed using a higher resolution representation and/or, for example, analyzing one or more additional pattern parameters or alternative pattern parameters than those that were analyzed for the initial detection.

It should be appreciated that some or all of the diagnostic aspects of the invention can be automated as described herein.

Example 2: Bounded Vasculature

Some aspects relate to biomarkers identified in blood vessel structure. Some aspects of relate to analyzing vascular structure, for example, by assessing vascular biomarkers, using the Poker Chip representation (i.e., one exemplary type of 3D geometric representation of vasculature (see, for example, FIGS. 35-42 and 43-47). Some biomarkers provided by aspects of this invention relate to structural parameters of blood vessels (see, for example, the Figures). Some biomarkers provided by aspects of this invention are based on voxel (unit of volume) analysis of a given volume (see, for example, FIGS. 48-54). For example, a voxel may be associated with information related to vascular structure (e.g., vessel density), and voxel analysis of a given tissue volume may be used for continuous mapping of the vasculature in said tissue volume. In some embodiments, the boundary of a diseased tissue, for example a tumor, is determined, for example by determining a tumor wrap (e.g., to define the outer surface of the tumor at the boundary with normal tissue). In some embodiments, a biomarker provided by aspects of this invention is assessed within a defined boundary of a healthy and/or diseased tissue (e.g., within a volume contained within a tumor wrap).

Example 3: Vascular Biomarkers

Some aspects provide biomarkers of vasculature structure useful to identify and precisely locate abnormalities in vasculature, for example abnormalities associated with malignant tissue. Some non-limiting examples of vasculature structure biomarkers in accordance to this invention may be related to vascular organization, vascular density, and/or vascular anatomy. Some vascular biomarkers provided by this invention are related to micro-vasculature, for example to micro-vascular organization, micro-vascular density, and/or micro-vascular anatomy.

Some non-limiting examples of vascular organization biomarkers according to some aspects of this invention are vascular hierarchy (for example distribution of vascular hierarchy bins over a given tissue volume, frequency of a given vascular hierarchy bin within a given tissue volume), vascular branching (for example number of blood vessel branching points over a given blood vessel length, branching point density in a given volume), vascular alignment, vascular orientation, vessel length, or inter-vessel distance.

Some non-limiting examples of vascular density biomarkers according to some aspects of this invention are total vessel density in a given tissue volume, total vessel volume density in a given tissue volume, vessel density in a given tissue volume, and then vessel volume density in a given tissue volume. In some embodiments, biomarkers relating to vascular density can be used to define vascular hot spots and necrotic regions within a tissue. A vascular hot spot may be defined as an area and/or volume of a tissue for which a vascular density related biomarker according to some aspects of this invention is determined to be above a specific threshold value. Similarly, a necrotic region may be defined as an area and/or volume of a tissue for which a vascular density related biomarker according to some aspects of this invention is determined to be below a specific threshold value. Threshold values may be determined from data acquired from control and/or reference tissue, for example healthy tissue of the same tissue type, for example from the same subject or a different or a group of different subjects, non-diseased tissue in proximity to a diseased tissue, or from theoretical and/or historical data. A vascular hot spot may be defined as a tissue area and/or volume in which the value for a vascular density related biomarker is increased by about 10%, about 20%, about 30%, about 40%, about 50%, about 60%, about 70%, about 80%, about 90%, about 100%, about 250%, about 500%, about 750%, about 1000%, about 5000%, or about 10,000% as compared to a reference or control value. A necrotic region may be defined as a tissue area and/or volume in which the value for a vascular density related biomarker is decreased by about 10%, about 20%, about 30%, about 40%, about 50%, about 60%, about 70%, about 80%, about 90%, about 100%, about 250%, about 500%, about 750%, about 1000%, about 5000%, or about 10,000% as compared to a reference or control value. In some embodiments, a hotspot may be identified as a region that has a vasculature level that is in the top approximately 1%, approximately 5%, approximately 10%, approximately 20%, or approximately 50% highest levels of vasculature of the tumor tissue (e.g., as defined by the tumor wrap). In some embodiments, a necrotic region may be identified as a region that has a vasculature level that is in the lowest approximately 1%, approximately 5%, approximately 10%, approximately 20%, or approximately 50% lowest levels of vasculature of the tumor tissue (e.g., as defined by the tumor wrap).

Figure 36:
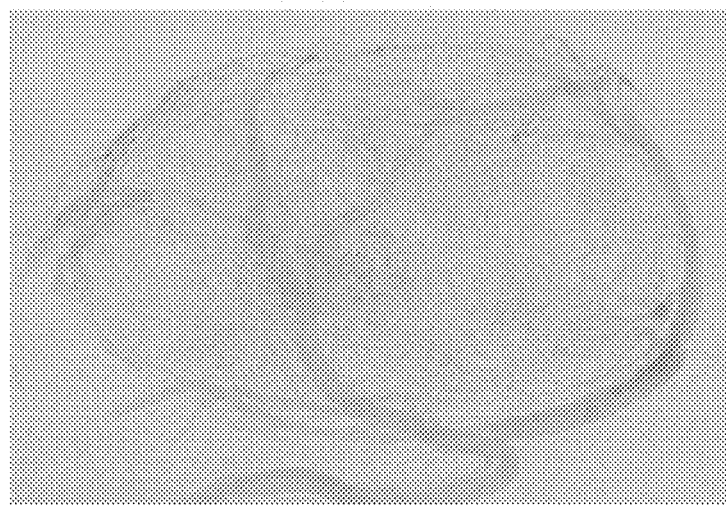
FIG. 36 illustrates a single tumor vasculature syndrome single X-ray raw view (out of 1000 snapshots)
Figure 37:
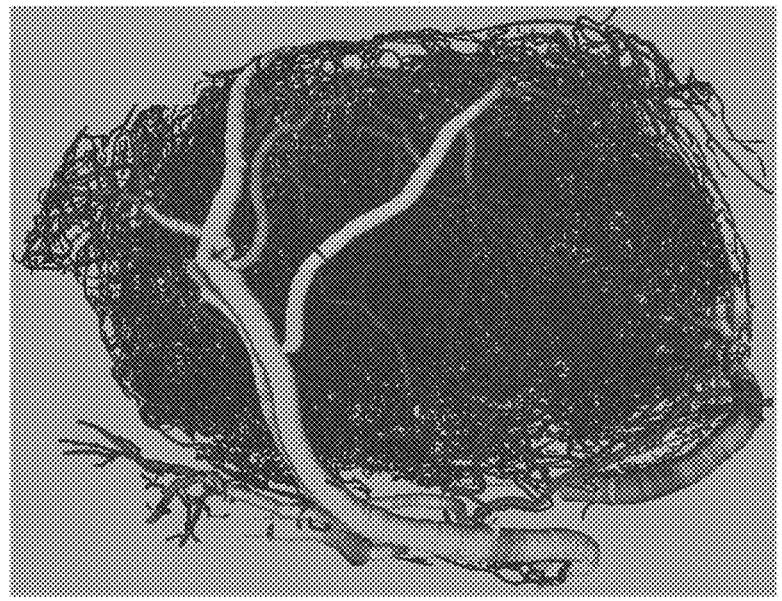
FIGS. 37-39 illustrate respectively different views of 3D segmented and reconstructed tumor vasculature of the same tumor.
Figure 38:
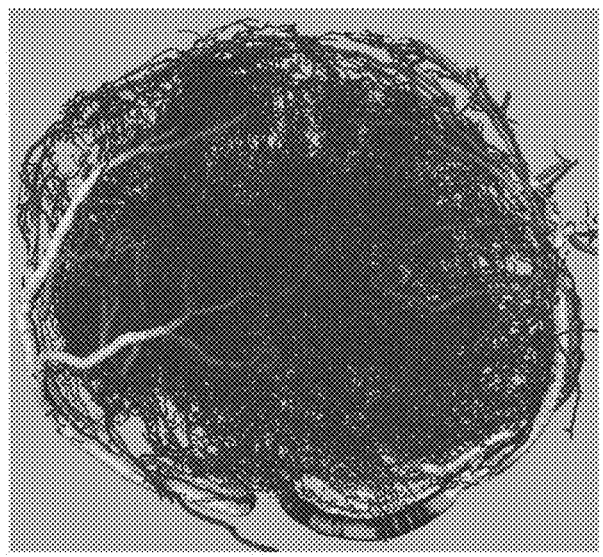
Figure 39:
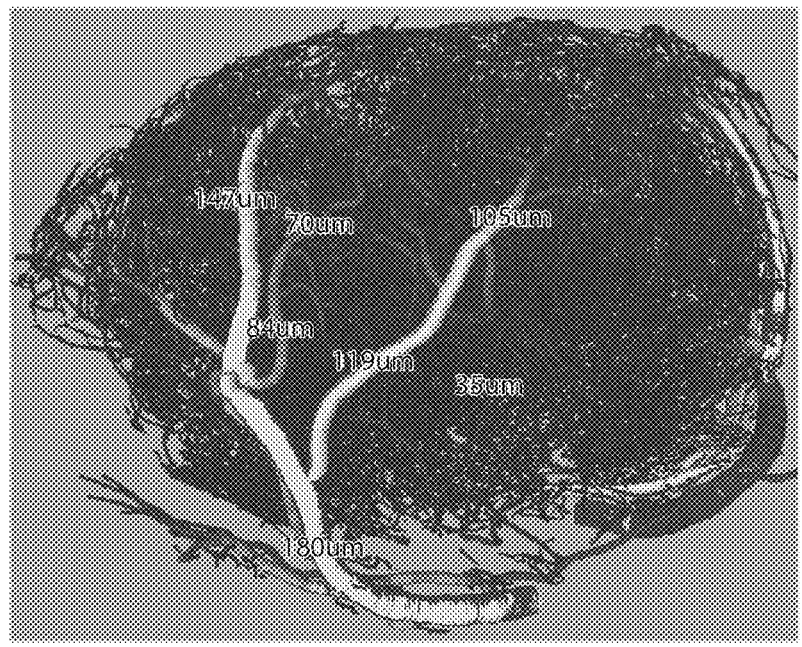
Figure 40:
FIG. 40 illustrates a close-up view of 3D segmented and reconstructed tumor vasculature of the tumor in FIGS. 37-39.
Figure 41:
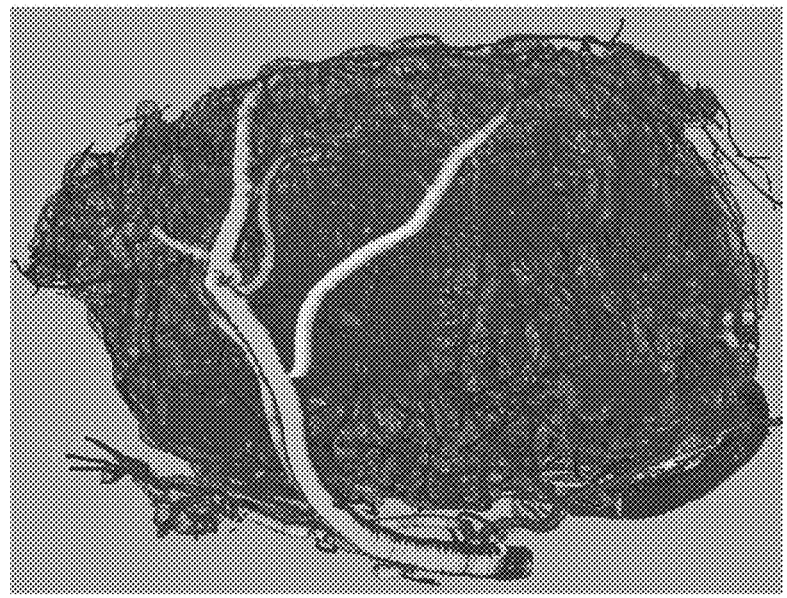
FIGS. 41-42 illustrate different views of 3-D wrapped tumor vasculature.
Figure 42:
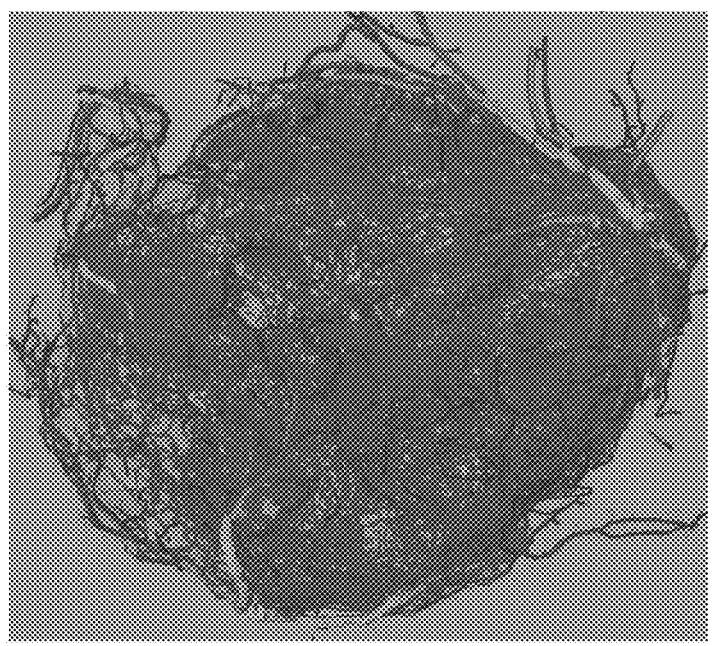
Figure 43:
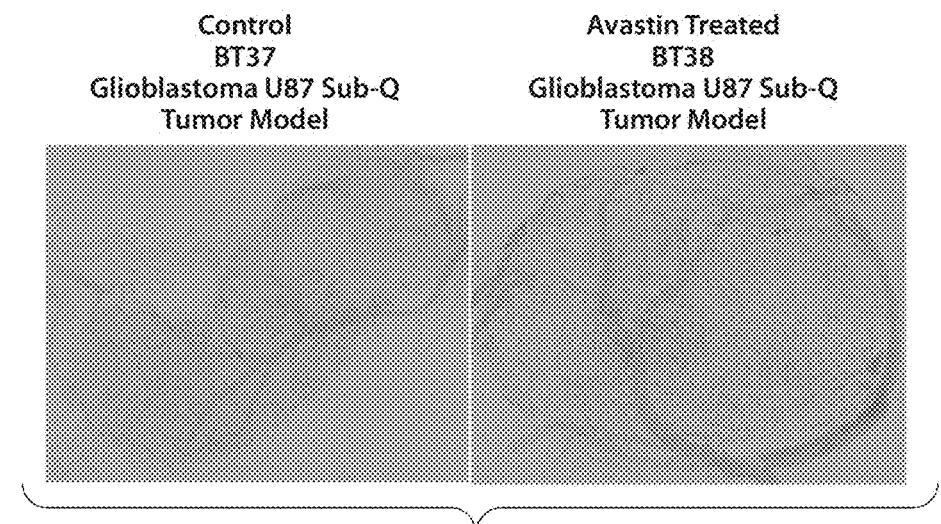
FIG. 43 illustrates examples of micro-CT raw view images.

The assessment of a microvascular density biomarker indicating vascular hot spots as regions of high microvascular density and necrotic regions as regions of low microvascular density in a tumor is exemplified in FIGS. 35-52. An exemplary tumor is shown in situ in FIG. 35 and an exemplary X-ray image of the same tumor is shown in FIG. 36. 3D model images of the same tumor, representing an exemplary result of methods of vascular analysis and modeling according to methods provided by aspects of this invention is shown in FIGS. 37 and 38. The 3D model of the tumor allows for direct measurement and annotation of vascular diameters, exemplified in FIGS. 39 (whole tumor) and 40 (close-up). FIGS. 41 and 42 are exemplary images of a 3D tumor wrap of the same tumor.

Figure 44:
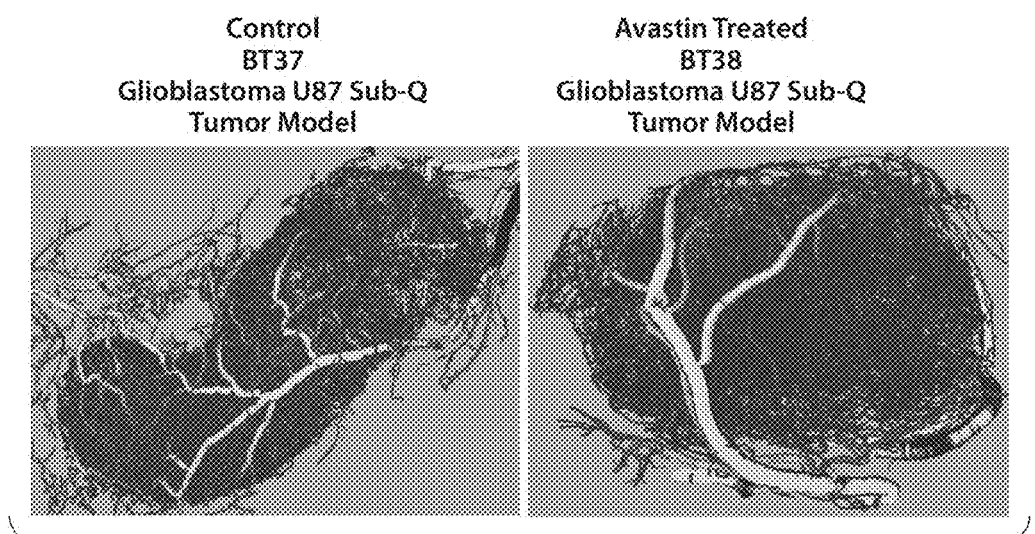
FIG. 44 illustrates a 3-D segmented tumor vasculature of a control and an avastatin-treated glioblastoma.
Figure 45:
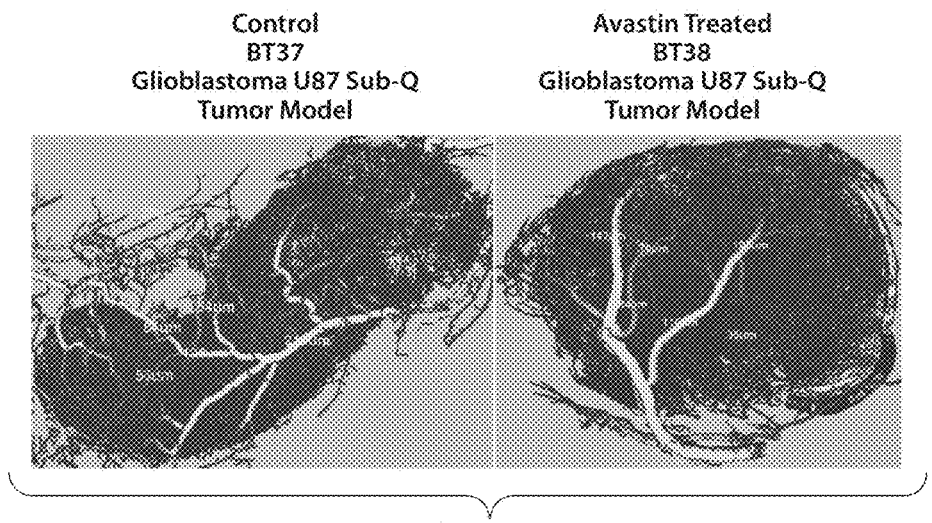
FIG. 45 illustrates a 3-D segmented tumor vasculature of a control and an avastatin-treated glioblastoma showing exemplary measured vessel diameters.
Figure 46:
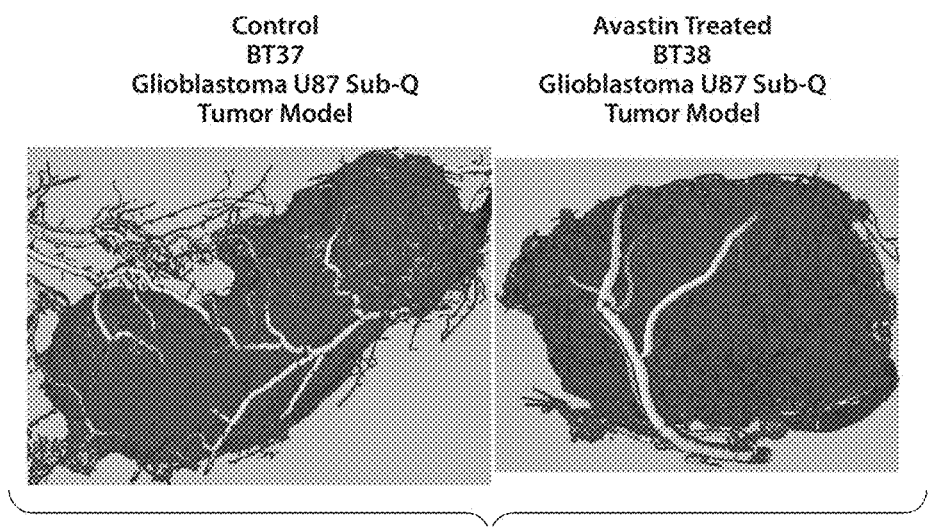
FIGS. 46-47 illustrate different views of 3-D wrapped tumor vasculature of a control and an avastatin-treated glioblastoma.
Figure 47:
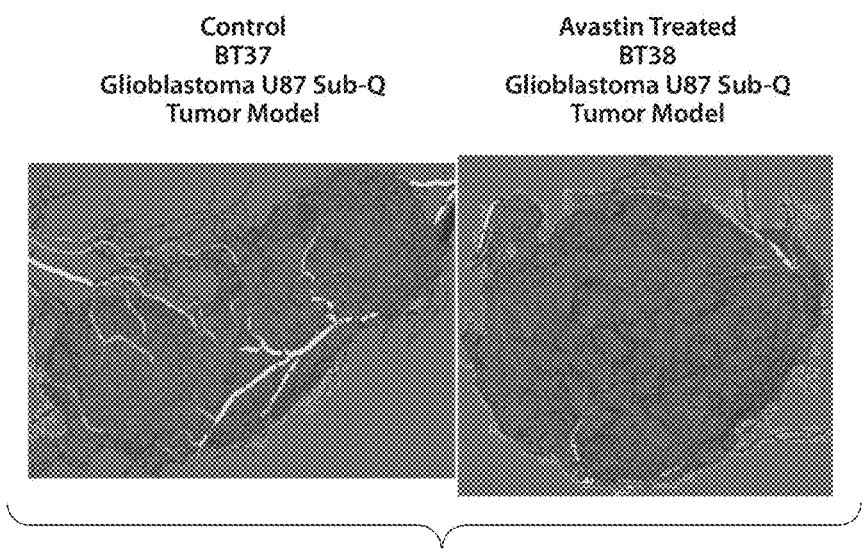
Figure 48:
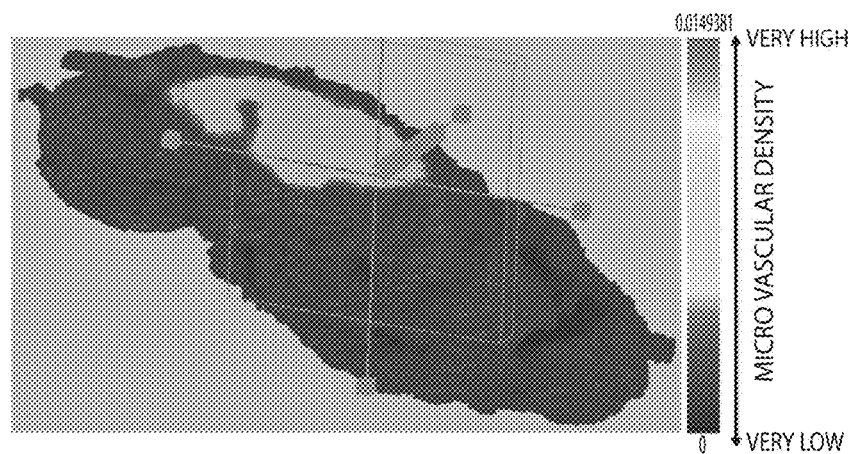
FIGS. 48-52 illustrate continuous 3-D microvascular density maps, using virtual histology showing different tumor cross-sections.
Figure 49:
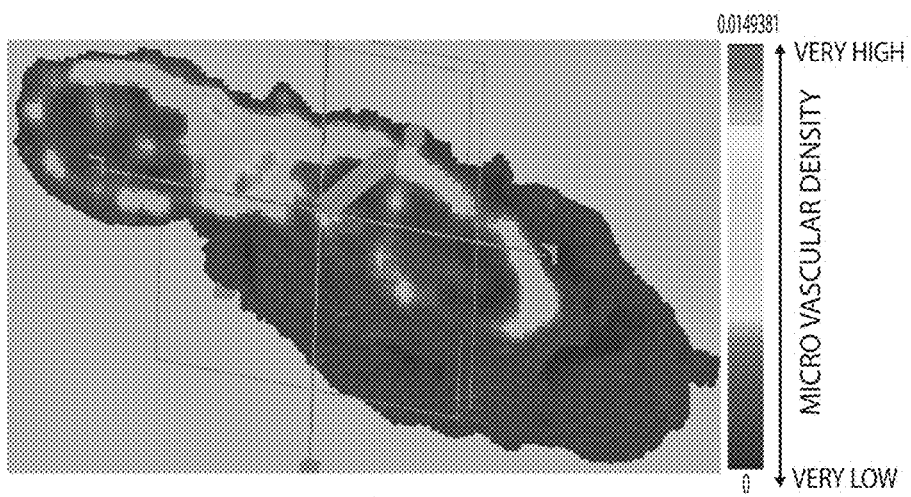
Figure 50:
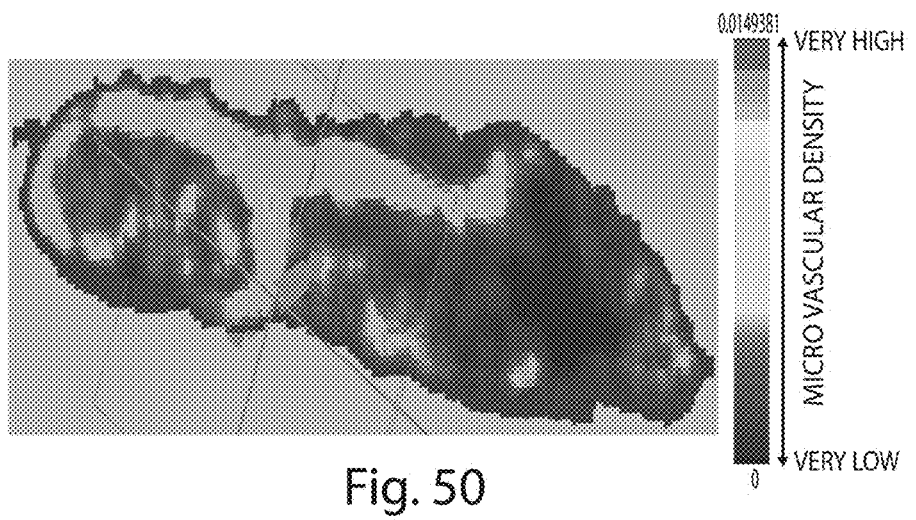
Figure 51:
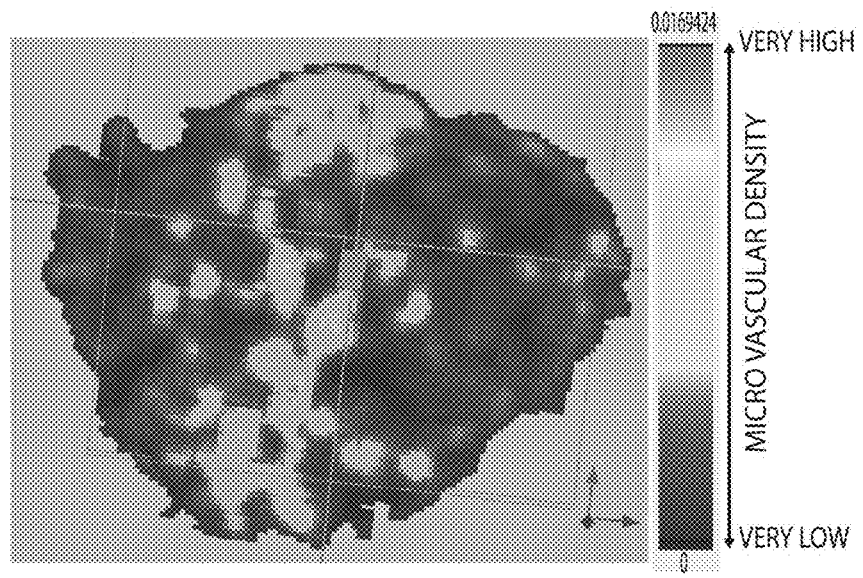
Figure 52:
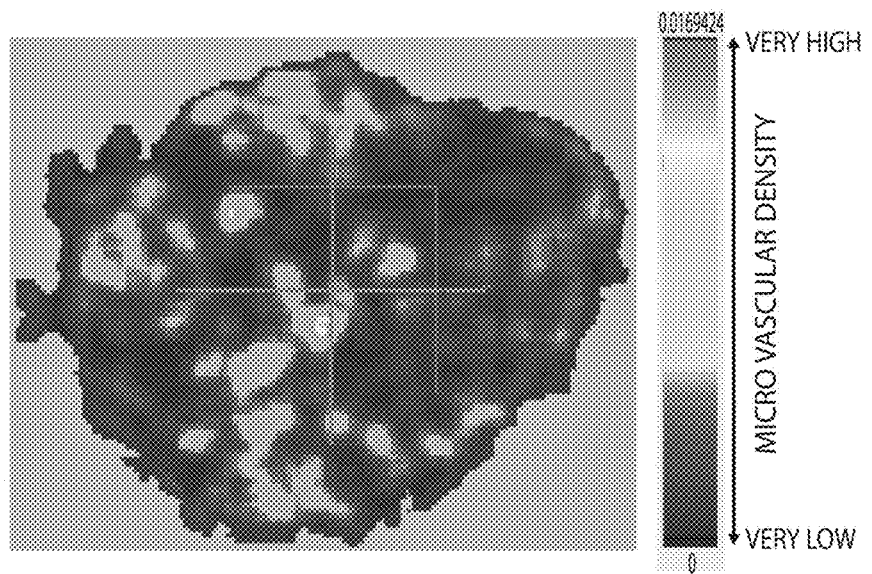
Figure 53:
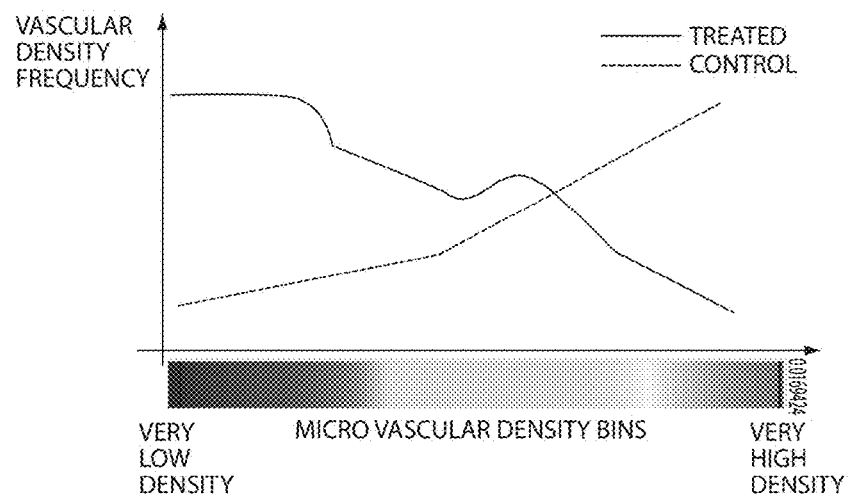
FIG. 53 illustrates the frequency of vascular density bins in a control and an Avastin-treated tumor.

FIGS. 43-54 demonstrate an exemplary assessment of tumor vasculature and use of vascular information obtained by methods provided according to some aspects of this invention to identify substructures, for example, vascular hotspots, within a given tissue, for example, a tumor. X-ray images of a control tumor and an Avastin-treated tumor are shown side by side in FIG. 43. FIG. 44 shows 3D models of the vasculature of the same tumors and FIG. 45 shows exemplary vascular diameters measured using the model. FIGS. 46 and 47 show exemplary tumor wraps of the same control and Avastin-treated tumors. FIGS. 48-52 exemplify visualization of the distribution of microvascular density within two exemplary tumors. A comparison of the frequency of microvascular density bins between a control and a treated tumor is shown in FIG. 53, demonstrating different microvascular density bin distribution in the control and treated tumor.

It should be appreciated that the level of vasculature may be evaluated using any appropriate metric, for example, as described herein. In some embodiments, the blood vessels may be characterized and grouped for analysis (e.g., for binned analysis). In some embodiments, one or more structural features (e.g., density-related, volume-related, shape-related, or any combination thereof) may be associated with each voxel in an image or reconstructed model of a vasculature within a tumor (e.g., within a tumor wrap). The voxels then may be analyzed for therapeutic, evaluative (e.g., research), and/or therapeutic applications as described herein. For example, the number (for example, absolute or relative numbers, e.g., percentage) or frequency of voxels having different levels of different structural features may be assessed and compared under different conditions (e.g., different treatment levels, different treatment regimens, etc., or any combination thereof). In some embodiments, the number (for example, absolute or relative numbers, e.g., percentage) or frequency of voxels in different tissues (e.g., diseased, healthy, etc.), optionally under different conditions, may be compared as described and illustrated herein.

Figure 54:
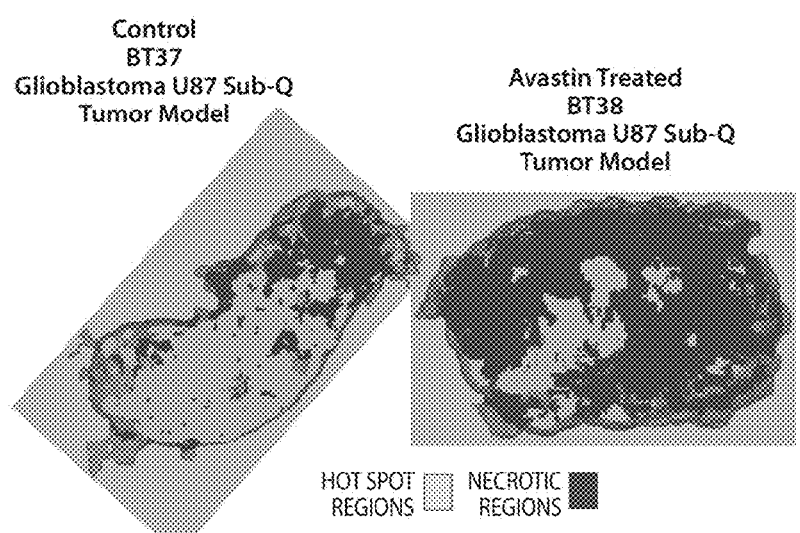
FIG. 54 illustrates visualization of necrotic regions and vascular hotspots in a control and an avastatin-treated tumor.
Figure 55:
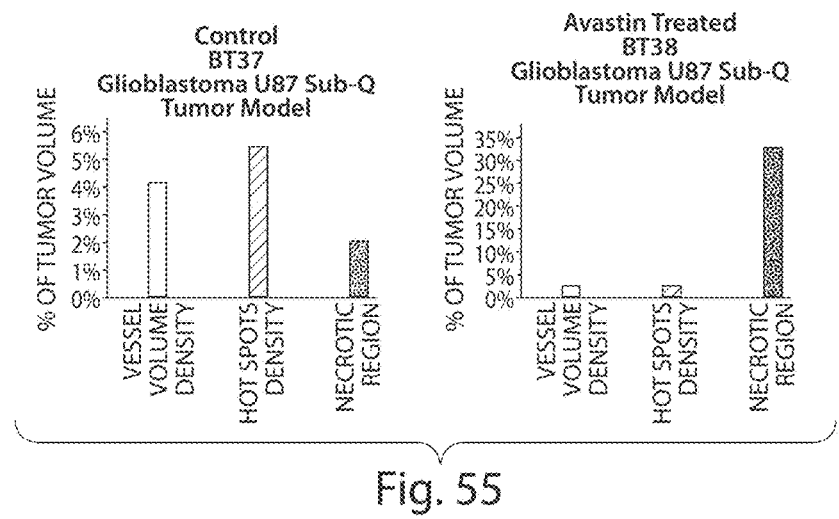
FIG. 55 illustrates the quantification of vascular biomarkers (vascular hotspots and necrotic regions) in control and an avastatin-treated tumors.
Figure 56:
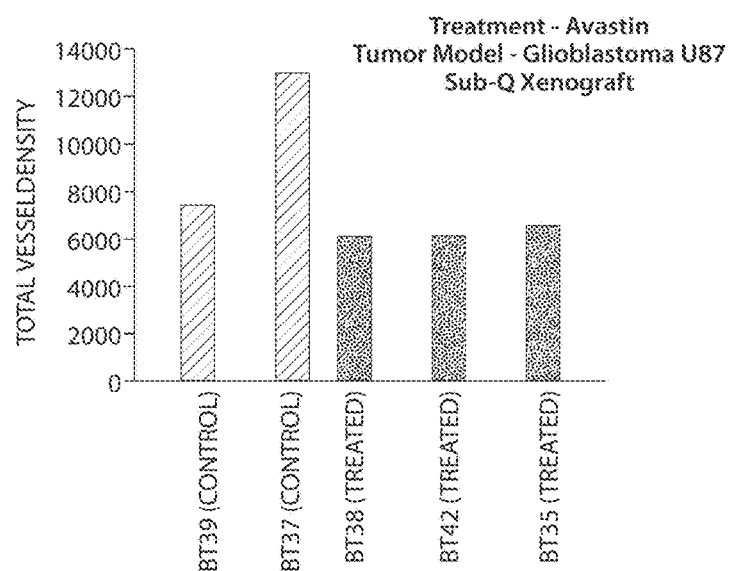
FIG. 56 illustrates tumor microvascular density (TMVD) in individual tumors.
Figure 57:
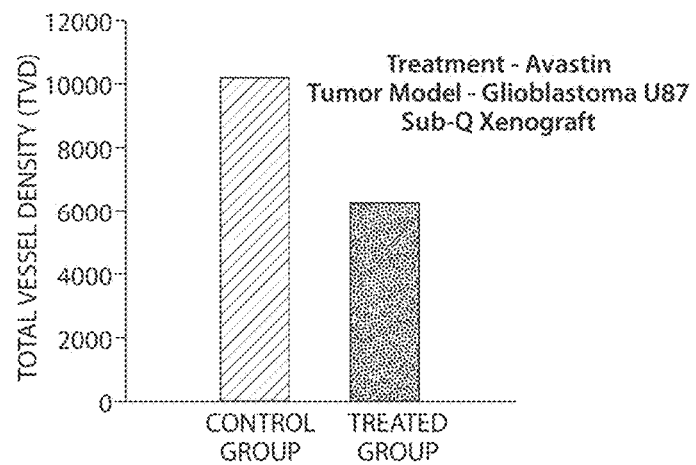
FIG. 57 illustrates mean tumor microvascular density (mTMVD) in individual tumors.
Figure 58:
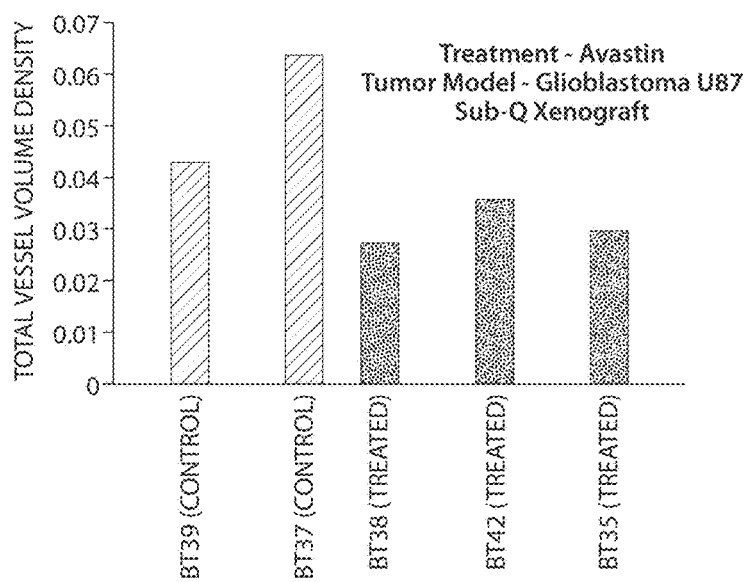
FIG. 58 illustrates tumor vascular volume density (TVVD) in individual tumors.
Figure 59:
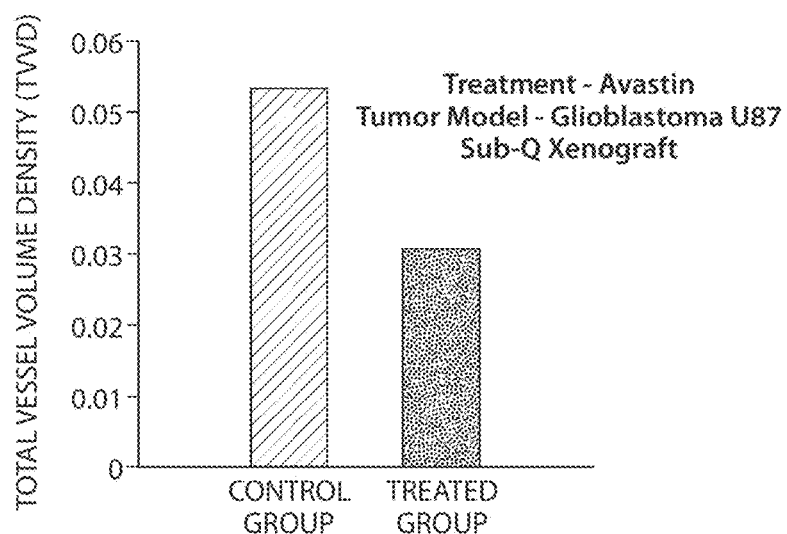
FIG. 59 illustrates mean tumor vascular volume density (mTVVD) in individual tumors.
Figure 60:
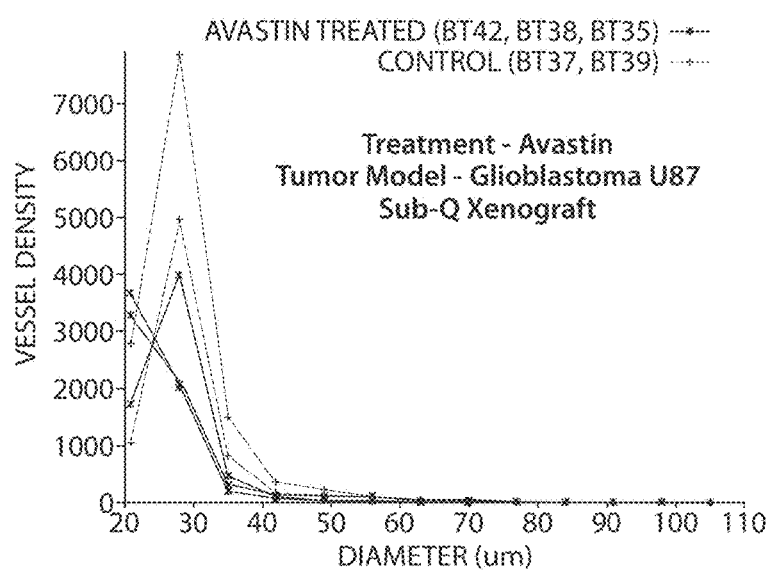
FIG. 60 illustrates BMVD in individual tumors for vessel diameters of 20-110 micrometers.
Figure 61:
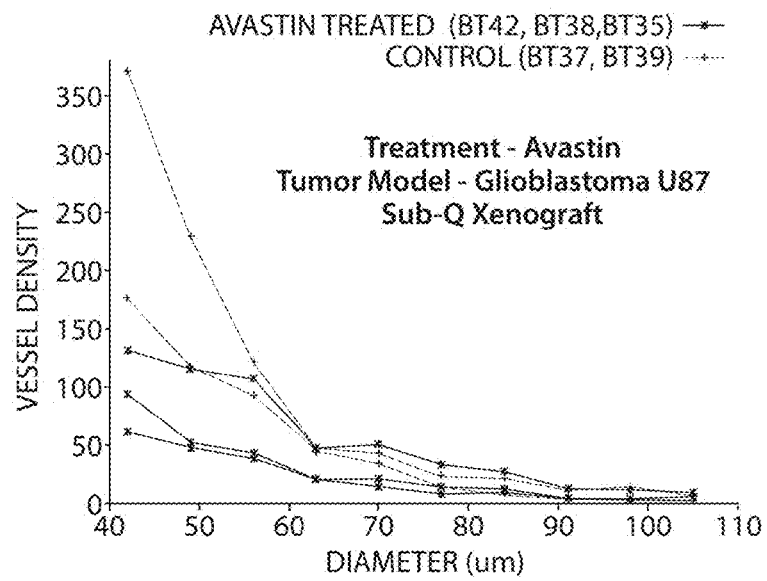
FIG. 61 illustrates binned micro-vascular density (BMVD) in individual tumors for vessel diameters of 40-110 micrometers.
Figure 62:
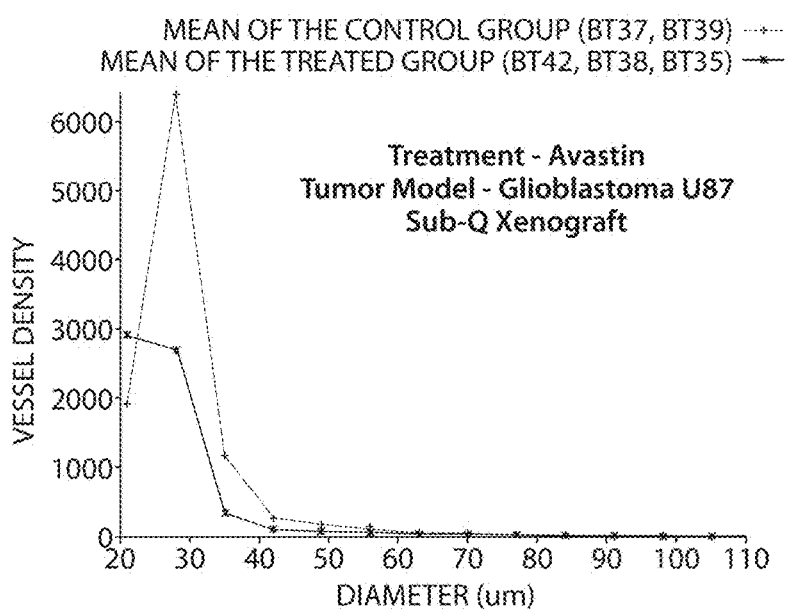
FIG. 62 illustrates mBMVD in individual tumors for vessel diameters of 20-110 micrometers.
Figure 63:
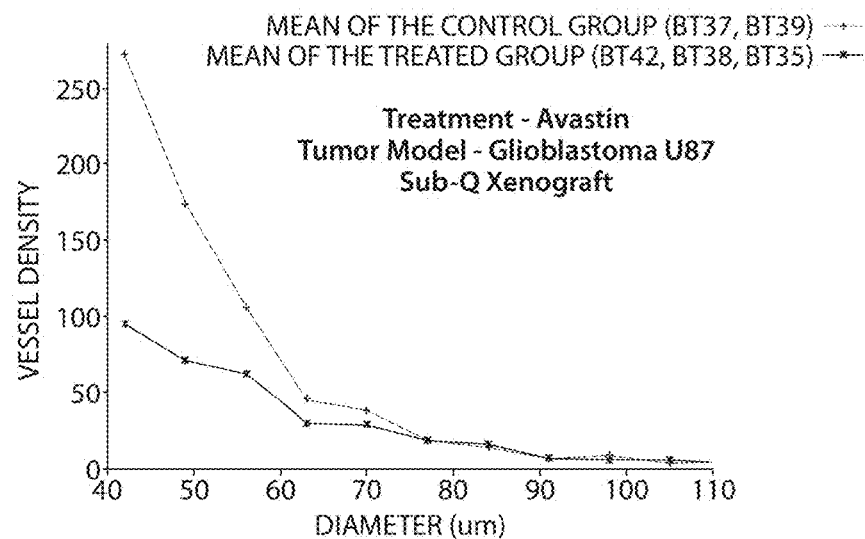
FIG. 63 illustrates mBMVD in individual tumors for vessel diameters of 40-110 micrometers.
Figure 64:
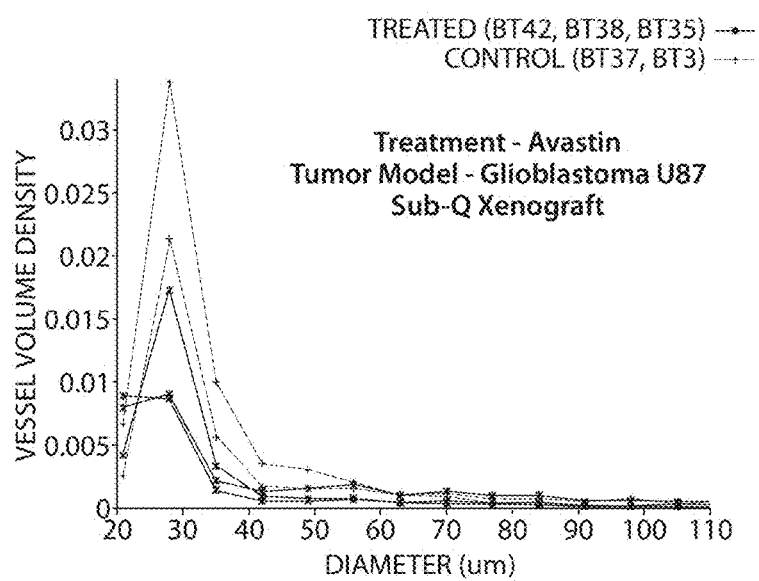
FIG. 64 illustrates BMVVD in individual tumors for vessel diameters of 20-110 micrometers.
Figure 65:
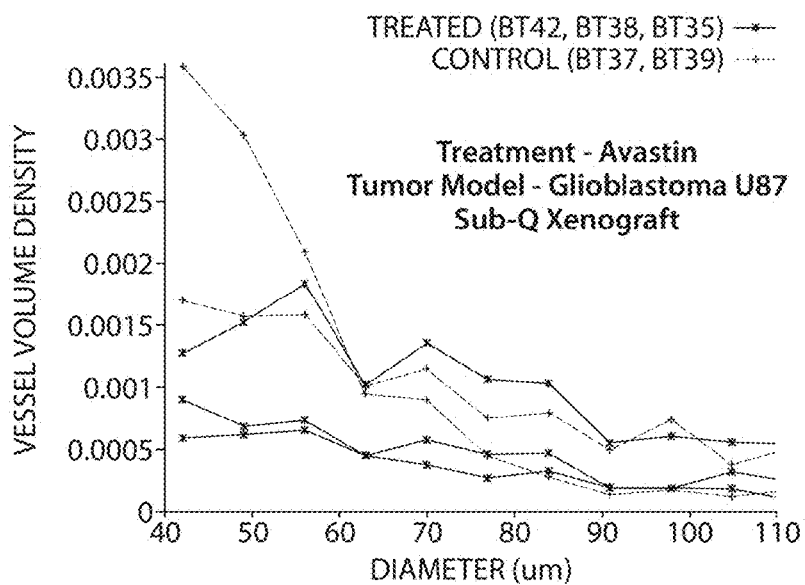
FIG. 65 illustrates BMVVD in individual tumors for vessel diameters of 40-110 micrometers.
Figure 66:
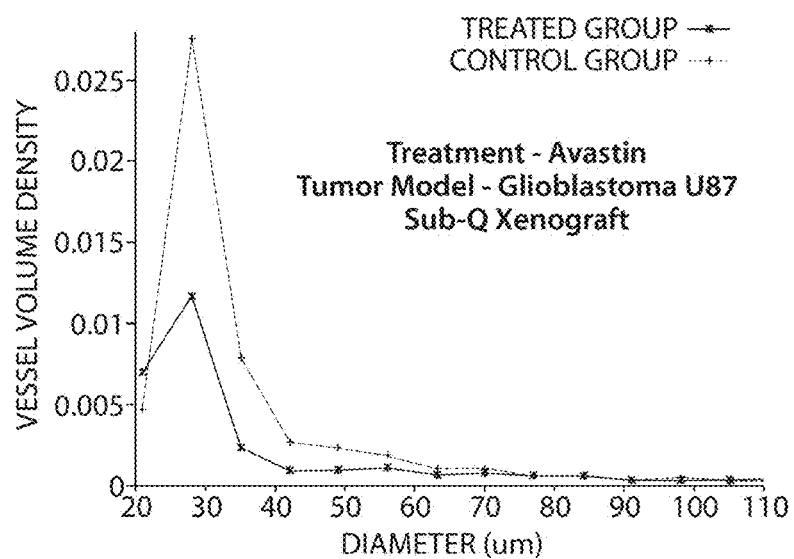
FIG. 66 illustrates mBMVVD in individual tumors for vessel diameters of 20-110 micrometers.
Figure 67:
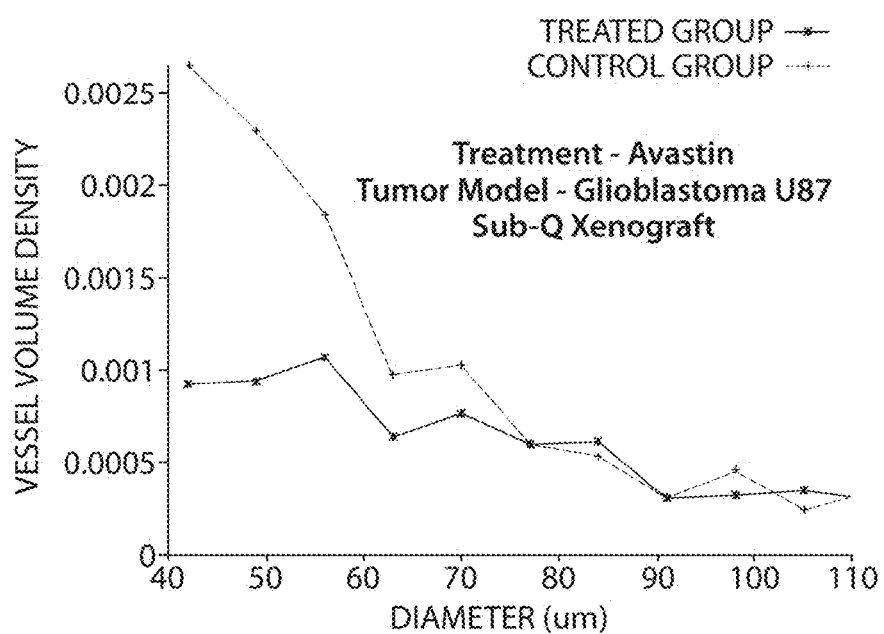
FIG. 67 illustrates mBMVVD in individual tumors for vessel diameters of 40-110 micrometers.

In some embodiments, the assessment of vascular hot spots and/or necrotic regions within a diseased tissue, for example a malignant tumor, may be used in the evaluation of a treatment targeting said diseased tissue, for example the administration of a chemotherapeutic agent. FIG. 54 exemplify a comparison of vascular hot spots and necrotic regions in glioblastoma treated with Avastin to vascular hot spots and necrotic regions in non-treated control glioblastoma. A qualitative comparison of a vascular density related biomarker, as shown in FIG. 55, may be used to examine the changes in vascular density effected by a treatment. In the example depicted in FIG. 55, Avastin treatment of a glioblastoma led to a significant increase in necrotic region volume in a significant decrease in both vessel volume density and hot spot density. Assessment of an exemplary vascular density related biomarker, total vessel density (number of vessels per given volume), in Avastin-treated glioblastoma and untreated controls is depicted in FIG. 56. Assessment of another exemplary vascular density related biomarker, mean vessel density (average number of vessels over a number of volume units, for example defined by the boundary of a tumor), in Avastin-treated glioblastoma and untreated controls as depicted in FIG. 57. Assessment of an exemplary vascular density related biomarker, total vessel volume density (number of voxels belonging to a vessel within a given volume), in Avastin-treated glioblastoma and untreated controls is depicted in FIG. 58. Assessment of another exemplary vascular density related biomarker, mean vessel volume density (average number of voxels belonging to a vessel within a number of volume units, for example defined by the boundary of a tumor), in Avastin-treated glioblastoma and untreated controls as depicted in FIG. 59. In some embodiments, a boundary of a tissue, for example a tumor, are determined based on vascular imaging and modeling data, and a subsequent assessment qualifying a voxel within those boundaries is carried out. In some embodiments, a biomarker is penalized in a plurality of such qualified voxels. For example, the boundary of a solid tumor may be determined based on the abnormal vasculature associated with malignant tissue, for example by "tumor-wrap", and vascular density related biomarkers may be assessed for tissue within that boundary.

Some non-limiting examples of vascular anatomy biomarkers are vascular tortuosity, vascular curvature, and vascular diameter. Some non-limiting examples of vascular tortuosity biomarkers according to some aspects of this invention are 2D vascular tortuosity or 3D vascular tortuosity, (for example expressed as amount of twist over a given blood vessel length), total amount of blood vessel tortuosity within a given tissue volume, distribution of blood vessel tortuosity bins within a given tissue volume, or mean blood vessel tortuosity over a given tissue volume.

Some non-limiting examples of vascular curvature biomarkers according to some aspects of this invention are extrinsic curvature, extrinsic curvature, distribution of curvature bins within a given tissue volume, total amount of blood vessel curvature within a given tissue volume, or mean blood vessel curvature over a given tissue volume.

Some non-limiting examples of vascular diameter biomarkers according to some aspects of this invention are vascular taper (for example change in diameter over a given blood vessel length), vascular diameter variation, distribution of vascular diameter bins within a given tissue volume, or frequency of a given vascular diameter bin within a given tissue volume.

Some aspects of this invention relate to identifying the functional vasculature of a given tissue. The term "functional vasculature", as used herein, refers to any type of blood vessel actually transporting blood. Blood vessels not transporting blood, for example embolized vessels, are not part of the functional vasculature. The term functional vasculature further includes leaky blood vessels. Leaky blood vessels are often associated with malignant tissues, such as tumors. The functional vasculature of a given tissue can be identified, for example, by imaging the vasculature in that tissue using a contrast agent that is transported in blood supplied to that tissue.

Some aspects of this invention relate to defining the boundary of a given tissue or tissue type, for example a diseased tissue, such as a tumor or a malignant tissue, based on a vascular biomarker. In some embodiments, a control or reference biomarker value is compared to the actual biomarker value measured in the examined tissue. In some embodiments, a deviation of the actual biomarker value from the control or reference biomarker value above a certain threshold is used to define the boundary of the respective tissue. For example, if the value of a given vascular biomarker, for example the frequency of a given vascular diameter bin in a given tissue volume deviates, for instance, about 10%, about 20%, about 30%, about 40%, about 50%, about 60%, about 70%, about 80%, about 90%, about 100%, about 150%, about 200%, about 250%, about 300%, about 400%, about 500%, about 750%, about 1000%, about 2000%, about 5000%, about 10,000%, and 50,000%, or about 100,000% from a control or reference biomarker value, then the given tissue volume may be identified, at least partially, as a diseased tissue, such as a tumor or a malignant tissue. Some biomarkers provided by aspects of this invention may be used to determine the boundary of a tissue, for example a solid tumor. Establishing the boundary of a tumor, a so-called "tumor wrap", may be used as an accurate definition of the volume of tumor tissue as well as the 3-D position of a tumor.

Some comparisons of vascular biomarker assessments according to some aspects of this invention in control glioblastoma and glioblastoma treated with Avastin are displayed in FIGS. 55-67. It should be appreciated, that the biomarkers related to by some aspects of this invention may be useful in a wide variety of diagnostic and therapeutic modalities and applications, some non-limiting examples of which are described herein.

It should be appreciated that one or more of the biomarkers described herein may be used to identify (e.g., automatically) one or more diseased regions (e.g., tumors) for diagnostic, prognostic, and/or therapeutic purposes.

In some embodiments, imaging may be performed using any high-resolution imaging technology, such as, for example, CT or MRI. In some embodiments, imaging may be performed, for example, in vivo, in vitro, in situ, and/or ex vivo. In some embodiments, a contrast agent may be used for imaging. In some embodiments, a casting agent may be used for imaging. In some embodiments, a vascular cast from a tissue of interest, for example a tumor, may be used for imaging. In some embodiments imaging data may be used to generate a 3D vasculature model of a given tissue. In some embodiments, 3D vasculature modeling may be performed generating a poker-chip representation of a vasculature as described in detail herein. Some aspects of this invention relate to the use of this modeling information in therapeutic and/or diagnostic applications. In some embodiments, a 2D "virtual histology" image may be created, representing a section of a 3D model. Vascular metrics and biomarkers as provided herein may be measured in such 2D virtual histology images, in 3D models as provided herein, or by a comparison of both.

In some embodiments, vascular structure data may be binned, for example by diameter etc., for analysis. In some embodiments, vascular structure data may be analyzed by continuous mapping of vascular features.

Example 4: Vascular Biomarkers in Diagnosis and Therapy

Some aspects relate to methods of analyzing a geometric feature of a blood vessel and correlating such a feature with a biological process, condition, or disease. Some geometric features of blood vessels may be used as biomarkers indicative of particular biological processes, conditions, and/or diseases.

Some aspects of this invention relate to methods for monitoring the effect of a clinical intervention in a subject, for example the administration of a dose of ionizing radiation, or the administration of a drug or a therapeutic composition, for example an anti-angiogenic drug or a chemotherapeutic agent. In some embodiments, the effect of a clinical intervention in a subject may be monitored by assessing a vascular biomarker in a tissue of said subject before, during, and/or after said clinical intervention is performed. In some embodiments, results from vascular biomarker assessment in a subject at different time points may be compared. Such comparisons may be used, for example, to determine the efficacy of a clinical intervention. In some embodiments, the results of monitoring the effect of a clinical intervention in a subject by assessing of vascular biomarker may be used as the basis for an alteration in a clinical intervention, for example an adjustment in the dosage of an administered drug, a change in the type of drug being administered, or an adjustment the dosage of ionizing radiation. In some embodiments, the duration of a clinical intervention may be determined on the basis of monitoring a vascular biomarker in a target tissue. In some embodiments, a clinical intervention may be carried out until a desired effect, for example a change in the value of a vascular biomarker, is achieved. For example, an antiangiogenic drug may be administered to a subject having a tumor until a desired effect has been observed by monitoring a vascular biomarker in the tumor tissue.

Non-limiting examples of desired effects are a decrease in total tumor microvascular density (TMVD) or mean TMVD of about 10%, about 20%, about 30%, about 50%, about 60%, about 70%, about 80%, about 90%, about 99%, about 100%, and/or to a level associated with tissue necrosis or tissue hypoxia, or blood vessel, for example mother vessel, embolization.

In some embodiments, the effect of a clinical intervention on the vasculature of a non-target tissue may be monitored by assessing a vascular biomarker in said tissue. For example, vasculature abnormalities or changes in vasculature patterns may be detected in non-diseased tissue as a result of a clinical intervention. In some embodiments, the effect of an exposure to a vasculature modifying agent, for example a toxin, may be monitored by assessing a vascular biomarker in a tissue of a subject exposed or suspected to be or to have been exposed to such an agent.

Some aspects of this invention relate to screening methods for identifying a therapeutic agent, for example a vasculature modifying agent or method. In some embodiments a therapeutic agent, for example a vasculature modifying agent or method useful in therapeutic interventions targeting tumors, for example an anti-angiogenic drug, may be identified using methods related to by some aspects of this invention. In some embodiments, the effect of a candidate therapeutic agent or method on the vasculature of a diseased tissue in an animal model of disease may be monitored by assessing a vascular biomarker before, during, and/or after administering said candidate therapeutic agent or method. For example, a candidate anti-angiogenic agent, for example a drug, may be administered to an animal subject carrying a specific type of tumor, for example a mouse tumor model for glioblastoma, and the effect of said candidate agent on the vasculature of a tumor in said subject may be assessed. In some embodiments, the effect of said candidate therapeutic agent or methods on the vasculature of a diseased tissue may be compared to the effect of a known therapeutic agent or method on the vasculature of a diseased tissue. The effect of a drug or agent on vasculature may be evaluated by assessing a biomarker according to some aspects of this invention. For example, if the effect of a candidate treatment (e.g., a candidate compound) on the biomarker is similar or greater to the effect of a control compound (e.g., Avastin) then the candidate compound may be identified as an effective candidate compound that may be selected for further analysis and/or use in therapy. In contrast, in some embodiments, if the candidate compound is significantly less effective than the control compound, then the candidate compound may be removed from further study. However, it should be appreciated that a different target level of effectiveness may be selected (and correspondingly different thresholds may be used) for different applications. Some aspects of this invention relate to screening methods assessing a plurality of vascular biomarkers during an evaluation of a candidate vasculature modifying agent, thus creating a vascular biomarker modification profile for said candidate agent. In some embodiments, a drug exhibiting a specific vascular biomarker modification profile may be matched up with a specific target tissue, for example a specific type of tumor.

In some embodiments, aspects of this invention relate to methods employing the imaging and modeling technology, for example using poker-chip modeling techniques, to assess vasculature biomarkers to normal and diseased tissues of subjects and to define the boundary of a given tissue or tissue type, for example a diseased tissue, such as a tumor or malignant tissue. The high resolution of the imaging and modeling technology as described in detail herein allows for the definition of tissue boundaries at micrometer accuracy.

Some aspects of this invention relate to defining with high accuracy the location of a target structure of interest within a given tissue based on a vascular biomarker. Some aspects of this invention provide methods for identifying the precise location of a target structure within an abnormal tissue, for example a mother blood vessel of a tumor, which connects the vasculature of tumor to the surrounding tissue. Other non-limiting examples of structures of interest are vessels of a given vascular hierarchy bin, vascular hotspots (e.g., within a tumor), and necrotic regions within a tissue (e.g., a tumor).

Some aspects of this invention relate to providing precise guidance (e.g., image-guided) for beam targeting during radiation therapy, for example during radiosurgery, using methods provided by some aspects of this invention, for example methods relating to defining the exact boundaries of a target tissue, for example malignant tissue associated with a tumor, or defining the exact location of structures of interest within a target tissue, for example of mother vessels or hotspots.

In some embodiments, a therapy (e.g., a radiotherapy) is targeted to one or more biomarkers associated with a disease or condition as described herein. Some aspects of this invention provide methods combining real-time, high-resolution image guided beam positioning and/or targeting during radiosurgery (e.g., stereotactic radiosurgery) to deliver high doses of ionizing radiation with high accuracy (e.g., submillimeter accuracy) to a target tissue, for example a tumor or a tumor structure, such as a mother blood vessel or a vascular hotspot of a tumor, while sparing sensitive neighboring structures of the target tissue. In some embodiments, a plurality of beams of ionizing radiation is targeted to intersect, at least partially, at a structure identified by methods provided by some aspects of this invention. For example, a 3-D location of a tumor may be defined with high accuracy in a subject diagnosed to have a tumor using methods provided by aspects of this invention, and relevant 3-D coordinates, for example tumor location, tumor volume, and tumor boundary, may be used as the basis for 3-D targeting of a beam or a plurality of beams of ionizing radiation. In some embodiments, one or more beams are targeted to (or targeted to intersect at) a structure such as a mother vessel, a feeder vessel, a large vessel, a tumor hotspot, a plurality of any such vessels or hotspots, or a combination thereof. It should be appreciated, that, based on the technical limitations of beam manipulation technology, a beam targeted at a specific structure may nonetheless deliver some ionizing radiation to areas outside said specific structure. Similarly, it should be appreciated, that the intersection area and/or intersection volume of a plurality of beams targeted to intersect at a specific structure may include an area and/or volume outside said specific structure. In some embodiments, a plurality of beams of ionizing radiation may be targeted to only partially intersect at a structure smaller than the beam diameter, thus creating a high dosage area and/or volume a diameter smaller than the actual beam diameter. It should be appreciated that methods of the invention associated with the targeting of a vasculature structure can be used to embolize or cauterize a blood vessel or a plurality of blood vessels that feed a tumor.

In some embodiments, aspects of the invention also can be used to optimize a therapeutic treatment for a patient. The extent of disease progression or regression can be monitored in response to different treatment types or dosages, and an optimal treatment can be identified. The optimal treatment may change as the disease progresses. The effectiveness of the treatment over time can be monitored by analyzing changes in disease-associated patterns (e.g., individual structural features or distributions) using the aspects of the present invention described herein.

In one embodiment, a first therapy can be administered and its effectiveness on slowing, stopping, or reversing abnormal blood vessel growth can be monitored either irregularly or at certain time intervals (e.g., daily, weekly, monthly, or other time intervals). In some embodiments, if a first therapeutic regimen does not have a desired effect on disease progression, a second therapeutic regimen can be evaluated. Similarly, additional therapeutic regimens can be evaluated on a patient-by-patient basis. Additionally, the invention can be used to optimize a chosen therapeutic regimen (e.g., optimize dosage, timing, delivery, or other characteristic of a drug or other treatment) by monitoring the effect of minor therapeutic changes and using the conditions that appear to be most effective for the condition and the patient.

When looking at the therapeutic effectiveness of a treatment, disease-specific parameters may be monitored. Of course, all parameters can be obtained and only a subset reviewed. However, it may be more efficient to simply obtain (a representation of) only those parameters that characterize the disease.

According to aspects of the invention, patterns (e.g., individual structural features or distributions) that are used to detect angiogenic vasculature and other abnormal blood vessels also can be used to monitor a disease response to treatment. For example, the total vascularity or any other volumetric analysis of angiogenic or other diseased vasculature, and the distribution of vessel size (e.g., a ratio of small to large blood vessels) can be used independently or together as indicators of disease progression or regression. In general, microvasculature disappears before macrovasculature if an anti-angiogenic treatment (or other disease treatment) is effective. Therefore, an effective treatment results in a shift in the distribution of blood vessel sizes towards larger vessels. An index of anti-angiogenic activity can be scored as either a loss of small blood vessels or a shift of observed blood vessels towards a single size (or both).

In another aspect, the parameters can be (or include) changes over time. For example, a structure present at a second time can be compared to a structure present at a first time. In one embodiment, a disease may be tracked pre-therapy and/or post-therapy. Naturally, additional time points can be used. The time points may depend on the condition being observed (e.g., is it the progression of a disease that is already identified, is it the screening of patient(s) over time). Time periods can be daily, weekly, monthly, annual, or shorter, intermediate or longer time periods. Time intervals may be a series of regular time periods. However, other time intervals may also be useful. In one embodiment, a patient-specific baseline is established and monitored over time. For example, vasculature changes in the colon, breast, or other tissue or organ can be monitored periodically.

In one aspect of the invention, a type of treatment may be determined by the degree or extent of abnormal vascular structures (e.g., angiogenesis) that is detected at one or more suspected disease loci (e.g., cancerous loci). For example, if a suspected cancerous locus or metastasis is pre-angiogenic or associated with early stage angiogenesis, it may be appropriate to monitor the locus without any form of treatment. However, an appropriate therapy may involve the administration of one or more angiogenesis inhibitors to prevent the formation of any new vasculature. If a suspected cancerous locus or metastasis is associated with mid-stage angiogenesis, an appropriate therapy may be the administration of one or more angiogenesis inhibitors. A patient with mid-stage angiogenesis at a suspected locus also should be monitored so that any further blood vessel development can be treated more aggressively. If a suspected cancerous locus or metastasis is associated with late stage angiogenesis, an appropriate treatment may involve at least one or more of chemotherapy (e.g., cytotoxic chemotherapy and/or hormone-based chemotherapy), radiation, surgery, and/or treatment with one or more angiogenesis inhibitors. However, it should be appreciated that any of the above treatment options may be used to treat a patient with any one or more lesions associated with any degree of angiogenesis.

Examples of angiogenesis inhibitors include but are not limited to 2-methoxyestradiol (2-ME), AG3340, Angiostatin, Angiozyme, Antithrombin III, VEGF inhibitors (e.g., Anti-VEGF antibody), Batimastat, bevacizumab (Avastin), BMS-275291, CAI, 2C3, HuMV833 Canstatin, Captopril, Cartilage Derived Inhibitor (CDI), CC-5013, Celecoxib (CELEBREX®), COL-3, Combretastatin, Combretastatin A4 Phosphate, Dalteparin (FRAGIN®), EMD 121974 (Cilengitide), Endostatin, Erlotinib (TARCEVA®), gefitinib (Iressa), Genistein, Halofuginone Hydrobromide (TEMPOSTATIN™), Id1, Id3, IM862, imatinib mesylate, IMC-IC11 Inducible protein 10, Interferon-alpha, Interleukin 12, Lavendustin A, LY317615 or AE-941 (NEOVASTAT™), Marimastat, Maspin, Medroxpregesterone Acetate, Meth-1, Meth-2, Neovastat, Osteopontin cleaved product, PEX, Pigment epithelium growth factor (PEGF), Platelet factor 4, Prolactin fragment, Proliferin-related protein (PRP), PTK787/ZK 222584, ZD6474, Recombinant human platelet factor 4 (rPF4), Restin, Squalamine, SU5416, SU6668, SU11248 Suramin, Taxol, Tecogalan, Thalidomide, Thrombospondin, TNP-470, TroponinI, Vasostatin, VEG1, VEGF-Trap, and ZD6474.

Some embodiments may include a method of selecting a subject for treatment and/or selecting a treatment or a course of therapy based on the analysis of certain in situ vascular structures. A method may involve analyzing in situ vascular structure(s) in a human subject to obtain, for example, a score. The score may be compared to a control score (e.g., in an apparently healthy population) or to a previous score from a previous analysis on the same subject. The treatment or the course of therapy may be based on such a comparison. In some embodiments, obtaining an analysis of vascular structures is repeated so as to monitor the human subject's response to therapy over time. In some embodiments of this aspect of the invention, the method further comprises measuring a second index of disease in the human subject wherein deciding on the treatment or course of therapy is also based upon the measurement of said second index.

In certain embodiments, patients having a tumor that is under-vascularized (e.g., one that shows signs of necrosis) may be selected for treatment with one or more anti-angiogenic compounds. Under-vascularized tumors may be identified as those that have a low density of blood vessels, or for which the blood vessel diameters are low (e.g., below a threshold number typical of vascularized tumors).

Aspects of the invention also may include monitoring the effectiveness of a therapy by monitoring the presence of blood vessel patterns or features over time. For example, the progressive loss of blood vessels in a tumor in response to treatment may be a sign that a therapy is effective. In contrast, the absence of any impact on vascularization may be an indicator that a treatment is not being effective in a patient and that an alternative therapy should be considered or used.

It should be appreciated that some or all of the therapeutic aspects of the invention can be automated as described herein.

Example 5: Surrogate Markers

In another embodiment, aspects of the invention can be used in screens of compound libraries or to validate candidate compounds for treating diseases associated with abnormal internal structures (e.g., abnormal tubular networks). Aspects of the invention allow efficient high throughput analyses of internal structural changes. These changes can act as surrogate markers (biomarkers) for certain diseases. As a result, the screening process can be automated to a large extent, and the time for obtaining results significantly shortened when compared to current validations that often involve waiting for disease symptoms to change and also may require tissue biopsies.

Surrogate Markers:

Aspects of the invention may be used for identifying and quantifying vascular patterns (e.g., structural features) that can be used as surrogate markers for diagnostic, therapeutic, and research and development purposes. Surrogate markers are useful for reducing the time of diagnosis, therapy evaluation, and drug development. A surrogate marker can be used as an early indicator for disease diagnosis, disease prognosis, or drug effectiveness, without waiting for a clinical outcome (e.g., increased survival time in response to a drug). So, a vasculature analysis can be used as a surrogate marker for drug development (in both pre-clinical and clinical trials), for clinical screening (e.g., breast, lung, or colon screening), and for clinical therapy monitoring. For example, vasculature structure is a useful surrogate marker for angiogenesis related diseases such as cancer.

In one embodiment, aspects of the invention provide methods for screening and/or validating candidate compounds or therapies for their effectiveness in treating neovasculature formation and/or vasculature pattern changes associated with disease. Aspects of the invention may be used to evaluate individual or small numbers of compounds or to screen libraries to evaluate and/or identify a plurality of candidate compounds (e.g., by administering these compounds, individually or in groups, to an experimental animal such as a mouse and evaluating their effect on angiogenic vasculature). Libraries may contain any number of compounds (e.g., from approximately 100 to approximately 1,000,000) Different types of compounds can be screened, including antibodies, small molecules etc. However, the invention is not limited by the number and/or type of compounds that can be evaluated.

In one embodiment, the effectiveness of a candidate compound can be compared to a reference compound. A reference compound can be any compound with a known effect on a structure. For example, Avastin (Genentech) is a known monoclonal antibody against vascular endothelial growth factor (VEGF) that can be used as a reference to test the effect of a candidate compound on neovasculature growth.

In Vivo Models:

According to aspects of the invention, compounds and therapies can be evaluated in the context of an in-vivo model such as an animal disease model. For example, a mouse with cancer or atherosclerosis can be used to evaluate, optimize, and identify useful therapies. Other animal models also can be used. Aspects of the invention may be useful for high-throughput analyses because they can detect small changes in vasculature and can be used to evaluate a therapy in a short time period with minimal manipulation since little or no invasive procedures are required.

Vascular analysis aspects of the invention can be used on an orthotopic model to test, for example, the effectiveness of a drug in a short period of time. For example, the effect of a candidate drug on angiogenesis in an orthotopic mouse tumor model may be quantifiable after about 5 days (e.g., between 1 and 10 days, depending on the model and the drug). In contrast, a subcutaneous cancer animal model requires approximately one month for tumor growth to be analyzed and compared to controls.

An orthotopic model can be used to model different diseases or clinical conditions. Examples include, cancer, tissue regeneration, wound healing (including healing after traumatic injury, healing after surgical intervention, healing of burnt tissue such as skin), tissue or organ transplant therapy, medical device implant therapy, other conditions associated with neovascularization or changes in normal vascular structure, or any combination of two or more of the above. However, the invention is not limited by the type of orthotopic model or the type of disease or clinical condition that is being analyzed.

A single orthotopic disease model animal may be useful for testing more than one candidate drug molecule since the analysis does not involve sacrificing the model animal. Accordingly, once a test with a first candidate is complete, a subsequent candidate can be evaluated in the same model animal A series of candidates can be tested in a single model animal, with appropriate controls, provided the model retains features of neovascularization that are necessary for the assay.

It should be appreciated that some or all of the development aspects of the invention can be automated as described herein.

Example 6: Interventional Applications

Aspects of the invention also can be used to identify the location of a disease by locating one or more structural abnormalities associated with the disease. This information can be used to target a biopsy procedure or a treatment (e.g., a treatment with one or more toxic chemicals, radiation, heat, cold, small molecules, gene therapy, surgery, any other treatment, or a combination of two or more of the above) to the precise location of a disease lesion, or for any other purpose.

In one embodiment, an imaging device is connected to a computer that provides a real-time visual display of the disease lesion. In one embodiment, a real-time visual display may be an accurate model of a body region and lesion along with associated vasculature (as opposed to an actual image). This visual information can be used to guide a surgical instrument for a biopsy. Alternatively, the information can be used to guide an invasive (e.g., surgical removal or bypass) or non-invasive (e.g., radiation) treatment procedure to the site of the disease lesion (e.g., tumor or blood clot).

In one embodiment, aspects of the invention may be used to identify an area of tissue for treatment before the treatment is applied. For example, a treatment target region may be identified by detecting a boundary of chaotic blood vessel structures. The area may be assessed after treatment to confirm that the treatment was appropriately targeted. In one embodiment, a structure may be analyzed pre-operatively to identify the extent of tissue to be removed from a body region. In one embodiment, a body region may be analyzed post-operatively to determine whether any abnormal structures were missed. This may be used to confirm the success of a radiation treatment or a surgical removal of diseased tissue. Alternatively, this may be used to decide on further surgery and/or another form of treatment. In another embodiment, a disease boundary may be defined or depicted by the boundary of abnormal vasculature. A treatment (e.g., radiation therapy, surgery, etc.) may be guided by and/or restricted to a volume encompassed by the disease boundary.

In one embodiment, aspects of the invention can be used to evaluate the success of a surgical implant or transplant. For example, aspects of the invention can be used to evaluate the formation of new blood vessels after an organ or tissue transplant.

In another embodiment, the development of new blood vessels may be monitored after removal of tumor tissue or after a tumor biopsy, both of which may trigger angiogenesis and/or convert a dormant tumor into a malignant tumor.

It should be appreciated that some or all of the interventional aspects of the invention can be automated as described herein.

Example 7: Xenotopic Tumor Models

A tumor model can be generated by inoculating human non-small cell lung tumor cell line (A549 from ATCC, Inc.) subcutaneously in immunodeficient mice (SCID). SCID male mice (6-8 weeks old from Charles River Inc.) are inoculated subcutaneously in the lower back with a suspension of $1\times10^6$ human lung tumor cells (A549) in 0.2 ml of PBS. All mice are fed normal chow diet throughout the duration of the experiment. All mice weights are measured throughout the experiment. Tumor size is measured with calipers twice-a-week and tumor volume is calculated using the formula $Length^2 \times Width \times 0.52$. All mice are randomized into two treatment groups (approximately 10 mice per group) when the median tumor volume reaches approximately 500 $mm^3$. The treatment groups can be treated according to the following schedule using intraperitoneal (i.p.) administration of either a control composition or an anti-angiogenic compound. For example, different levels of an anti-angiogenic compound can be used and the results compared to a control group that is not treated with an anti-angiogenic compound (e.g., Avastin® available from Genentech, South San Francisco, Calif.). For example:

Group 1: Control group—treated with saline/PBS twice a week.

Group 2: High Avastin®—treated with Avastin® at 5 mg/kg/i.p. twice a week.

Group 3: Low Avastin®—treated with Avastin® at 0.5 mg/kg/i.p. twice a week.

Experiments are terminated 1.5 weeks after initial treatment.

At the end-point, all mice are anesthetized and systemically perfused with a casting agent.

Example 8: Tissue Perfusion with Casting Agent

In some embodiments, a tissue, for example, a tumor tissue, is perfused with a contrast and/or a casting agent prior to image acquisition. Methods of tissue perfusion are well known to those of skill in the art. In some embodiments, a tissue is perfused with Mercox, a casting agent available, for example, from Ladd Research, Williston, Vt. Mercox perfusion can be performed, as follows. An initial anticoagulation step for each animal is performed using an i.v. injection of heparin (10,000 U/ml, 0.3 cc/mouse). After 30 minutes, the animals are anesthetized. Each animal's heart is cannulated and the animal perfused with warm physiological saline at physiological pressure (with an open vein draining the organ or with an open vena cava). Perfusion is continued until the organ or animal is clear of blood. Mercox monomer is filtered through a 0.5 µm filter and a casting resin is prepared by mixing 8 ml Mercox, 2 ml methylmethacrylate, and 0.3 ml catalyst. The resin is infused through the same cannula until the onset of polymerization (the resin changes color to brown and emits heat, ~10 min). The organ or animal is carefully immersed in a 60° C. water bath for 2 hours (or overnight in a sealed container). The tissue is removed by incubating in alternating rinses of 5% KOH and distilled water (for example in a 60° C. water bath sealed) followed by thorough rinsing in distilled water. The cast is cleaned in 5% formic acid for 15 minutes and rinsed thoroughly in distilled water and frozen in distilled water. The resulting block of ice is lyophilized (care should be taken not to melt the ice, the ice should melt as it lyophilizes). The resulting cast can be analyzed to identify one or more structural characteristics of interest.

As used herein, a vascular cast refers to a physical structure that is generated to represent blood vessels of an entire vasculature or portion thereof. A cast may be obtained by perfusing a vasculature or a vascular region (e.g., the blood vessels of an organ, for example, of a kidney or liver) with a casting material that solidifies (e.g., polymerizes) to form a stable structure. The surrounding tissue and cells (e.g., including the blood vessel walls) may be removed to reveal the cast. The cast retains the structural features of the original blood vessels. Cast may include structures of blood vessels of different sizes as described herein. Certain casts are more flexible than others, certain casts are more brittle than others. Vascular casts can be used to identify vascular structural features with high resolution and/or to identify correlations between structural features and conditions of interest with high degrees of confidence since the structures of the blood vessels are retained in the casts and other biological structures that could interfere with an analysis are removed. Vascular casts may be obtained using any suitable casting material. In some embodiments, the casting agent may be a polymer. In some embodiments, the casting agent may react with the blood vessel walls. Non-limiting examples of casting agents include, but are not limited to Microfil®, methyl methacrylate, prepolymerized methyl methacrylate (Mercox™), Mercox™ CL-2B, other acrylic resins, silicon, gold nanoparticles, Batson No. 17, polyurethane-based casting agents (e.g., PU4ii), etc., or combinations of two or more thereof.

It should be appreciated that casting agents may be supplemented with contrast agents and/or other detectable agents. Examples of contrast agents include, but are not limited to, $BaSo_4$ and UAc (e.g., mixed into the casting material). In some embodiments, already polymerized casts can be soaked in $OSO_4$ to achieve better contrast using CT imaging. In certain embodiments, any suitable heavy metal can be mixed into the resin to make it more radioopaque.

Example 9: Response to Antiangiogenic Therapy

Xenotopic mouse models obtained as described in Example 7 can be treated with either a control solution of saline/PBS or an anti-angiogenic preparation of Avastin® at 0.5 mg/kg/i.p. as described above. At the end-point, vascular casts can be prepared as described in Example 8 above and may be analyzed for two treated mice (both treated with Avastin® at 0.5 mg/kg/i.p.) and one control mouse. However, other experimental configurations may be used. The resulting vascular casts can be scanned using a micro CT-scanner and exemplary results of the structural analysis are shown in FIGS. 44-47. In these examples, mean tumor volumes did not differ significantly between the groups at the end of the experiment. However differences in blood vessel density were detected as exemplified in FIGS. 54-67. Further, control and treated tumors also showed differences in vessel diameter distribution. Treated tumors had 20% less small diameter sized vessels than untreated tumors, and treated tumors had a higher percentage of middle diameter sized vessels than untreated tumors. The blood vessel population distributions were consistent for both treated animals. The vessel population ratio between small (approximately 21-35 µm) and middle (approximately 35-49 µm) size vessels in the tumors of the control and treated animals decreased after inhibitor treatment with Avastin®, and this ratio was consistent within the treated group. The vessel population ratio between large (approximately 147-161 µm) and middle (approximately 33-77 µm) size vessels decreased after treatment with Avastin®, and this ratio was consistent within the treated group.

In some embodiments, the effect of an anti-angiogenic drug on a target tissue, for example, a tumor, are assessed using a method provided herein. Anti-angiogenic agents are well known to those of skill in the art and include, for example, Avastin and Macugen. Avastin (bevacizumab) is a monoclonal antibody that binds to Vascular Endothelial Growth Factor (VEGF) and has been proven to inhibit neovascularization of a variety of cancers. Macugen is an aptamer effecting an anti-angiogenic effect by targeting VEGF. Other anti-angiogenic drugs include, for example, antagonists of the SDF/CXCR4 signaling pathway (see, e.g., Guleng et al. Cancer Res. 2005 Jul. 1; 65(13):5864-71), isocoumarin 2-(8-hydroxy-6-methoxy-1-oxo-1H-2-benzopyran-3-yl) propionic acid (NM-3, see, e.g., Agata et al. Cancer Chemother Pharmacol. 2005 December; 56(6):610-4.), thalidomide and thalodimide derivatives (see, e.g., Dredge et al. Microvasc Res. 2005 January; 69(1-2):56-63), and TNF-alpha antagonists (see, e.g., Feldmann et al. Annu Rev Immunol. 2001; 19:163-96).

Example 10: Visualization

Applicant has appreciated the benefit of and has developed visualization tools based on the various analysis techniques described herein. For example, Applicant has appreciated the benefit of being able to visualize various morphological features of vasculature and how they evaluate according to different functions and criteria. As discussed in detail above, regions of a vasculature may be evaluated according to a number of different metrics (e.g., the various measures described in the foregoing, including, but not limited to those shown in Table 1 and 2, iso-shell and hot region analysis evaluated over any one or combination of morphological features and compared to any designated criteria, measures of curvature, tortuosity, branch density, vessel orientation, vessel length, etc. The results of such analytical techniques may be displayed so that various morphological features may be visualized, regions containing particular morphological characteristics may be identified and highlighted, and in general, the results of any of the various analytical techniques (or any others) may be displayed to facilitate a visual understanding of the vasculature of interest.

According to some embodiments, a user interface allows for the display of geometric representations of vasculature after one or more evaluations of morphological features have been performed. The user interface may allow the user to select the morphological feature to analyze, how the feature is to be evaluated and how the results are to be displayed. For example, a user may select that the user would like to analyze vessel density and would like to visualize the density field of the vasculature. FIG. 68 illustrates an example of displaying the density field of the surface of a bounded vasculature, which in FIG. 68 is the wrapped heart vasculature of a mouse. The geometric representation may be viewed at different cross-sections to explore the internals of the vasculature. For example, FIG. 69 illustrates a cross-section of the bounded vasculature in FIG. 68 so that the density field may be visualized internal to the bounded vasculature. As shown, a color (or grayscale) scheme may be used to indicate regions having lower or higher densities. As a result, areas of relatively high and low densities can be immediately visualized to facilitate analysis of the vasculature.

Figure 70:
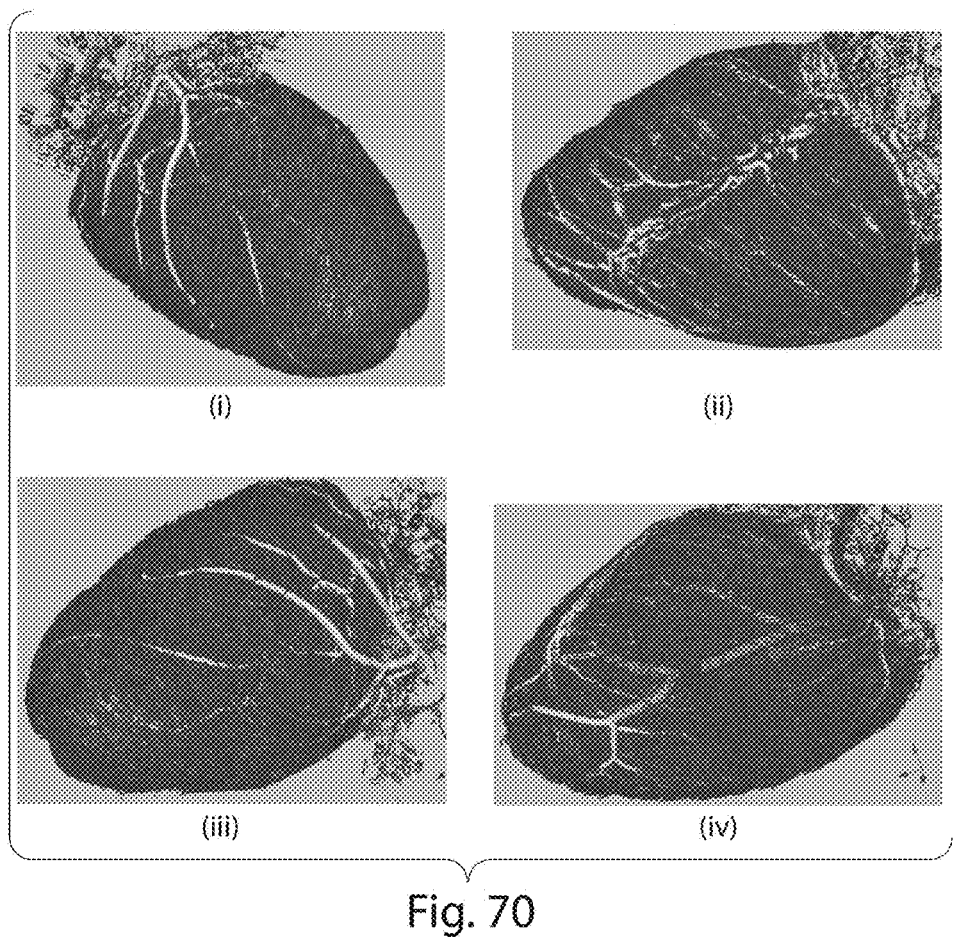
FIG. 70. illustrates different 3D views (i-iv) of mouse heart vasculature.
Figure 71:
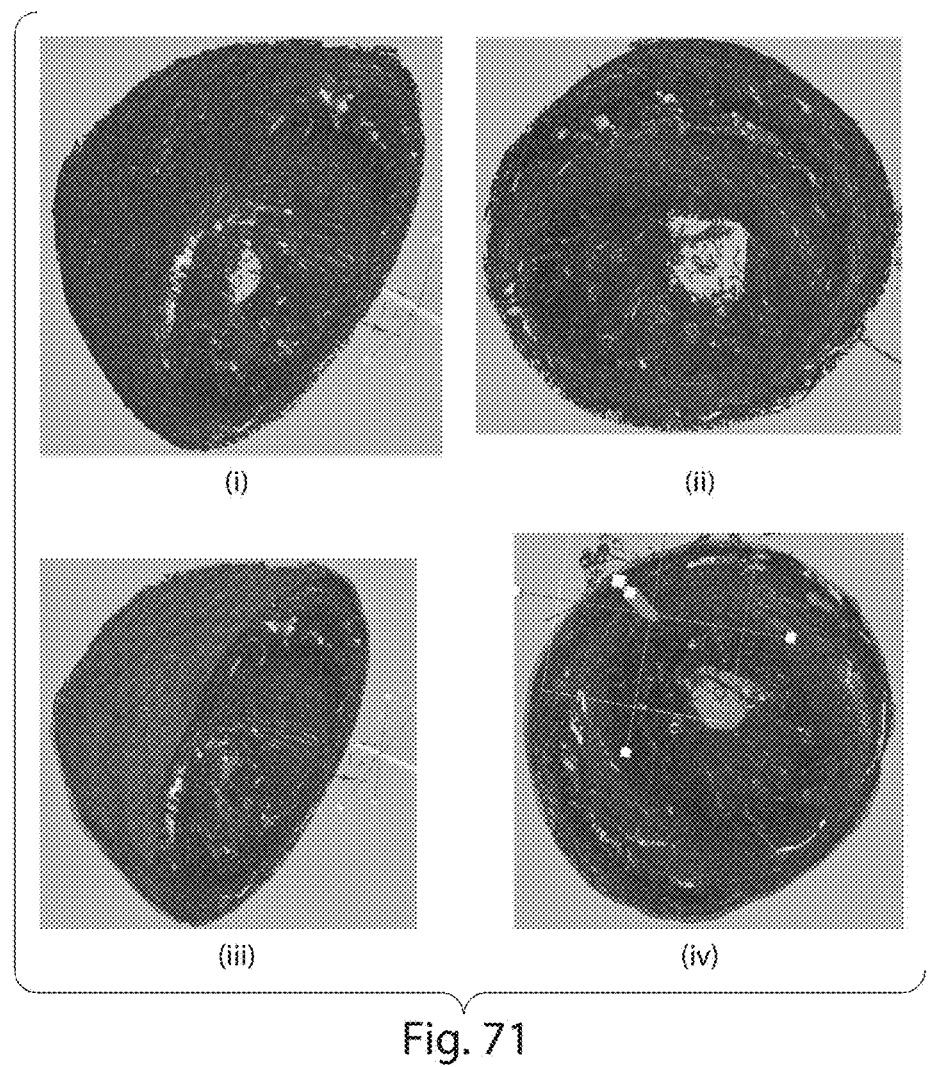
FIG. 71 illustrates different 3D cross section views (i-iv) of mouse heart vasculature.

It should be appreciated that values of any morphological feature may visualized. For example, FIG. 70 illustrates four views of the mouse heart vasculature displayed to visualize vessel diameter and FIG. 71 illustrates four different cross-sections of the mouse heart displayed according to vessel diameter. That is, vessels of different diameters (or within different ranges) may be assigned different colors for intuitive visualization of how vessels of different diameters are distributed within the vasculature. It should be appreciated that any morphological feature that may be evaluated may be visualized. Moreover, various features may visualized together. For example, criteria including multiple thresholds may be used to visualize regions that satisfy criteria for multiple morphological features. Alternatively, color coding may be used to visualize relatively high and low values for multiple morphological features, as the aspects of the invention are not limited in this respect.

Figure 72:
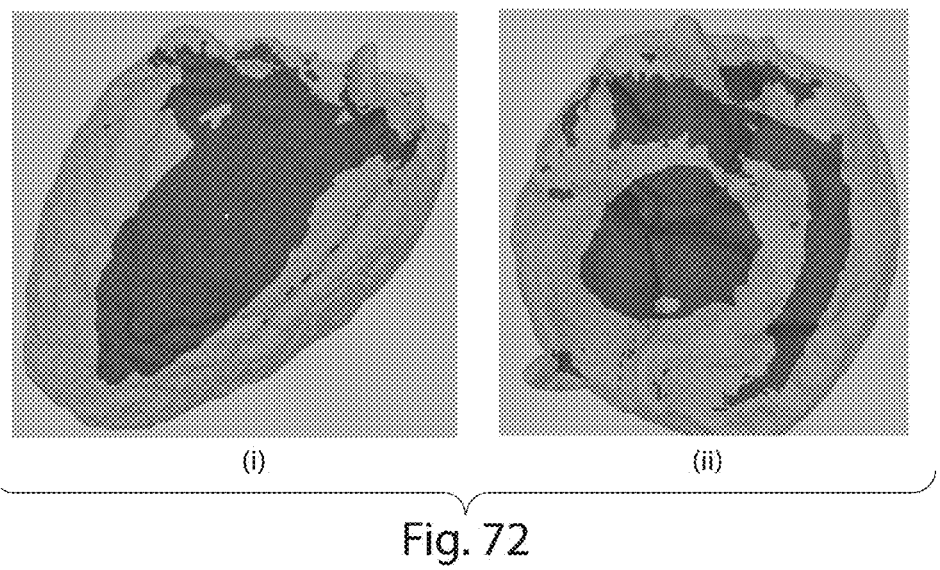
FIG. 72 illustrates a 3D side view of mouse heart vasculature (empty heart chambers)

Designated criteria may be used as a filter to eliminate and/or highlight regions that do or do not satisfy the designated criteria and/or show relatively high or low values for the one or more morphological features being evaluated. For example, FIG. 72 illustrates a threshold value being used to determine regions that fall above or below the designated threshold for the mouse heart vasculature. It should be appreciated that evaluated regions may be displayed using any type of information. For example, overlays using colors, grayscales, numbers, textures, etc. may be used to simultaneously visualize multiple morphological features and values for which those features have been evaluated to allow a user to visualize a richer set of data and how the various morphological characteristics correlate, cluster or otherwise behave. Criteria, threshold(s) and the one or more morphological features to evaluate may be user selectable so that the user can in real time investigate and explore the morphology of the tumor.

Example 10: 2D Analysis

Applicant has appreciated that vascular information (e.g., based on vascular geometry) within a region (e.g., a wrapped 3D region) may be analyzed using one or more 2D slices through the region. It should be appreciated that the slices may be random or may be selected based on one or more predetermined criteria (e.g., proximity to or distance from a structure of interest such as a mother vessel, the edge of the wrap, etc., or any combination thereof). An example of an image of a 2D slice is shown in FIG. 29. Features within the 2D slice may be evaluated as described herein. In a non-limiting embodiment, the total microvasculature density within the slice may be determined (e.g., using any suitable technique described herein). In one example, the mean microvascular density of a mouse heart is about 15% (e.g., from about 13% to about 16%) measured in different slices. This number may be used in some embodiments, as a reference for comparison to disease models, treatment models, etc., relating to cardiovascular conditions. Similar numbers may be obtained for other organs and/or subjects and used as references as described herein. In some embodiments, the vascular density may be analyzed as a distribution of the number, percentage of vasculature volume or area, or percentage of vessels (or other measure) as a function of the vessel diameter. In some embodiments, the vascular density may be analyzed by binning the number, percentage of vasculature volume or area, or percentage of vessels (or other measure) as a function of bins (e.g., defined ranges of vascular diameter). The bins may be based on vessel diameter, vessel cross-section, etc., or any other measure. Any suitable ranges may be used. The ranges may be regular or different is size from bin to bin (e.g., a series of cross-sectional areas of 0-2.96, 2.96-5.91, 5.91-8.87, 8.87-11.8, 11.8-14.8, 14.8-17.7, 17.7-20.7, 20.7-23.6, 23.6-26.6, 26.6-29.6, 29.6-32.5, etc., square um). However, any suitable ranges and sizes may be used for the analysis as aspects of the invention are not limited in this respect.

Example 10: Hot Spot Analysis

Figure 73:
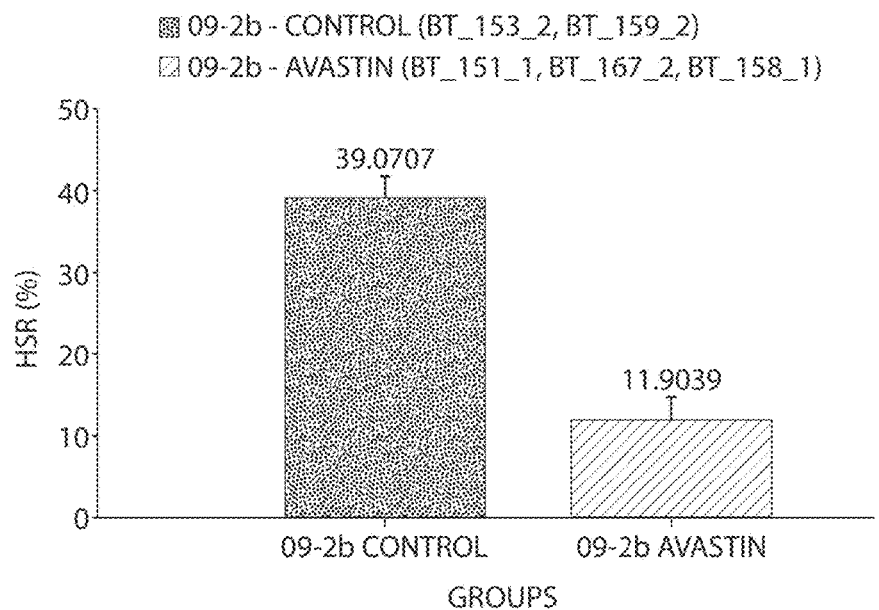
FIG. 73 illustrates Hot Spot Region (HSR) group mean of control and Avastin-treated tumors.
Figure 74:
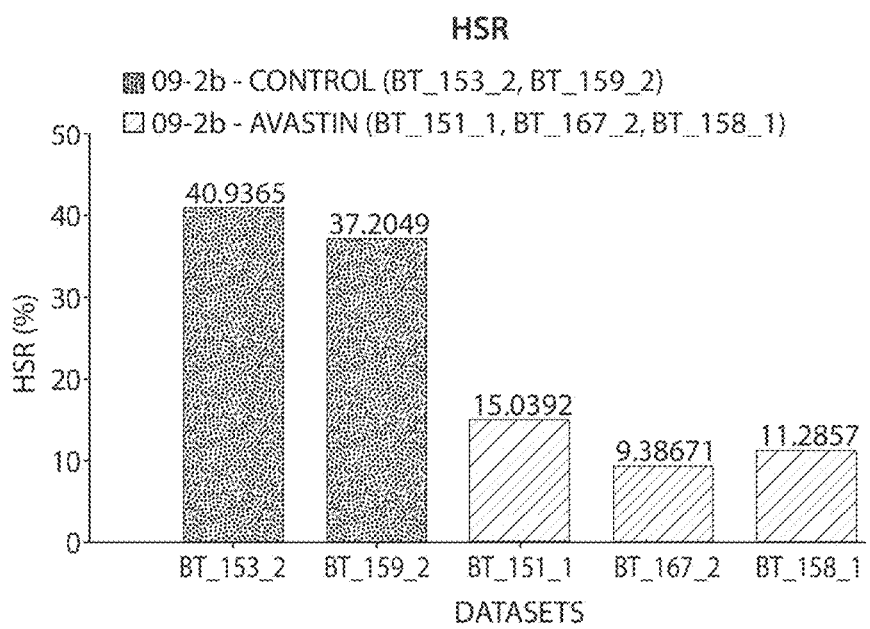
FIG. 74. illustrates HSR of individual control and Avastin-treated tumors.

Applicant has appreciated that vascular information (e.g., based on vascular geometry) within a region (e.g., a wrapped 3D region) may be analyzed to identify one or more hot spots. For example, a threshold number of poker chips may be identified as a threshold for a hot spot within a unit volume of a tumor. The relative amount (e.g., percentage) of tumor vasculature that is represented by a hot spot then may be determined. This value may be used to evaluate the tumor (e.g., for diagnostic or prognostic purposes) or to evaluate a tumor response to therapy. In a non-limiting example, a hot spot may be defined as a cubic millimeter that contains more than 10,000 poker chips. FIGS. 73 and 74 illustrate experiments where the percentage represented by the hot spot regions (e.g., as a percentage of unit volumes within a tumor volume that are above the threshold for defining a hotspot) are evaluated in a mouse tumor model in response to Avastin treatment. The mouse tumor model was generated using H1975 cells. Mice were compared with and without Avastin treatment (Avastin provided for 10 days as described herein). The tumors analyzed were approximately 100 cubic mm in size. FIG. 73 shows the decrease in mean percentage of hot spot regions over the time of the experiment. FIG. 74 shows individual examples. It should be appreciated that this change (or percentage change of about 40% to about 10%) may be used as a marker for response to Avastin and other candidate molecules may be compared to this to determine whether they are as effective.

As described herein, further analyses of the vasculature within the hotspot regions may be performed. Examples of features that may be analyzed for the hot spots vasculature include one or more of 3D total density, 3D MVD, 3D MVD distribution (e.g., as a function of vessel diameter, cross-section, or other measure), 3D binned MVD (e.g., as a function of vessel diameter, cross-section, or other measure), vascular surface (e.g., total or other measure), vascular surface distribution (e.g., as a function of vessel diameter, cross-section, or other measure), vascular population distribution (e.g., as a function of vessel diameter, cross-section, or other measure), vascular density mean distribution (e.g., as a function of vessel diameter, cross-section, or other measure), 2D total density, 2D MVD, 2D MVD distribution (e.g., as a function of vessel diameter, cross-section, or other measure), 2D binned MVD (e.g., as a function of vessel diameter, cross-section, or other measure), or any combination thereof. It should be appreciated that any other morphological characteristics described herein also may be used alone or in combination to evaluate the vasculature within a hot spot region as described herein.

The following considerations apply to the specific examples and the entire written specification herein (including the summary, detailed description, and claims) It should be appreciated that casts, like in situ blood vessels, are three-dimensional structures. Accordingly, imaging and analytical techniques described herein provide information about three-dimensional structural characteristics. In some embodiments, techniques are used to generate three-dimensional representations of vascular casts and/or in situ blood vessels. In some embodiments, techniques are used to generate three-dimensional images of vascular casts and/or in situ blood vessels. The three-dimensional representations and/or images can be analyzed as described herein.

However, it should be appreciated that aspects of the invention are not limited to three-dimensional structural characteristics. In some embodiments, aspects of vascular casts and/or in situ blood vessels may be represented and/or imaged in one or two dimensions and an analysis of one or two-dimensional features may be performed and used as described herein. It also should be appreciated that the structural features described herein may be measured or quantified using any appropriate units, including numbers, lengths or distances, angles, percentages, etc., or any combination thereof, further including any of these units as a function of volume or area. Similarly, it should be appreciated that vascular changes over time or in response to treatment may involve an increase or a decrease of one or more of these structural features. For example, an increase in structures associated with angiogenesis may be associated with certain disease progressions. In contrast, a decrease in structures associated with angiogenesis may be associated with disease regression (e.g., in response to treatment).

It also should be appreciated that descriptions herein related to obtaining distributions of quantitative values for vessel parameters within a region of interest are preferably based on methodologies that detect and quantify all or substantially all of the detectable vessels within the region of interest based on the detection technique that is used for that analysis. Different techniques may have different efficiencies. However, profiles and comparisons are preferably based on data from the same or equivalent detection and/or reconstruction techniques. It also should be appreciated that comparisons and/or analyses described herein may involve a statistical analysis using one or more standard statistical techniques to determine whether a change in a structure or pattern or other characteristic described herein (e.g., an increase or decrease over time, or in response to a therapeutic drug), or a difference or similarity between two structures or patterns or other characteristics described herein are statistically significant.

Having thus described several aspects of at least one embodiment of this invention, it is to be appreciated various alterations, modifications, and improvements will readily occur to those skilled in the art. Such alterations, modifications, and improvements are intended to be within the spirit and scope of the invention. Any suitable analytical techniques may be used for perfused tissue and organs according to the methods described herein, including for example, the analytical techniques that are described in PCT US2005/047081 and PCT US2007/026048 the disclosures of which are incorporated herein by reference in their entirety. Accordingly, the foregoing description and embodiments are by way of example only. In the event of conflict between different disclosures, the disclosure of the present application shall control.

It should be appreciated from the foregoing, there are numerous aspects of the present invention described herein that can be used independently of one another or in any combination. In particular, any of the herein described operations may be employed in any of numerous combinations and procedures. In addition, aspects of the invention can be used in connection with a variety of types of images or any dimensionality. Moreover, one or more automatic operations can be used in combination with one or more manual operations, as the aspects of the invention are not limited in this respect. Distribution analyses, however obtained, may be used to facilitate the characterization of any of various morphological changes to tissue and/or to assist in assessing the efficacy of treatment using any of the herein described techniques, alone or in combination.

The herein-described embodiments of the present invention can be implemented in any of numerous ways. For example, the embodiments of automatic distribution analysis may be implemented using hardware, software or a combination thereof. When implemented in software, the software code can be executed on any suitable processor or collection of processors, whether provided in a single computer or distributed among multiple computers. It should be appreciated that any component or collection of components that perform the functions described herein can be generically considered as one or more controllers that control the herein-discussed functions. The one or more controllers can be implemented in numerous ways, such as with dedicated hardware, or with general purpose hardware (e.g., one or more processors) that is programmed using microcode or software to perform the functions recited herein.

It should be appreciated that the various methods outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code. It should be appreciated that one embodiment of the invention is directed to a non-transitory computer-readable medium or multiple computer-readable media (e.g., a computer memory, one or more floppy disks, compact disks, optical disks, magnetic tapes, etc.) encoded with one or more programs that, when executed, on one or more computers or other processors, perform methods that implement the various embodiments of the invention discussed herein.

The computer-readable medium or media can be transportable, such that the program or programs stored thereon can be loaded onto one or more different computers or other processors to implement various aspects of the present invention as discussed herein. It should be understood that the term "program" is used herein in a generic sense to refer to any type of computer code or set of instructions that can be employed to program a computer or other processor to implement various aspects of the present invention as discussed herein. Additionally, it should be appreciated that according to one aspect of this embodiment, one or more computer programs that, when executed, perform methods of the present invention need not reside on a single computer or processor, but may be distributed in a modular fashion amongst a number of different computers or processors to implement various aspects of the present invention.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. A method of performing vascular analysis using a geometric representation of a plurality of vessels of the vasculature, the method comprising:
    extracting information from one or more images using a centerline filter to identify the vessels, wherein each vessel is represented as an aggregation of cylinder cross-sections, each defined by a center location, a radius and an orientation;
    linking the cylinder cross-sections together, using center location and orientation information, to construct vessels, wherein the geometric representation comprises a collection of all of the vessels;
    computing a boundary of a portion of the vasculature based on a criteria corresponding to one or more features of the geometric representation;
    dividing the geometric representation within the boundary into a plurality of regions;
    analyzing at least one geometric feature for each of the plurality of regions within the boundary to confirm the presence of a disease, determine a location for the disease-associated lesion, evaluate a response to therapy or provide an evaluation or prognosis of a disease; and
    displaying a result of the analyzing using a user interface.

2. The method of claim 1, wherein logically dividing the geometric representation includes defining a plurality of shells, each of the plurality of shells defining a respective range of distances from the boundary and including within each location within the boundary having a distance from the boundary within the respective range of the corresponding shell.

3. The method of claim 2, further comprising performing at least one evaluation of the at least one geometric feature for each of the plurality of shells, wherein the at least one geometric feature is selected from the group consisting of vessel density, branch density, vessel curvature, vessel tortuosity, vessel orientation and vessel length.

4. The method of claim 3, wherein the at least one evaluation includes performing at least one density evaluation of the at least one geometric feature for each of the plurality of shells.

5. The method of claim 4, wherein the at least one density evaluation includes at least one evaluation based on vessel density and/or branch density.

6. The method of claim 3, wherein the at least one evaluation includes evaluating vessel curvature, vessel tortuosity, vessel orientation and/or vessel length.

7. The method of claim 1, wherein analyzing at least one geometric feature for each of the plurality of regions includes determining at least one value for the at least one geometric feature and comparing the at least one value to a designated criteria.

8. The method of claim 7, wherein the at least one value includes at least one value indicative of a density of the at least one geometric feature.

9. The method of claim 8, wherein the at least one value indicative of a density includes at least one value indicative of a vessel density and/or at least one value indicative of branch density.

10. The method of claim 7, wherein the at least one value includes at least one value indicative of vessel curvature, vessel tortuosity, vessel orientation and/or vessel length for each of the plurality of regions.

11. The method of claim 1, wherein the portion of the vasculature includes tumor vasculature, organ vasculature or vasculature of a region of an organ.

12. At least one non-transitory computer readable medium encoded with instructions that, when executed on at least one processor, performs a method of performing vascular analysis using a geometric representation of a plurality of vessels of the vasculature, the method comprising:
    extracting information from one or more images using a centerline filter to identify the vessels, wherein each vessel is represented as an aggregation of cylinder cross-sections, each defined by a center location, a radius and an orientation;
    linking the cylinder cross-sections together, using center location and orientation information, to construct vessels, wherein the geometric representation comprises a collection of all of the vessels;
    computing a boundary of a portion of the vasculature based on a criteria corresponding to one or more features of the geometric representation;
    dividing the geometric representation within the boundary into a plurality of regions;
    analyzing at least one geometric feature for each of the plurality of regions within the boundary to confirm the presence of a disease, determine a location for the disease-associated lesion, evaluate a response to therapy or provide an evaluation or prognosis of a disease; and
    displaying a result of the analyzing using a user interface.

13. The at least one non-transitory computer readable medium of claim 12, wherein logically dividing the geometric representation includes defining a plurality of shells, each of the plurality of shells defining a respective range of distances from the boundary and including within each location within the boundary having a distance from the boundary within the respective range of the corresponding shell.

14. The at least one non-transitory computer readable medium of claim 13, further comprising performing at least one evaluation of the at least one feature for each of the plurality of shells, wherein the at least one feature is selected from the group consisting of vessel density, branch density, vessel curvature, vessel tortuosity, vessel orientation and vessel length.

15. The at least one non-transitory computer readable medium of claim 14, wherein the at least one evaluation includes performing at least one density evaluation of the at least one feature for each of the plurality of shells.

16. The at least one non-transitory computer readable medium of claim 15, wherein the at least one density evaluation includes at least one evaluation based on vessel density and/or branch density.

17. The at least one non-transitory computer readable medium of claim 13, wherein the at least one evaluation includes evaluating vessel curvature, vessel tortuosity, vessel orientation and/or vessel length.

18. The at least one non-transitory computer readable medium of claim 12, wherein analyzing at least one feature for each of the plurality of regions includes determining at least one value for the at least one feature and comparing the at least one value to a designated criteria.

19. The at least one non-transitory computer readable medium of claim 18, wherein the at least one value includes at least one value indicative of a density of the at least one feature.

20. An apparatus for performing vascular analysis using a geometric representation of a plurality of vessels of the vasculature, the apparatus comprising:
- at least one storage medium for storing the geometric representation; and
- at least one computer capable of accessing the at least one storage medium to process the geometric representation, the at least one computer programmed to:
  extract information from one or more images using a centerline filter to identify the vessels, wherein each vessel is represented as an aggregation of cylinder cross-sections, each defined by a center location, a radius and an orientation;
  link the cylinder cross-sections together, using center location and orientation information, to construct vessels, wherein the geometric representation comprises a collection of all of the vessels;
  compute a boundary of a portion of the vasculature based on a criteria corresponding to one or more features of the geometric representation;
  divide the geometric representation within the boundary into a plurality of regions;
  analyze at least one geometric feature for each of the plurality of regions within the boundary to confirm the presence of a disease, determine a location for the disease-associated lesion, evaluate a response to therapy or provide an evaluation or prognosis of a disease; and
  display a result of the analyzing using a user interface.

* * * * *